United States Patent
Garst et al.

(10) Patent No.: US 7,294,716 B2
(45) Date of Patent: Nov. 13, 2007

(54) PROCESS FOR PREPARING ISOMERICALLY PURE PRODRUGS OF PROTON PUMP INHIBITORS

(75) Inventors: Michael E. Garst, Newport Beach, CA (US); Lloyd Jay Dolby, Eugene, OR (US); Shervin Esfandiari, Eugene, OR (US); Vivian Rose MacKenzie, Eugene, OR (US); Alfred Arthur Avey, Jr., Eugene, OR (US); David Charles Muchmore, Eugene, OR (US); Geoffrey Kenneth Cooper, Scappoose, OR (US); Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 480 days.

(21) Appl. No.: 10/891,317

(22) Filed: Jul. 13, 2004

(65) Prior Publication Data

US 2005/0038076 A1    Feb. 17, 2005

Related U.S. Application Data

(60) Provisional application No. 60/487,340, filed on Jul. 15, 2003.

(51) Int. Cl.
*C07D 401/12* (2006.01)
*C07D 401/14* (2006.01)
*C07D 409/14* (2006.01)

(52) U.S. Cl. .................. 546/273.7; 544/353; 544/354; 544/355; 546/153; 546/168; 546/172; 546/256

(58) Field of Classification Search ................ 544/353, 544/354, 355; 546/153, 168, 172, 256, 273.7
See application file for complete search history.

(56) References Cited

U.S. PATENT DOCUMENTS

| 4,255,431 A | 3/1981 | Junggren et al. |
|---|---|---|
| 4,628,098 A | 12/1986 | Nohara et al. |
| 4,758,579 A | 7/1988 | Kohl et al. |
| 5,039,806 A | 8/1991 | Brandstram et al. |
| 5,045,552 A | 9/1991 | Souda et al. |
| 5,693,818 A | 12/1997 | Von Unge |
| 6,093,734 A | 7/2000 | Garst et al. |
| 6,559,167 B1 | 5/2003 | Garst et al. |
| 6,897,227 B2 * | 5/2005 | Garst et al. ............ 514/341 |
| 2002/0082280 A1 | 6/2002 | Sperl et al. |

FOREIGN PATENT DOCUMENTS

| WO | WO 00/09498 A | 2/2000 |
|---|---|---|
| WO | WO 00109498 | 2/2000 |

OTHER PUBLICATIONS

Victor T et al: "Synthesis and Antiviral Activity of C2 Analogs of Enviroxime: An Exploration of the Role of Critical Functionality" Journal of Medicinal Chemistry, American Chemical Society. Washington, US, vol. 40, 1997, pp. 3478-3483, XP002288472 ISSN: 002-2623.

Betrha F et al: "Benzoxadiazocines, Benzothiadiazocines and Benzotriazocines-II" Tetrahedron, Elsevier Science Publishers, Amsterdam, NL, vol. 39, No. 7, 1983, pp. 1199-1201, XP002288473 ISSN: 0040-4020.

Hornyak G et al: "Benzoxadiazocines, Benzothiadiazocines and Benzotriazocines-I" Tetrahedron, Elsevier Science Publishers, Amsterdam, NL, vol. 39, No. 3, 1983, pp. 479-481, XP002288474 ISSN: 0040-4020.

* cited by examiner

*Primary Examiner*—Patricia L. Morris
(74) *Attorney, Agent, or Firm*—Gabor L. Szekeres; Brent A. Johnson; Martin A. Voet

(57) ABSTRACT

Synthetic methods for preparing isomerically pure N-arylsulfonyl derivatives of proton pump inhibitors which include a substituted benzimidazole nucleus are shown by the synthetic schemes and experimental description.

29 Claims, No Drawings

PROCESS FOR PREPARING ISOMERICALLY PURE PRODRUGS OF PROTON PUMP INHIBITORS

CROSS-REFERENCE TO RELATED APPLICATION

The present application claims the priority of U.S. provisional application Ser. No. 60/487,340 filed on Jul. 15, 2003.

FIELD OF THE INVENTION

The present invention is directed to synthetic processes for preparing isomerically pure prodrugs of proton pump inhibitors. More particularly, the present invention is directed to an improved synthetic process for preparing isomerically pure prodrugs of the known proton pump inhibitors OMEPRAZOLE and PANTOPRAZOLE.

BRIEF DESCRIPTION OF THE PRIOR ART

Certain benzimidazole compounds capable of inhibiting the gastric H,K-ATPase enzyme have found substantial use as drugs in human medicine and are known under such names as LANSOPRAZOLE (U.S. Pat. No. 4,628,098), OMEPRAZOLE (U.S. Pat. Nos. 4,255,431 and 5,693,818), PANTOPRAZOLE (U.S. Pat. No. 4,758,579), and RABEPRAZOLE (U.S. Pat. No. 5,045,552). These drugs, that are generally known as species of a larger class of "proton pump inhibitors" (ppi), are used to treat diseases and conditions which include peptic ulcer, heart burn, reflux esophagitis errosive esophagitis, non-ulcer dispepsia, infection by *Helicobacter pylori*, laryngitis and asthma among others.

Prodrugs of the proton pump inhibitor drugs have also been developed in the prior art. These are compounds which after administration undergo spontaneous or enzyme catalyzed conversion to the physiologically active species. U.S. Pat. Nos. 6,093,734, 6,599,167 and PCT Publication WO 00/09498 describe such prodrugs of the four major presently used proton pump inhibitors (known as LANSOPRAZOLE, OMEPRAZOLE, PANTOPRAZOLE AND RABEPRAZOLE) where one of the nitrogen atoms of the benzimidazole nucleus is substituted with an arylsulfonyl group. The known ppi drugs OMEPRAZOLE and PANTOPRAZOLE include a $CH_3O$ or $HF_2CO$ substituent, respectively in the benzimidazole ring moiety, whereby the two nitrogens in the imidazole portion are not chemically equivalent. In the processes previously described for the preparation of the prodrugs of OMEPRAZOLE and PANTOPRAZOLE usually two isomers are formed wherein the arylsulfonyl moiety is attached to the two different nitrogens of the benzimidazole moiety. The two isomers can be, but are not necessarily formed in equal amounts, and may have different degree of biological activity, and stability. Whereas these isomers can be separated by conventional techniques (such as high pressure liquid chromatography) there is a need in the art for an improved processes whereby each isomer of the prodrug can be prepared in an isomerically pure form. The present invention provides such a synthetic process.

SUMMARY OF THE INVENTION

The present invention relates to methods of synthesizing compounds of Formula 1, Formula 2, Formula 3 and Formula 4

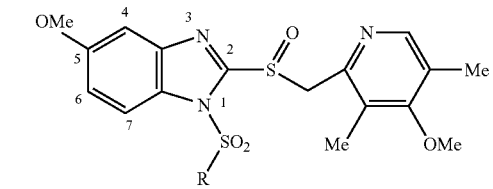

Formula 1

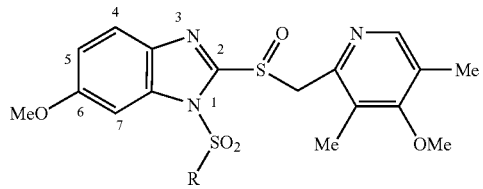

Formula 2

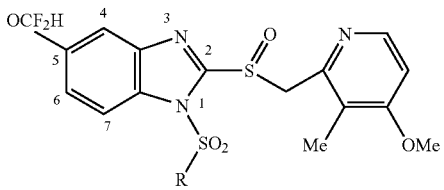

Formula 3

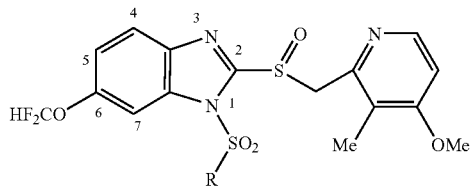

Formula 4 where the R group, generally speaking, represents an alkylsulfonyl, arylsulfonyl, substituted arylsulfonyl, heteroarylsulfonyl or substituted heteroarylsulfonyl group.

Specifically, the R group is defined as a group selected from Formulas (i) through (viii);

where the dashed line represents the bond connecting the R group with the $SO_2$ group,

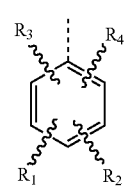

(i)

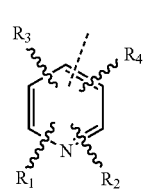

(ii)

-continued

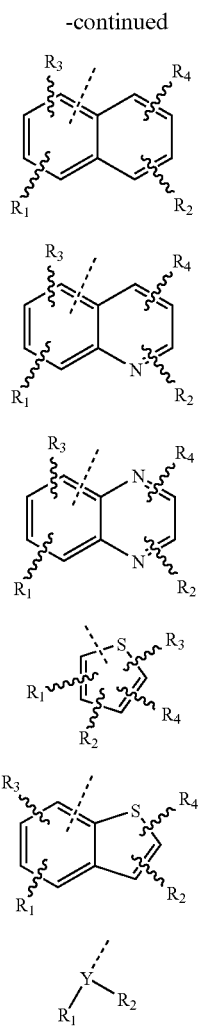

(iii)
(iv)
(v)
(vi)
(vii)
(viii)

Y is a straight chained or branch-chained disubstituted alkyl group of 1 to 8 carbons, or Y is N;

$R_1$ and $R_2$ independently are H, a straight chained or branch-chained di- or tri-substituted alkyl group of 1 to 12 carbons including 1 or two $R_5$ groups, or a straight chained or branch-chained saturated hydrocarbon skeleton having no more than 12 carbons including 1 or two $R_5$ groups and optionally further including one to three X groups where X is independently selected from the group consisting of —O—, —S—, —$NR_6$—, —NHCO—, —CONH—, —CONHCO—, —COO—, —OCO— and a disubstituted phenyl group which can optionally be substituted with one or two halogen atoms or with one or two $R_3$ groups; or the $R_5$ group is directly attached without an intervening $R_1$ or $R_2$ group to the aromatic or heteroaromatic ring or to the Y group of formulas (i) through (viii);

$R_3$ and $R_4$ independently are H, alkyl of 1 to 3 carbons, fluoroalkyl of 1 to 3 carbons, O-alkyl of 1 to 3 carbons, O-fluoroalkyl of 1 to 3 carbons, S-alkyl of 1 to 3 carbons, S-fluoroalkyl of 1 to 3 carbons;

$R_5$ is independently H, COOH or a tetrazole moiety;

$R_6$ is H or alkyl of 1 to 3 carbons;

with the provisos that at least one the $R_1$ and $R_2$ groups is not H, and at least one $R_5$ is not H and no more than two $R_5$ groups are COOH or tetrazole whereby the compound includes at least one but no more than two COOH or tetrazole groups; when Y is —N then neither of the $R_1$ and $R_2$ groups is H, or a pharmaceutically acceptable salt of said compound.

Alternatively, for the purposes of the process of the present invention the R group is also defined as the group attached to the sulfonyl group in the prodrugs described in U.S. Pat. Nos. 6,093,734 and 6,559,167.

The process of the invention is shown in general terms in Reaction Scheme 1, where the variable R is defined as above. The XO group represents $CH_3O$ in the process of preparing isomerically pure prodrugs of OMEPRAZOL and $HF_2CO$ in the process of preparing isomerically pure prodrugs of PANTOPRAZOL. When a prodrug is desired where the XO group is attached to the 5-position of the benzimidazole moiety of the prodrug, then the XO group is attached to the 4-position of the phenyl group of the compound of Formula 5 (as shown by the numbering next to the formula). When a prodrug is desired where the XO group is attached to the 6-position of the benzimidazole moiety of the prodrug, then the XO group is attached to the 5-position of the phenyl group of the compound of Formula 5 (as shown by the numbering next to the formula).

The compound of Formula 5 is an 1-arylsulfonylamino-2-amino-benzene ("diamino compound") that, as noted above, is also substituted by the XO group in the 4 or 5 position, as desired. Such 1-arylsulfonylamino-2-amino-benzene derivatives of Formula 5 can be obtained either in accordance with the chemical scientific and patent literature or by such modifications of the reactions described here in connection with the specific examples which will be readily apparent to those skilled in the art in light of the present disclosure.

As is shown in Reaction Scheme 1, the diaamino compound of Formula 5 is ring closed by treatment with thiocarbonyldiimidazole ($Im_2C=S$) to provide a 2-thiobenzimidazole derivative of Formula 6. Alternatively phenylisocyanate ($C_6H_5NCS$), or thiophosgene ($CSCl_2$) can also be used for the ring closure. In the compound of Formula 6 the XO group is attached to the desired 5- or to the desired 6-position of the benzimidazole moiety, depending on the position of the same group in the starting material of Formula 5. The 2-thiobenzimidazole derivative of Formula 6 is then reacted with the 2-chloromethyl-pyridine derivative of Formula 7 to give rise to a N-1-sulfonyl-(2-pyridyl)) methylthio]-benzimidazole derivative of Formula 8.

The variables $X_1$, $X_2$ and $X_3$ in Formula 8 represent such substituents of the pyridine nucleus that provide the appropriate substituted pyridine moiety for OMEPRAZOLE and PANTOPRAZOLE, respectively. Thus, in the process of making prodrugs of OMEPRAZOLE $X_1$ and $X_3$ represent methyl groups attached to the 3 and 5 position of pyridine and $X_2$ represents a methoxy ($CH_3O$) group attached to the 4 position of the pyridine nucleus in Formula 7. In the process of making prodrugs of PANTOPRAZOLE $X_1$ and $X_2$ represent methoxy ($CH_3O$) groups attached to the 3 and 4 position of pyridine and $X_3$ represents hydrogen in Formula 7.

The thioether linkage of the compound of Formula 8 is oxidized to the sulfoxide level by treatment with 3-chloroperoxybenzoic acid (meta-chloroperbenzoic acid, m-ClPBA) or by another suitable reagent, such as magnesium monoperphthalate, to yield the desired isomerically pure prodrug of OMEPRAZOLE or PANTOPRAZOL of Formula 9.

Reaction Schemes 2 to 15 incorporated in the section titled Specific Examples below, disclose the presently preferred synthetic routes to exemplary preferred compounds that are made in accordance with the process of the present invention.

In addition, those compounds made in accordance with the herein described novel processes that include one or more acidic function (such as a carboxylic acid group) in the

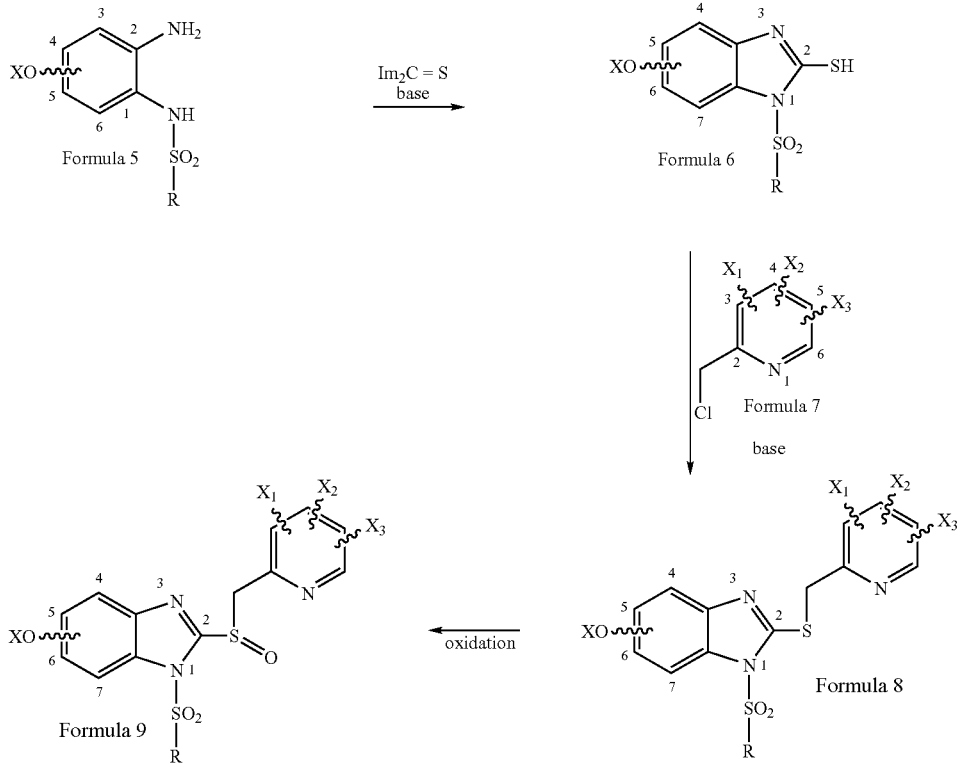

Reaction Scheme 1

Biological Activity, Use of the Compounds Made by the Process, Modes of Administration Generally speaking the prodrugs of proton pump inhibitors made by the process of the present invention can be used as described in U.S. Pat. Nos. 6,093,734 and 6,599,167, incorporated herein by reference.

Briefly summarized, a significant advantage of the compounds made in accordance with the process of the present invention is that the compounds can release the active forms of the proton pump inhibitors spontaneously by hydrolysis in the mammalian (including human) body. Hydrolysis can occur chemically or enzymatically. Because the compounds of this invention spontaneously release the active form of the proton pump inhibitor drugs by in vivo hydrolysis, they can attain longer duration of effective drug concentration in the body. Thus, the compounds of the present invention are prodrugs which are converted to active drugs by hydrolysis in the body, providing long duration of effective concentration. The long duration of inhibitory activity by spontaneous hydrolysis of the compounds of this invention allows more effective inhibition of gastric acid secretion, which enables better therapy of acid related disease defined above. Compounds of this invention can be administered for inhibiting gastric acid secretion orally. The typical daily dose of the compounds will depend on various factors such as the individual requirement of each patient. In general, oral and parenteral dosages will be in the range of 5 to 300 mg per day. For further description of results obtained in biological tests, reference is made again to U.S. Pat. Nos. 6,093,734 and 6,599,167.

moiety designated R in Formulas 1 through 4 have improved solubility and improved bioavailability relative to the compounds lacking an acidic function, such as the compounds of U.S. Pat. Nos. 6,093,734 and 6,599,167.

PREFERRED EMBODIMENTS

Preferably the process of the present invention, shown in Reaction Scheme 1, is utilized to prepare such prodrugs of OMEPRAZOLE and PANTOPRAZOLE where the respective $CH_3O$ or $HF_2CO$ substituent is in the 5-position of the benzimidazole moiety. The preparation of prodrugs of OMEPRAZOLE in accordance with the invention is presently preferred.

The process or synthetic method of the present invention may also include additional reaction steps. These are shown in detail in the enclosed Specific Examples. Inasmuch as the preparation of such compounds of Formulas 1 to 4 is presently preferred where the substituent R bears at least one carboxylic acid moiety (specifically $R_5$ attached to R is a carboxylic acid) the synthetic method of preparing the compounds frequently includes an additional step wherein an ester of the carboxylic acid group is saponified by treatment with base.

The process of the invention may also include additional steps to prepare the 1-arylsulfonylamino-2-amino-benzene derivative of Formula 5 ("diamino compound") that is ring closed in the first step shown in Reaction Scheme 1 to form a benzimidazole moiety.

The presently most preferred specific synthetic processes or methods of the invention, including specific steps to obtain the specific intermediate-corresponding to Formula 5, are shown in the Specific Examples.

SPECIFIC EXAMPLES
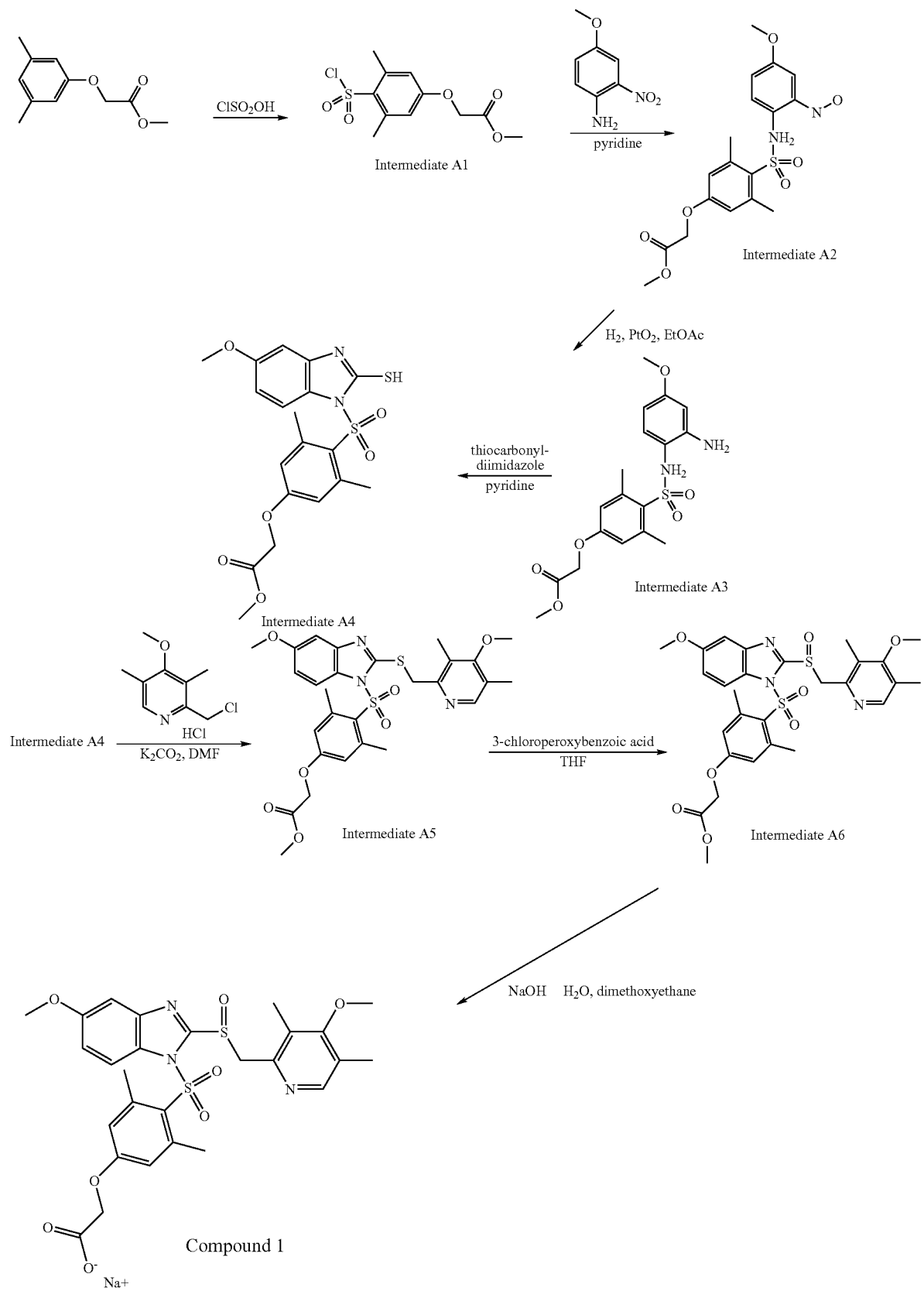
Reaction Scheme 2

In the following reaction schemes and examples, as in the entire disclosure, unless it is expressly noted otherwise the reagents and/or starting materials are either available commercially or can be prepared in accordance with the chemical scientific and patent literature readily accessible to those of ordinary skill in the art.

Methyl
(4-chlorosulfonyl-3,5-dimethylphenoxy)acetate
(Intermediate A1)

Methyl (3,5-dimethylphenoxy)acetate (19.4 g, 0.10 mol) was added dropwise over ca. 30 min to rapidly stirred chlorosulfonic acid (58 g, 0.50 mol)that was cooled in a −20° C. bath. After an additional 20 min, the mixture was allowed to slowly warm to room temperature. After 2 hr, the mixture was poured slowly into 400 mL of ice/water. This suspension was extracted with 400 mL of dichloromethane, and the organic layer was washed with water and concentrated. The residue was purified by flash silica gel chromatography (hexanes→dichloromethane) to yield 7.6 g (27%) of the title compound.

Methyl [4-(4-methoxy-2-nitrophenyl)aminosulfonyl-3,5-dimethylphenoxy]acetate (Intermediate A2)

A mixture of methyl (4-chlorosulfonyl-3,5-dimethylphenoxy)acetate (Intermediate A1, 7.6 g, 0.026 mol), 4-methoxy-2-nitroaniline (4.0 g, 0.024 mol), and pyridine (50 mL) was stirred at room temperature for 16 hr, in a 90° C. bath for 5 hr, and in a 130° C. bath for 30 min. The mixture was cooled and stirred with toluene for 10 min. The resulting suspension was filtered, and the filtrate was concentrated, diluted with 150 mL toluene and 100 mL ethyl acetate, washed with 1 M hydrochloric acid and water, and concentrated to about 50 mL. The mixture was left overnight in a freezer. The solid was collected and washed with several portions of cold toluene. After drying, it weighed 8.2 g (74%). Another 0.45 g portion of the title compound was recovered from extraction of aqueous phases and crystallization of a second crop from the toluene filtrate.

Methyl [4-(2-amino-4-methoxyphenyl)aminosulfonyl-3,5-dimethylphenoxy]acetate (Intermediate A3)

Methyl [4-(4-methoxy-2-nitrophenyl)aminosulfonyl-3,5-dimethylphenoxy]acetate (Intermediate A2, 8.1 g, 0.019 mol) in 200 mL ethyl acetate was stirred with Raney nickel (0.75 g) for 30 min and filtered through a celite pad with the aid of an additional 100 mL of ethyl acetate. The filtrate was mixed with platinum oxide (0.40 g, 0.0018 mol) and hydrogenated to give 7.8 g (100%) of the title compound.

Methyl {4-[(2-mercapto-5-methoxybenzimidazolyl)sulfonyl]-3,5-dimethylphenoxy}acetate (Intermediate A4)

Methyl [4-(2-amino-4-methoxyphenyl)aminosulfonyl-3,5-dimethylphenoxy]acetate (Intermediate A3, 7.5 g, 0.019 mol), thiocarbonyldiimidazole (5.1 g, 0.029 mol), and pyridine (100 mL) were mixed and stirred for 3 hr. The reaction mixture was poured into 1 L of rapidly stirring water. After 2 hr, the resulting solid was collected, washed with several portions of water, and air-dried to give 8.9 g (110%) of the desired title compound contaminated with some pyridine. The impure product was used in the alkylation step.

2-Chloromethyl-3,5-dimethyl-4-methoxypyridine hydrochloride

To a solution of 4-methoxy-3,5-dimethylpyridinemethanol (25.1 g, 0.15 mol) in dichloromethane (400 mL) was added a solution of thionyl chloride (18.8 g, 0.158 mol) in dichloromethane (100 mL) over 30 min at room temperature under argon. After an additional 30 min of stirring at room temperature, the solvent was removed under reduced pressure. The solid residue was suspended in hexanes (200 mL) and filtered. The solid was washed with hexanes (50 mL) and air-dried to give 33.3 g (100%) of the title compound as a white solid.

Methyl {4-[(5-methoxy-2{[4-methoxy-3,5-dimethyl (2-pyridyl)methyl]thio}benzimidazolyl)sulfonyl]-3,5-dimethylphenoxy}Acetate (Intermediate A5)

2-Chloromethyl-3,5-dimethyl-4-methoxypyridine hydrochloride (4.4 g, 0.020 mol) was added to a mixture of methyl {4-[(2-mercapto-5-methoxybenzimidazolyl)sulfonyl]-3,5-dimethylphenoxy}acetate (Intermediate A4, 8.2 g, 0.019 mol), potassium carbonate (5.7 g, 0.041 mol), and dimethylformamide (80 mL). The mixture was stirred for 1.5 hr and was then poured in 150 mL of rapidly stirring ice water containing 40 mL of 1.2 M hydrochloric acid. The resulting solid was collected and washed with several portions of water. After partial air-drying, the 10 g of solid was dissolved in 100 mL of dichloromethane. This solution was washed with saturated aqueous sodium bicarbonate, filtered through 1PS paper, and concentrated. The residue was mixed with boiling methanol and collected, yielding 8.9 g (80%) of the title compound.

Methyl {4-[(5-methoxy-2{[4-methoxy,3,5-dimethyl (2-pyridyl)methyl]sulfinyl}benzimidazolyl)sulfonyl]-3,5-dimethylphenoxy}acetate (Intermediate A6)

Solutions of methyl {4-[(5-methoxy-2{[4-methoxy,3,5-dimethyl(2-pyridyl)methyl]thio}benzimidazolyl)sulfonyl]-3,5-dimethylphenoxy}acetate (Intermediate A5, 7.1 g, 0.12 mol) in 100 mL of tetrahydrofuran and 3-chloroperoxybenzoic acid (2.6 g, 0.15 mol) in 20 mL of the same solvent were cooled in a freezer for 1 hr and then mixed. The solution was left in the freezer for about 16 hr, diluted with ethyl acetate, and washed with several portions each of 5% sodium metabisulfite, 5% sodium bicarbonate, and saturated sodium chloride. The organic phase was concentrated and then purified on flash silica gel (hexanes→ethyl acetate→1% methanol in ethyl acetate). The title compound recovered weighed 3.3 g (46%).

2-{4-[(5-methoxy-2-{[(4-methoxy-3,5-dimethyl(2-pyridyl))methyl]sulfinyl}benzimidazolyl)sulfonyl]-3,5-dimethylphenoxy}acetic acid sodium salt (Compound 1)

A solution of methyl {4-[(5-methoxy-2{[4-methoxy,3,5-dimethyl(2-pyridyl)methyl]sulfinyl}benzimidazolyl)sulfonyl]-3,5-dimethylphenoxy}acetate (Intermediate A6, 2.96 g, 0.493 mol) in 250 mL of dimethoxyethane was stirred rapidly as 49 mL of 0.100 N aqueous sodium hydroxide was added. The mixture was concentrated at aspirator pressure (bath temperature<22° C.). The residue was reconcentrated from 200 mL of dimethoxyethane, left briefly at high vacuum, and partitioned between ethyl acetate and water. The aqueous layer was washed with several portions of ethyl acetate and was then concentrated at high vacuum. The residue was partitioned between ethyl acetate and water at pH 3. The aqueous layer was extracted with an additional portion of ethyl acetate, and the combined organic layers were reduced in volume and diluted with hexanes. The resulting solid was collected and combined with a second crop recovered from the filtrate. This material was washed with 10:1 diethyl ether:tetrahydrofuran, dissolved in dimethoxyethane, neutralized with 0.0100 N sodium hydroxide, and washed with ethyl acetate. The product, title compound weighed 0.925 g (31%).

NMR (300 MHz) (D$_2$O) δ 7.9 (s, 1H); 7.2-6.6 (complex, 5H); 4.9-4.6 (AB, 2H); 4.4 (s, 2H); 3.7 (s, 3H); 3.5 (s, 3H); 2.2 (s, 6H); 2.0 (s, 3H); 1.9 (s, 3H).

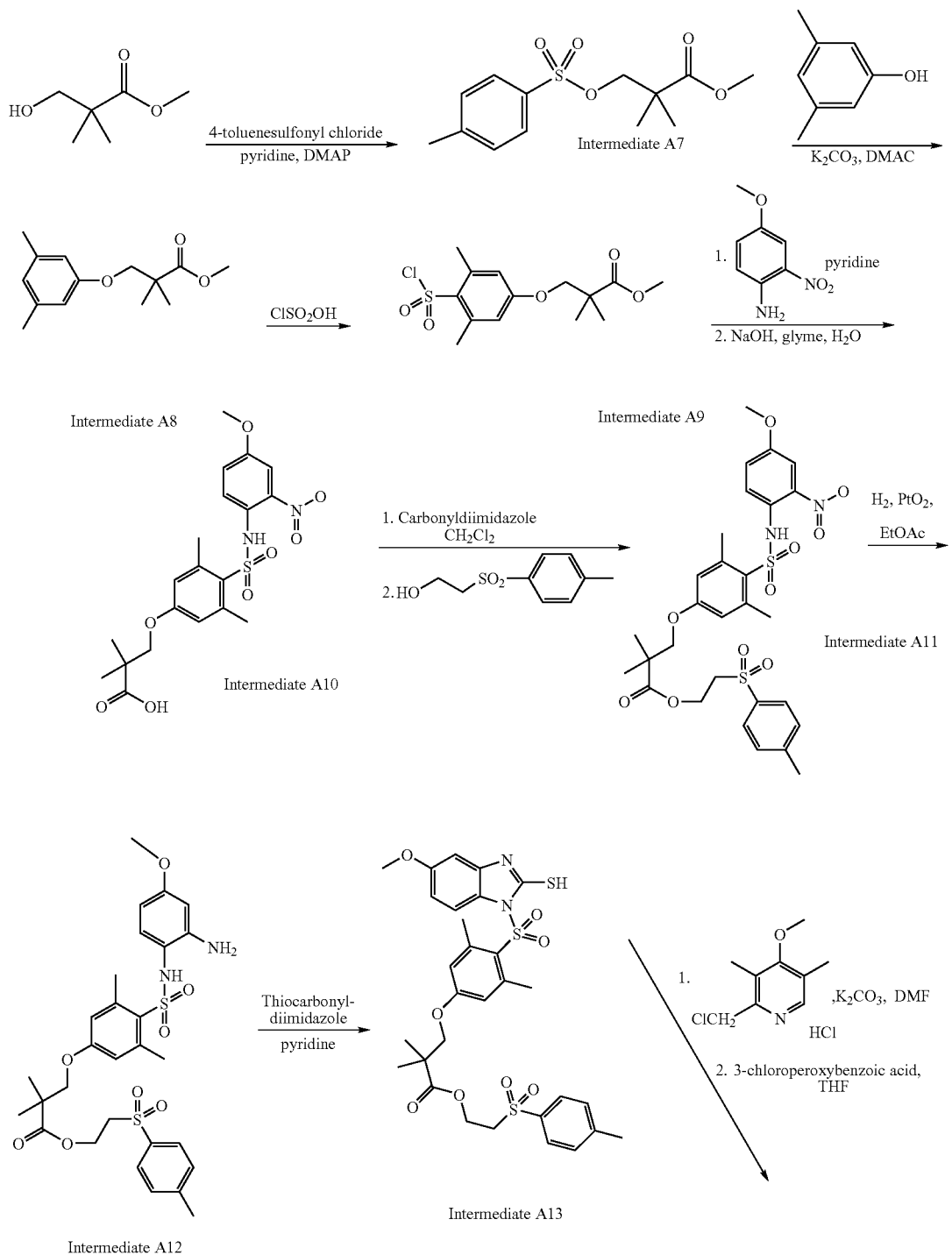

Reaction Scheme 3

-continued

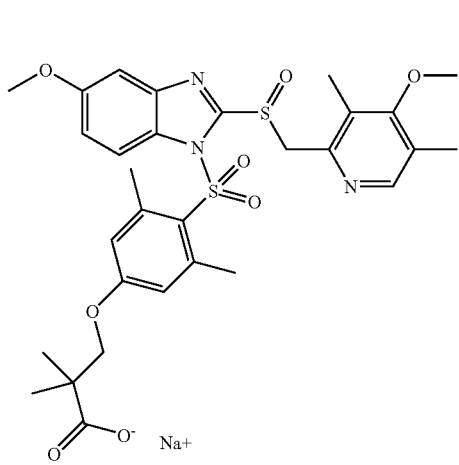

Compound 2

CH₃CN, i-PrOH,
NaHCO₃, H₂O

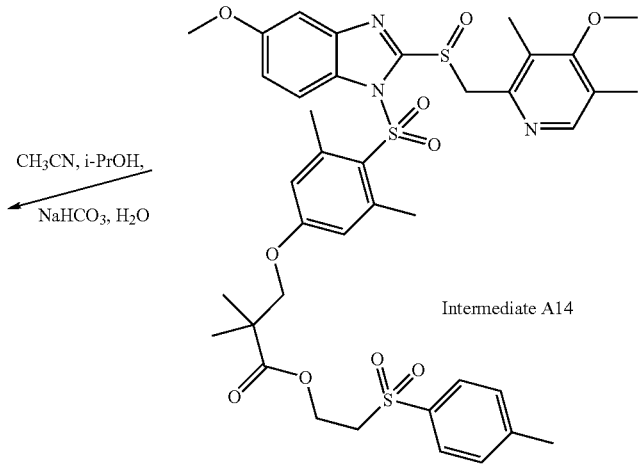

Intermediate A14

Methyl 2,2-dimethyl-3-(4-tolylsulfonyloxy)propionate (Intermediate A7)

A mixture of methyl 2,2-dimethyl-3-hydroxypropionate (100 g, 0.76 mol), 4-toluenesulfonyl chloride (151 g, 0.80 mol), 4-dimethylaminopyridine (4.6 g, 0.038 mol), and pyridine (200 mL) was stirred for 20 hrs and then was diluted with 200 mL toluene, stirred for 30 min and filtered. The filtrate was concentrated to 250 mL at aspirator pressure, diluted with 100 mL toluene, filtered, and concentrated. The residue was suspended in 200 mL hexanes, and the solvent was removed at aspirator pressure to yield the title compound (235 g, 100%) contaminated by a trace of toluenesulfonyl chloride.

Methyl 3-(3,4-dimethylphenyloxy)-2,2-dimethylpropionate (Intermediate A8)

A reaction vessel was charged with methyl 2,2-dimethyl-3-tosyloxypropionate (Intermediate A7, 100 g, 0.35 mol), 3,5-dimethylphenol (45 g, 0.37 mol), potassium carbonate (73 g, 0.53 mol), and dimethylacetamide (300 mL). The mixture was heated on a steam bath for 16 hr and in a 170° C. bath for 6 hr. The cooled reaction mixture was diluted with 1 L water and extracted with 2×200 mL portions of ethyl acetate. The combined organic layers were washed with water, 0.5 M sodium hydroxide (twice), water, and saturated aqueous sodium chloride. The solvent was removed at aspirator pressure and high vacuum. The residue was taken up in dichloromethane and washed with several portions of 1 M sodium hydroxide, water, and saturated sodium chloride. The solution was concentrated, and the residue was distilled at 2 torr to yield 43.5 g (52%) of the title compound.

Methyl 3-(4-chlorosulfonyl-3,5-dimethylphenyloxy)-2,2-dimethylpropionate (Intermediate A9)

Methyl 3-(3,4-dimethylphenyloxy)-2,2-dimethylpropionate (Intermediate A8, 23.6 g, 0.100 mol) was added dropwise over 30 min to rapidly stirred chlorosulfonic acid (46.6 g, 0.400 mol) while the reaction temperature was maintained at −2° C. The reaction mixture was then poured into a stirred mixture of 300 g ice and 300 mL of dichloromethane. The aqueous phase was extracted with additional dichloromethane, and the combined organic layers were washed with water, 0.5 M sodium bicarbonate (X 2), and water. The solvent was removed at aspirator pressure and the residue ethyl acetate in hexanes) to yield 9.6 g (29%) of the title compound.

Methyl 3-{4-[4-methoxy-2-nitrophenylaminosulfonyl]-3,5-dimethylphenoxy]-2,2-dimethylpropionate Methyl 3-(4-chlorosulfonyl-3,5-dimethylphenyloxy)-2,2-dimethylpropionate (Intermediate A9, 8.3 g, 0.025 mol), 3-methoxy-2-nitroaniniline (3.9 g, 0.023 mol), and pyridine (40 mL) were mixed and stirred while immersed in a 100° C. bath for 1.5 hr and for 4 days at room temperature. The mixture was diluted with 150 mL toluene and filtered. The filtrate was concentrated at aspirator pressure, and the residue was partitioned between 1.2 M hydrochloric acid and ethyl acetate. The organic layer was washed with water and concentrated. The foamy residue was stirred with 50 mL 2:1 hexanes:ethyl acetate. The resulting solid was collected and washed with several portions of the same solvent. After drying the product, title compound, weighed 9.1 g (85%)

3-{4-[4-Methoxy-2-nitrophenyl]aminosulfonyl}-3,5-dimethylphenoxy]-2,2-dimethylpropionic Acid (Intermediate A10)

A 54 mL (0.054 mol) portion of 0.100 N sodium hydroxide was added to a dimethoxyethane solution of methyl 3-({4-[4-methoxy-2-nitrophenyl]aminosulfonyl}-3,5-dimethylphenoxy)-2,2-dimethylpropionate (8.5 g, 0.018 mol). After ca. 20 hr, the mixture was diluted with 60 mL of 1.2 M hydrochloric acid and 100 g ice. The resulting suspension was extracted with several portions of ethyl acetate, and the combined organic layers were washed with saturated aqueous sodium chloride and concentrated. The residue was stirred with hexanes for 1 hr and then collected with the aid of additional hexanes to yield 8.2 g (100%) of the title compound.

2-(4-Tolylsulfonyl)ethyl 3-{4-[4-methoxy-2-nitrophenylaminosulfonyl}-3,5-dimethylphenoxy]-2,2-dimethylpropionate (Intermediate A11)

A mixture of 3-{4-[4-methoxy-2-nitrophenylaminosulfonyl}-3,5-dimethylphenoxy]-2,2-dimethylpropionic acid (Intermediate A10, 24.2 g, 0.054 mol) and carbonyldiiuidazole (9.5 g, 0.059 mol) was diluted with 45 mL dichloromethane and warmed in a 36° C. bath for 15 min. Then, 4-tolylsulfonylethanol was added, the bath temperature was raised to 55° C., and the solvent was blown off in a nitrogen stream. After 1.5 hr, the stream was stopped, and after 2.5 hr, the cooled reaction mixture was partitioned between ethyl acetate and 1.2 M hydrochloric acid. The aqueous layer was extracted with additional ethyl acetate, and the combined organic layers were washed with water and saturated sodium chloride, concentrated at aspirator pressure and high vacuum. The product, title compound, (34 g, 99%) was carried on without further purification.

2-(4-Tolylsulfonyl)ethyl 3-({4-[2-amino-4-methoxyphenyl]aminosulfonyl}-3,5-dimethylphenoxy)-2,2-dimethylpropionate (Intermediate A12)

2-(4-Tolylsulfonyl)ethyl 3-{4-[4-methoxy-2-nitrophenylaminosulfonyl}-3,5-dimethylphenoxy]-2,2-dimethylpropionate (Intermediate A11, 34 g, 0.054 mol) was hydrogenated in ethyl acetate using platinum oxide (1.7 g, 0.0075 mol) as catalyst. The product, title compound, was taken on without further purification.

2-(4-Tolylsulfonyl)ethyl 3-(4-[{2-mercapto-5-methoxybenzimidazolyl}sulfonyl]-3,5-dimethylphenoxy)-2,2-dimethylpropionate (Intermediate A13)

2-(4-Tolylsulfonyl)ethyl 3-({4-[2-amino-4-methoxy-phenyl]aminosulfonyl}-3,5-dimethylphenoxy)-2,2-dimethylpropionate (Intermediate A12, 4.1 g, 0.0068 mol) and thiocarbonyldiimidazole (1.8 g, 0.010 mol) were dissolved in pyridine (40 mL). After ca. 16 hr, the mixture was poured into 400 mL of water. The suspension was extracted with several portions of ethyl acetate, and the combined organic layers were washed with 2 portions of 1.2 M hydrochloric acid and concentrated. The residue was reconcentrated from dichloromethane to yield 4.3 g (98%) of the title compound.

2-(4-Tolylsulfonyl)ethyl 3-(4-[(5-methoxy-2-{[(4-methoxy-3,5-dimethyl(2-pyridyl))methylthio}benzimidazolyl)sulfonyl]-3,5-dimethylphenoxy}-2,2-dimethylpropionate 2-(4-Tolylsulfonyl)ethyl 3-(4-[{2-mercapto-5-methoxybenzimidazolyl}sulfonyl]-3,5-dimethylphenoxy)-2,2-dimethylpropionate (Intermediate A13, 4.2 g, 0.0065 mol) and potassium carbonate (1.97 g, 0.014 mol) were mixed in dimethylformamide (41 mL). Then, 2-(chloromethyl)-4-methoxy-3,5-dimethylpyridinium hydrochloride (1.5 g, 0.0068 mol) was added in a single portion. After 90 min, the reaction mixture was poured into a rapidly stirring mixture of 16 mL of 1.2 M hydrochloric acid and 45 g of ice. The resulting oily suspension began to crystallize upon extensive scratching with a glass rod. It was then stirred for several days. The product, title compound, was collected by filtration and washed with several portions of water. After drying, it weighed 4.8 g (93%).

2-(4-Tolylsulfonyl)ethyl 3-{4-[(5-methoxy-2-{[(4-methoxy-3,5-dimethyl(2-pyridyl))methylsulfinyl}benzimidazolyl)sulfonyl]-3,5-dimethylphenoxy}-2,2-dimethylpropionate (Intermediate A14)

2-(4-Tolylsulfonyl)ethyl 3-{4-[(5-methoxy-2-{[(4-methoxy-3,5-dimethyl(2-pyridyl))methylthio}benzimidazolyl)sulfonyl]-3,5-dimethylphenoxy}-2,2-dimethylpropionate (4.63 g, 0.00582 mol) and 70% 3-chloroperoxybenzoic acid (1.8 g, 0.00728 mol) were separately dissolved in 30 mL of tetrahydrofuran and cooled in a freezer for 40 min. The solutions were combined and left in a freezer for 16 hr. The reaction mixture was then poured into a mixture of ethyl acetate and 5% sodium metabisulfite. The organic layer was washed with an additional portion of bisulfite solution, with several portions of 5% sodium bicarbonate solution, and with saturated sodium chloride. After the solvent had been removed in vacuo, the residue was separated by flash chromatography (silica gel: 1:1 hexanes:ethyl acetate→0.5% methanol in ethyl acetate) to yield 1.4 g (30%) of the title compound.

3-{4-[(5-Methoxy-2-{[(4-methoxy-3,5-dimethyl(2-pyridyl))methylsulfinyl}benzimidazolyl)sulfonyl]-3,5-dimethylphenoxy}-2,2-dimethylpropionic acid sodium salt (Compound 2)

2-(4-Tolylsulfonyl)ethyl 3-{4-[(5-methoxy-2-{[(4-methoxy-3,5-dimethyl(2-pyridyl))methyl]sulfinyl}benzimidazolyl)sulfonyl]-3,5-dimethylphenoxy}-2,2-dimethylpropionate (Intermediate A14, 1.4 g, 0.0017 mol), dissolved in acetonitrile (9 mL), was mixed with isopropanol (3 mL) and 3 mL of water containing sodium bicarbonate (0.17 g, 0.0020 mol). The mixture was heated in a 70° C. bath for about 6 hr and was then concentrated at aspirator pressure and then high vacuum. The residue was washed with ethyl acetate, was then precipitated from a dichloromethane/isopropanol solution with ethyl acetate, and finally was concentrated from water at reduced pressure. The residue was redissolved in water and ethyl acetate. The pH was adjusted to 4, and the organic layer was filtered through a sodium sulfate plug and concentrated. After it had dried for several days at high vacuum, this acid was dissolved in dimethoxyethane and neutralized by the addition of a stoichiometric amount of 0.100 N sodium hydroxide. The solvents were removed at aspirator pressure and finally high vacuum, and the residue was collected with the aid of diethyl ether. After it had dried, the product, title compound, weighed 0.71 g (64%).

NMR (300 MHz) (D$_2$O) δ 7.9 (s, 1H); 7.2-6.5 (complex, 5H); 4.9-4.5 (AB, 2H); 3.9 (m, 2H); 3.7 (s, 3H); 3.5 (s, 3H); 2.2 (s, 6H); 2.0 (s, 3H); 1.9 (s, 3H); 1.0 (d, 6H).

Reaction Scheme 4

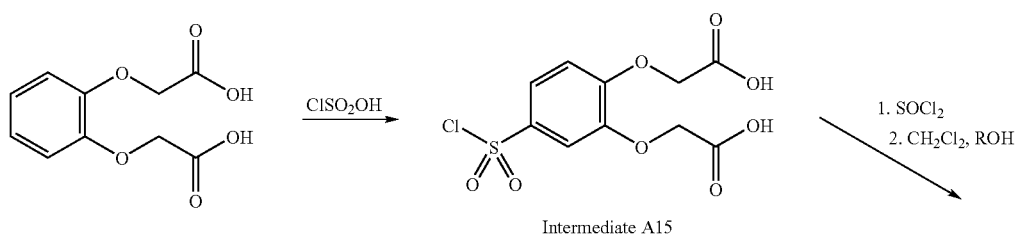

Intermediate A15

-continued
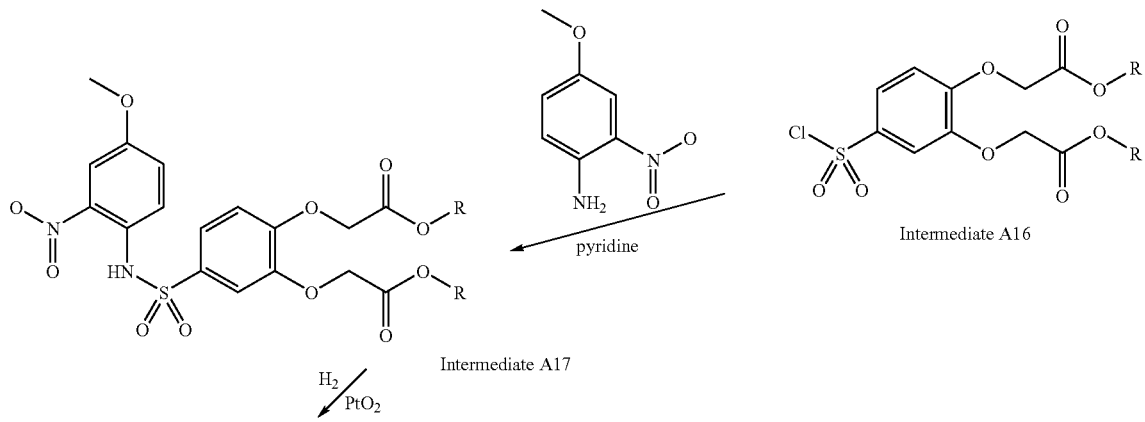
Intermediate A16
Intermediate A17
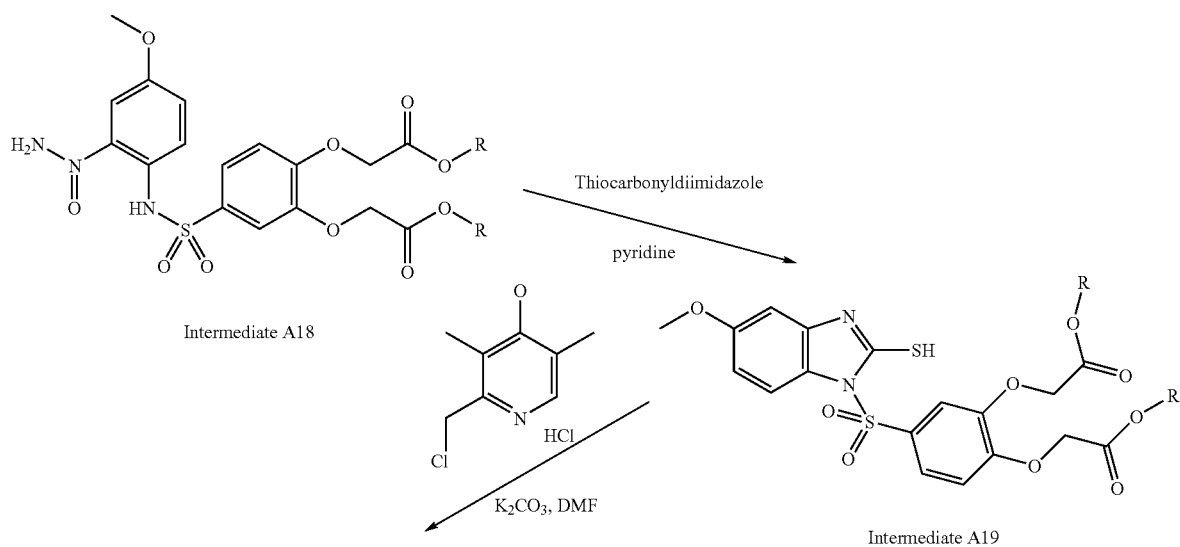
Intermediate A18
Intermediate A19
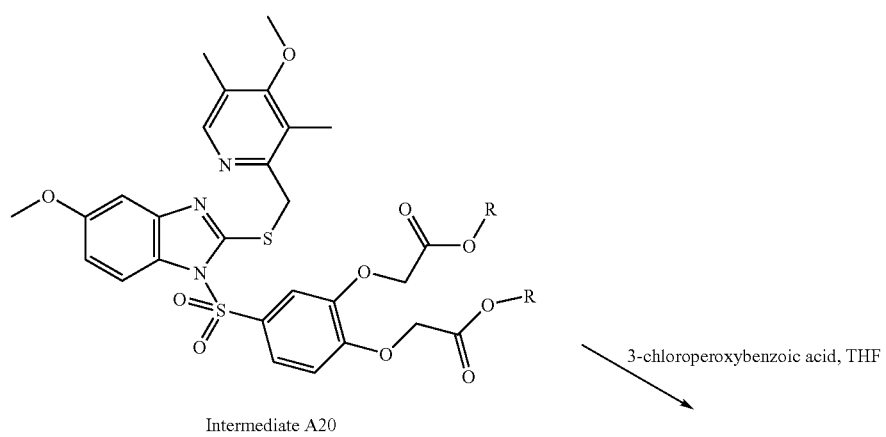
Intermediate A20

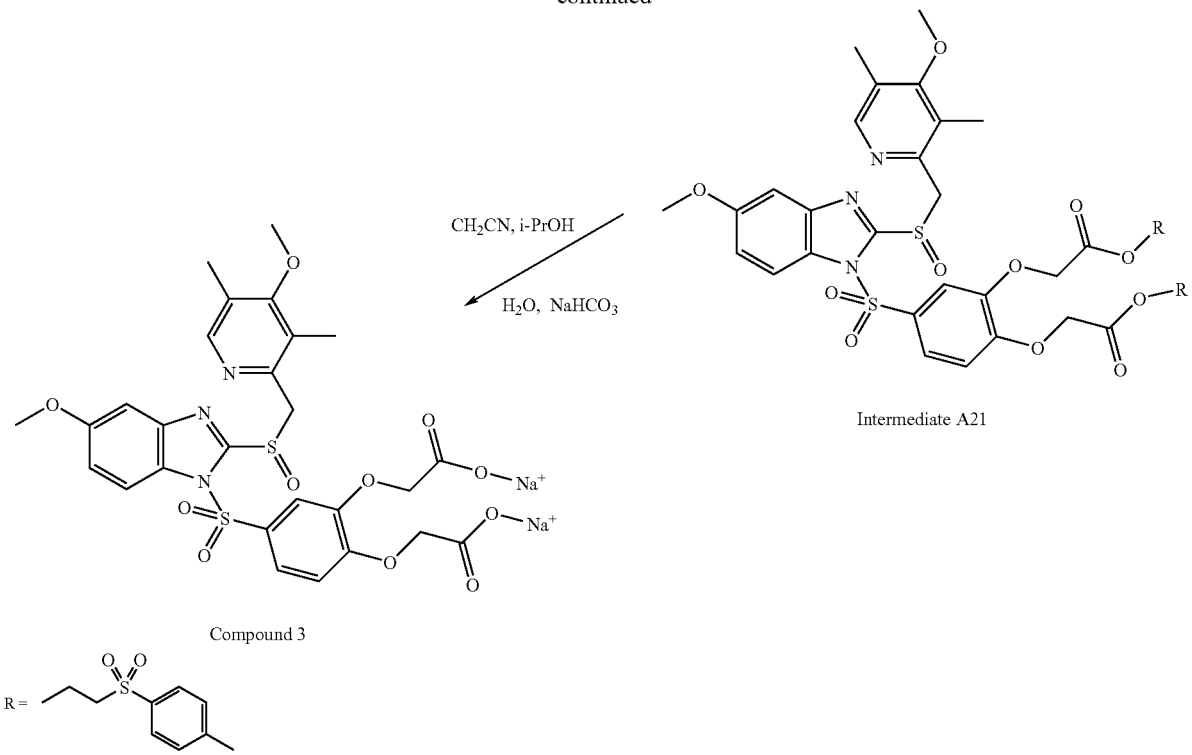

Intermediate A21

Compound 3

2-Carboxymethoxy-4-chlorosulfonylphenoxyacetic acid (Intermediate A15)

2-Carboxymethoxyphenoxyacetic acid (15.3 g, 0.0675 mol) was added in portions over 30 min to stirred chlorosulfonic acid (59.0 g, 0.506 mol) that was cooled in an ice/methanol bath. The mixture was allowed to warm to room temperature over 2.5 hr and was then poured slowly into stirred ice water. The resulting solid was collected by filtration, washed with water, and dried at high vacuum over sodium hydroxide. The product, title compound, weighed 6.54 g (30%).

2(4-Tolylsulfonyl)ethyl 4-chlorosulfonyl-2-(2-[4-tolylsulfonyl]ethoxycarbonylmethoxy)phenoxyacetate (Intermediate A16, also known as Intermediate 36)

2-carboxymethoxy-4-chlorosulfonylphenoxyacetic acid (Intermediate A15, 6.54 g, 0.0202 mol) was heated at reflux with 15 mL (0.202 mol) of thionyl chloride. After 1 hr, the mixture was diluted with 20 mL toluene and concentrated to dryness at aspirator pressure and high vacuum. The crystalline residue was dissolved in 300 mL dichloromethane and mixed with 2-(4-tolylsulfonyl)ethanol (8.89 g, 0.044 mol). Pyridine (3.6 mL, 0.044 mol) in 100 mL dichloromethane was then added dropwise over 15 min. After an additional 1.75 hr, the reaction mixture was washed with 1 M sulfuric acid, dried over magnesium sulfate, and concentrated. The residue was purified on flash silica gel (dichloromethane→7.5% ethyl acetate in dichloromethane) to yield 9.74 g (70%) of the title compound.

2(4-Tolylsulfonyl)ethyl 4-(4-methoxy-2-nitro-phenyl)aminosulfonyl-2-(2-[4-tolylsulfonyl]ethoxycarbonylmethoxy)phenoxyacetate (Intermediate A17)

4-Methoxy-2-nitroaniline (2.3 g, 0.014 mol) and 2-(4-tolylsulfonyl)ethyl 4-chlorosulfonyl-2-(2-[4-tolylsulfonyl]ethoxycarbonylmethoxy)phenoxyacetate (Intermediate A16, 9.6 g, 0.014 mol) were dissolved in 40 mL of pyridine and stirred under positive nitrogen pressure. After ca. 16 hr, the mixture was diluted with 50 mL of toluene and 20 mL of dichloromethane and was concentrated at aspirator pressure. The residue was purified on a flash silica gel column (dichloromethane→5:1 dichloromethane:ethyl acetate) to yield 6.7 g (58%) of the title compound.

2(4-Tolylsulfonyl)ethyl 4-(2-amino-4-methoxy-phenyl)aminosulfonyl-2-(2-[4-tolylsulfonyl]ethoxycarbonylmethoxy)phenoxyacetate (Intermediate A18)

2(4-Tolylsulfonyl)ethyl 4-(4-methoxy-2-nitro-phenyl)aminosulfonyl-2-(2-[4-tolylsulfonyl]ethoxycarbonylmethoxy)phenoxyacetate (Intermediate A17, 6.6 g, 0.0080 mol) was hydrogenated using platinum oxide as catalyst. The mixture was filtered and concentrated. After drying at high vacuum, the residual product, title compound, weighed 5.9 g (93%).

2-(4-Tolylsulfonyl)ethyl 4-[(2-mercapto-5-methoxybenzimidazolyl)sulfonyl]-2-(2-[4-tolylsulfonyl] ethoxycarbonylmethoxy)phenoxyacetate (Intermediate A19)

A mixture of 2-(4-tolylsulfonyl)ethyl 4-(2-amino-4-methoxy-phenyl)aminosulfonyl-2-(2-[4-tolylsulfonyl]ethoxycarbonylmethoxy)phenoxyacetate (Intermediate A18, 5.9 g, 0.0075 mol) and thiocarbonyldiimidazole (2.0 g, 0.011 mol) in 35 mL of pyridine was stirred under nitrogen for 4 hr. The mixture was then poured into 400 mL of rapidly stirring water. This suspension was stirred for ca. 16 hr, and was then extracted with toluene, diethyl ether, dichloromethane (2 portions) and 1:1 dichloromethane:methanol (3 portions). The extracts were washed, combined, and concentrated to yield 5.9 g (96%) of the title compound.

2-(4-Tolylsulfonyl)ethyl 4-[{5-methoxy-([4-methoxy-3,5-dimethyl(2-pyridyl)]methylthio)-benzimidazolyl}sulfonyl]-2-(2-[4-tolylsulfonyl]ethoxycarbonylmethoxy)phenoxyacetate (Intermediate A20)

2-(4-Tolylsulfonyl)ethyl 4-[(2-mercapto-5-methoxybenzimidazolyl)sulfonyl]-2-(2-[4-tolylsulfonyl]ethoxycarbonylmethoxy)phenoxyacetate (Intermediate A19, 5.9 g, 0.0072 mol) was dissolved in 50 mL of dimethylformamide and then mixed with potassium carbonate (2.2 g, 0.016 mol) ($N_2$ atmosphere). Then 2-(chloromethyl)-4-methoxy-3,5-dimethylpyridinium hydrochloride (1.7 g, 0.0076 mol) was added in 1 portion. After about 2.5 hr, the volume of the mixture was reduced to ca. 20 mL at high vacuum (bath temperature <22° C.). The residual solution was poured into a rapidly stirring mixture of 10 mL of 1.2 M hydrochloric acid in 200 mL of water and ice. The suspension was stirred until the precipitate was granular. The solid was then collected and washed with water and allowed to air-dry. The solid was then stirred for 14 hr with 1:1 isopropanol:water. The supernatant was decanted away, and the residue was taken up in dichloromethane and concentrated to dryness. The residue was purified on a flash silica gel column (4% ethyl acetate in dichloromethane→ethyl acetate) yielding 4.8 g (75%) of the title compound.

2-(4-Tolylsulfonyl)ethyl 4-[{5-methoxy-([4-methoxy-3,5-dimethyl(2-pyridyl)]methylsulfinyl)benzimidazolyl}sulfonyl]-2-(2-[4-tolylsulfonyl]ethoxycarbonylmethoxy)phenoxyacetate (Intermediate A21)

2-(4-Tolylsulfonyl)ethyl 4-[{5-methoxy-([4-methoxy-3,5-dimethyl(2-pyridyl)]methylthio)benzimidazolyl}sulfonyl]-2-(2-[4-tolylsulfonyl]ethoxycarbonylmethoxy)phenoxyacetate (Intermediate A20, 4.8 g, 0.0054 mol) was dissolved in 20 mL of tetrahydrofuran, and the solution was left in a freezer for 40 min. A solution of 3-chloroperoxybenzoic acid (1.3 g, 0.0075 mol) in 6 mL of tetrahydrofuran was cooled for 30 min. The two were combined and left in the freezer for 16 hr. The mixture was then poured into a rapidly stirring mixture of 5% aqueous sodium metabisulfite and ethyl acetate. The layers were separated, and the organic layer was washed with 2 portions of 2.5% aqueous sodium bicarbonate and with saturated aqueous sodium chloride. The solution was filtered through 1PS paper and concentrated at aspirator pressure. The residue was separated on a column of flash silica gel (2:1 ethyl acetate:hexanes→ethyl acetate) to yield 2.0 g (41%) of the title compound.

2-Carboxymethoxy-4-[(5-methoxy-2-{[(4-methoxy-3,5-dimethyl(2-pyridyl))methylsulfinyl}benzimidazolyl)sulfonyl]phenoxy}acetic acid di-sodium salt (Compound 3)

2-(4-Tolylsulfonyl)ethyl 4-[{5-methoxy-([4-methoxy-3,5-dimethyl(2-pyridyl)]methylsulfinyl)benzimidazolyl}sulfonyl]-2-(2-[4-tolylsulfonyl]ethoxycarbonylmethoxy)phenoxyacetate (Intermediate A21 2.0 g, 0.0033 mol) was dissolved in 15 mL acetonitrile and 5 mL isopropanol. This solution was mixed with sodium bicarbonate (0.61 g, 0.0072 mol) in 10 mL of water and heated, with stirring, in a 70° C. bath for 75 min. The solvents were removed at aspirator pressure (bath temperature<22° C.), and the residue was left overnight under high vacuum. It was then triturated with 2 portions of diethyl ether and 2 portions of ethyl acetate. The residue was dissolved in water and washed with 3 portions of ethyl acetate. The aqueous solution was then extracted with ethyl acetate at pH 5, 4, 3, and finally at pH 3 with increasing amounts of sodium chloride. The combined organic extracts were concentrated, and the product was collected with the aid of 1:1 dichloromethane:ethyl acetate. The filtrate was combined with similarly derived material and taken through the same neutral and acidic extract procedure. A total of 1.1 g (49% combined yield) of the title compound was obtained.

NMR (300 MHz) ($D_2O$) δ 7.7-6.8 (complex, 7H); 4.7 (AB, 2H), 4.4 (s, 2H); 4.3 (s, 2H); 3.9 (s, 3H); 3.8 (s, 3H); 2.0 (s, 6H).

Reaction Scheme 5

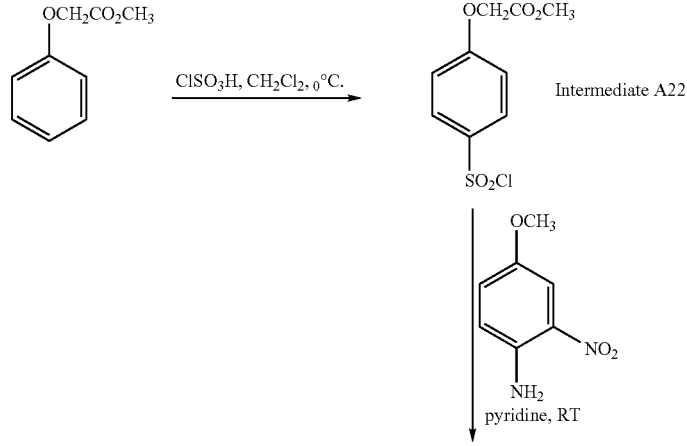

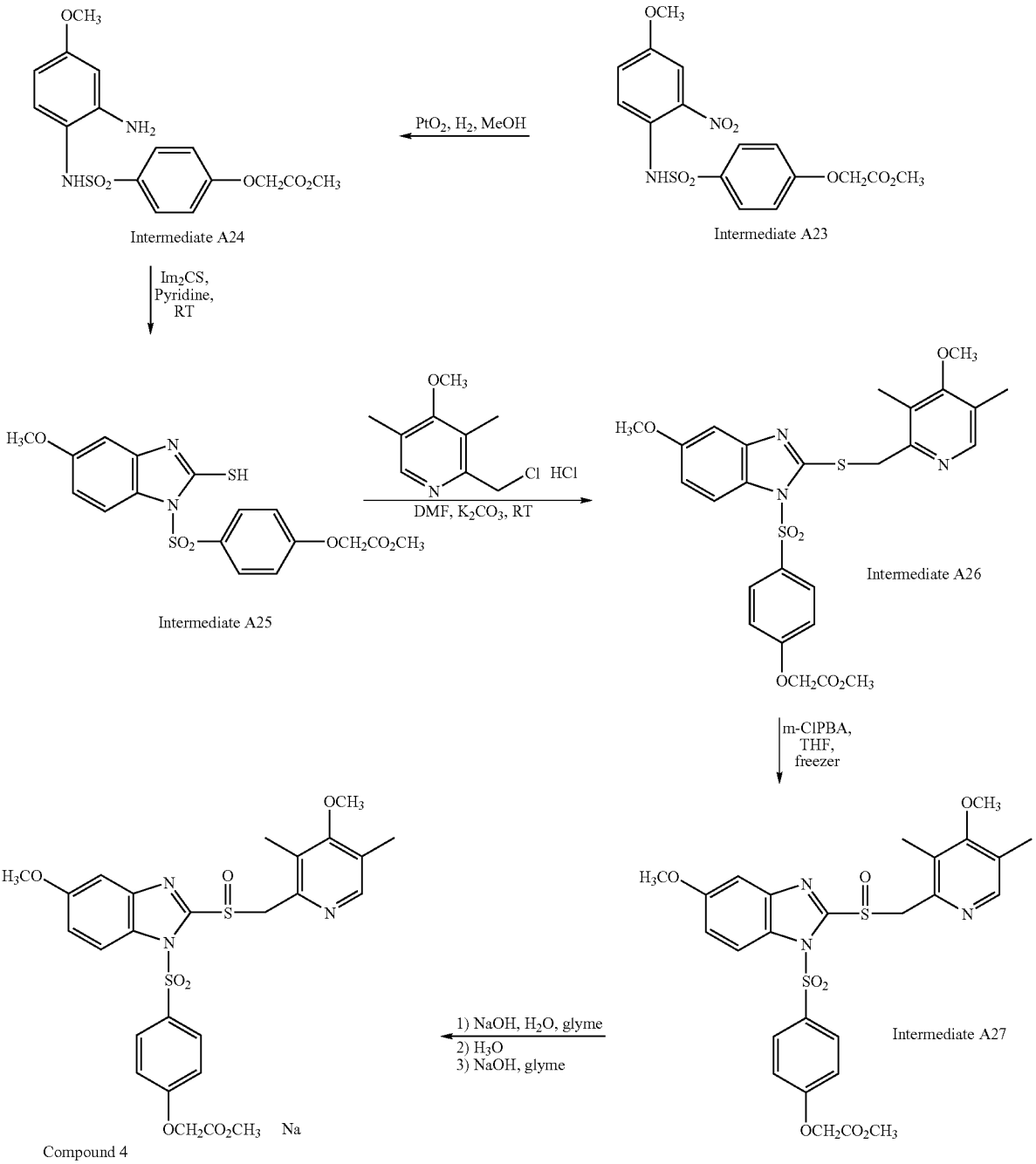

Methyl 2-[4-(chlorosulfonyl)phenoxy]acetate (Intermediate A22)

Methyl phenoxyacetate (99.9 g, 0.6 mol) was added dropwise to chlorosulfonic acid (279.6 g, 159.5 mL, 2.4 mol) at −5° C. at such a rate to maintain internal temperature between 0 to −5° C. (addition took about 60 min). Some solid formed during this addition. The cooling bath was removed and the reaction mixture was stirred at room temperature for an additional 1.5 hr. The reaction mixture was poured into a vigorously stirring mixture of dichloromethane (900 mL) and methanol (100 mL) at 0° C. After 15 min the cooling bath was removed and the resulting mixture was stirred at room temperature for 1 hr. The resulting mixture was washed with ice cold water (2×250 mL). The combined aqueous layers were back extracted with dichloromethane (1×250 mL). The combined organic layers were washed with brine (1×200 mL), dried over anhydrous magnesium sulfate (15 g) and concentrated under reduced pressure to give 132 g (83%) of the title compound as a white solid.

$^1$H NMR (CDCl$_3$ 60 MHz) δ 8.2-7.2 (AB, 4H), 4.95 (s, 2H), 3.95 (s, 3H).

Methyl 2-(3-([4-methoxy-2-nitrophenyl)amino]sulfonyl)phenoxy)Acetate (Intermediate A23)

Solid methyl 2-[4-(chlorosulfonyl)phenoxy]acetate (Intermediate A22, 63.5 g, 0.24 mol) was added to a solution of 4-methoxy-2-nitroaniline (33.6 g, 0.2 mol) in pyridine (1 L) at room temperature under argon. The resulting mixture was stirred at room temperature overnight. The reaction mixture was then concentrated under reduced pressure. The residue was partitioned between 1.5 M hydrochloric acid (1000 mL) and ethyl acetate (500 mL). The aqueous layer was separated and extracted with ethyl acetate (2×250 mL). The combined organic layers were washed with brine (1×200 mL), dried over anhydrous magnesium sulfate (15 g) and concentrated under reduced pressure to give an orange solid. The solid was dissolved in boiling ethyl acetate (500 mL), placed at room temperature for 1 hr and in a freezer for 4 hr. Yellow crystals were collected and air dried to afford 64.2 g (81%) of the title compound.

$^1$H NMR (CDCl$_3$ 60 MHz) δ 9.4 (s, 1H), 7.0-8.0 (m, 7H), 4.8 (s, 2H), 4.0 (s, 3H), 3.95 (s, 3H).

Methyl 2-(3-([2-amino-4-methoxyphenyl)amino]sulfonyl)phenoxy)Acetate (Intermediate A24)

A solution of methyl 2-(3-([4-methoxy-2-nitrophenyl)amino]sulfonyl)phenoxy)acetate (Intermediate A23, 22.57 g, 0.057 mol) in ethyl acetate (500 mL) was slurried with Raney nickel (3 g), filtered, and then hydrogenated over platinum(IV)oxide (0.5 g) until hydrogen uptake ceased. Upon completion the reaction mixture contained some solid product. The solid was collected and air dried to give 15.6 g crude product with 0.5 g catalyst in it. The filtrate was concentrated under reduced pressure to give an additional 3.1 g of product. The total weight of the product, title compound was 18.2 g (87%).

$^1$H NMR (d6-DMSO 60 MHz) δ 6-8.2 (m, 9H), 5.2 (br. s, 3H), 3.9 (s, 3H), 3.7 (s, 3H).

Methyl 2-{4-[(5-methoxy-2-sulfanylbenzimidazolyl)sulfonyl}Acetate (Intermediate A25)

The crude methyl 2-(3-([2-amino-4-methoxyphenyl)amino]sulfonyl)phenoxy)acetate (Intermediate A24, 17.93 g, ca. 0.05 mol) was dissolved in pyridine (200 mL) and filtered through glass fiber filter paper to remove catalyst from the previous preparation. This solution was charged with 1,1'-thiocarbonyldiimidazole (13.1 g, 0.0735 mol) and stirred at room temperature overnight under argon. Water (2.5 L) was then added to the reaction mixture and stirring continued an additional 1.5 hr. The resulting solid was collected, washed with 2 L water and air dried to give 20 g (100%) of the title compound.

$^1$H NMR (d6-DMSO, 60 MHz) δ 7.0-8.8 (m, 8H), 5.1 (s, 2H), 3.9 (s, 3H), 3.8 (s, 3H).

Methyl 2-[4-({5-methoxy-2-[(4-methoxy-3,5-dimethyl(2-pyridyl)methylthio]benzimidazolyl}sulfonyl)phenoxy]acetate (Intermediate A26)

Anhydrous potassium carbonate (14.88 g, 0.108 mol) was ground in a mortar and pestle and added to a solution of methyl 2-{4-[(5-methoxy-2-sulfanylbenzimidazolyl)sulfonyl}acetate (Intermediate A25, 19.99 g, 0.049 mol) in N,N-dimethylformamide (150 mL). Then 2-chloromethyl-3,5-dimethyl-4-methoxypyridine hydrochloride (11.42 g, 0.051 mole) was added to the mixture and vigorously stirred under argon at room temperature. After 2 hr, HPLC analysis showed that the reaction was complete. A mixture of CH$_2$Cl$_2$/IPA (75:25) (800 mL) was added to the reaction mixture, followed by water (400 mL). After stirring for 10 min, the organic layer was separated, washed with water (400 mL) then with brine (400 mL) and dried over anhydrous magnesium sulfate. The solvent was removed on a rotary evaporator under aspirator pressure and finally under high vacuum to give a brown solid. This brown solid was triturated in a mixture of 35% ethyl acetate in hexane (250 mL) and stirred for 1 hr. The solid was collected, washed with a mixture of 35% ethyl acetate in hexane (100 mL) and air dried to give 21 g (77%) of the title compound.

$^1$H NMR (CDCl$_3$ 60 MHz) δ 7.7-8.4 (m, 4H), 6.8-7.3 (m, 4H), 4.85 (s, 2H), 4.8 (s, 2H), 3.9 (s, 3H), 3.85 (s, 6H), 2.4 (s, 3H), 2.3 (s, 3H).

Methyl 2-{4-[(5-methoxy-2-{[(4-methoxy-3,5-dimethyl(2-pyridyl))methyl]sulfinyl}benzimidazolyl)sulfonyl]phenoxy}acetate (Intermediate A27)

A solution of 3-chloroperoxybenzoic acid (12.64 g of 70%, 0.051 mol) in THF (150 mL) was added to a cold solution of the sulfide (Intermediate A26, 22.84 g, 0.041 mol) in THF (500 mL). The resulting mixture was kept in a freezer overnight (19 hr). HPLC analysis showed 58% sulfoxide methyl ester, 6% unreacted starting sulfide, and two other unidentified impurities (8% and 24%). The reaction mixture was diluted with ethyl acetate (750 mL) and washed with: 5% sodium metabisulfite (2×200 mL), 5% sodium bicarbonate (2×200 mL), and brine (2×200 mL). The resulting solution was filtered through 1 PS filter paper and concentrated under reduced pressure to give 26 g of a foam. The foam was purified by flash chromatography (silica gel, ethyl acetate to 1% MeOH/ethyl acetate) to give 16.2 g of the crude product as a foam. This foam was triturated with 10% ethyl acetate/hexane (100 mL). The white solid was collected and air dried to give 15.25 g (65%) of the the title compound, $^1$H NMR (CDCl$_3$ 60 MHz) δ 8.0-8.7 (m, 4H), 7.7-7.3 (m, 4H), 5.2 (unresolved d, 4H), 3.95 (s, 3H), 3.8 (s, 3H), 3.75 (s, 3H), 2.4 (s, 3H), 2.2 (s, 3H).

2-{4-[(5-Methoxy-2-{[(4-methoxy-3,5-dimethyl(2-pyridyl))methyl]sulfonyl}benzimidazolyl)sulfonyl]phenoxy}acetic acid A 3L 3-necked flask equipped with a mechanical stirrer was charged with methyl 2-{4-[(5-methoxy-2-{[(4-methoxy-3,5-dimethyl(2-pyridyl))methyl]sulfonyl}benzimidazolyl)sulfonyl]phenoxy}acetate (Intermediate A27, 13.75 g, 0.024 mol) in glyme (1200 mL). To this vigorously stirring solution was added 0.1 N NaOH solution (300 mL). The resulting mixture was concentrated under reduced pressure at 47° C. The residue was triturated with fresh ethyl acetate (100 mL) for a total of four times. The residue was placed under high vacuum for 1 hr to give 17 g of a gummy solid. In a 1L 3-necked flask equipped with a mechanical stirrer was placed 16 g of this solid (equivalent to 13.3 g sodium salt, 0.0226 mol) in water (250 mL). The solution was washed by stirring with ethyl acetate (250 mL) for 1 hr and then the layers were separated. HPLC analysis of the ethyl acetate layer showed 64% omeprazole and 33% unreacted sulfoxide methyl ester. A fresh 250 mL of ethyl acetate was added to the aqueous layer. The resulting mixture was stirred and acidified to pH 3-4 with ca. 40 mL of 0.5 N hydrochloric acid. The ethyl acetate layer was separated quickly, because product started to crystallize, and placed in a freezer overnight. The crystals were collected and air dried to give 6.7 g (53%) of the methyl 2-{4-[(5-methoxy-2-{[(4-methoxy-3,5-dimethyl(2-pyridyl))methyl]sulfonyl}benzimidazolyl)sulfonyl]phenoxy}acetate.

Sodium Salt of 2-{4-[(5-methoxy-2-{[(4-methoxy-3,5-dimethyl(2-pyridyl))methyl]sulfonyl}benzimidazolyl)sulfonyl]phenoxy}acetic acid (Compound 4)

The sulfoxide acid (4.81 g, 0.0086 mol) was suspended in glyme (500 mL). The resulting mixture was stirred with a magnetic stir-bar and 1 N sodium hydroxide (8.6 mL, 0.0086 mol) was added over 20 min. Insoluble material was filtered and the filtrate concentrated in vacuo to give a tan solid. This solid was suspended in ethyl acetate (100 mL) and stirred for 1 hr. The solid was collected and air dried to give 4.1 g of the title compound.

$^1$H NMR (CDCl3, d6-DMSO, 60 MHz) δ 6.9-8.2 (m, 8H), 4.7-5.1 (dd, 2H), 4.3 (s, 2H), 3.8 (s, 3H), 3.7 (s, 3H), 2.25 (s, 3H), 2.15 (s, 3H).

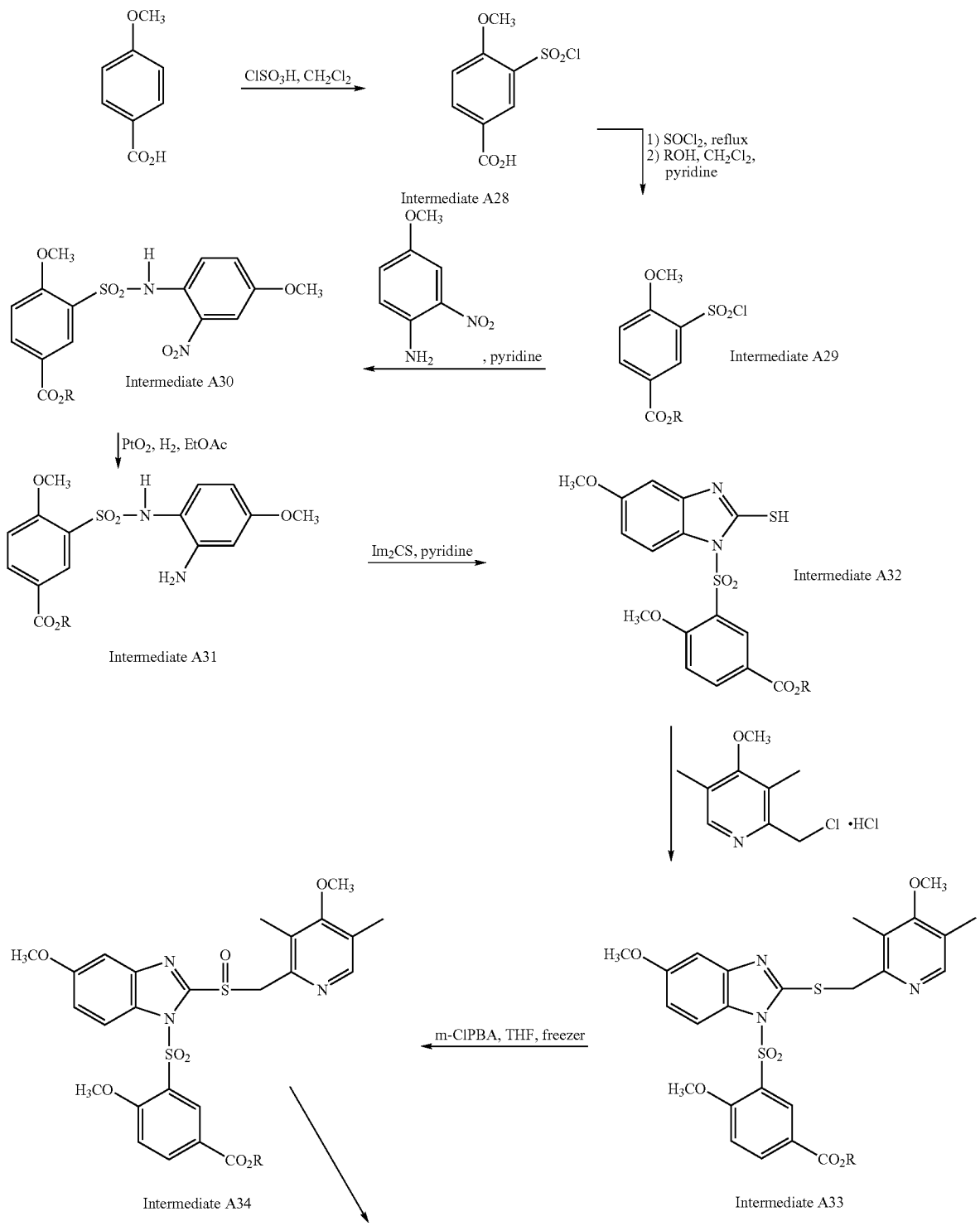

Reaction Scheme 6

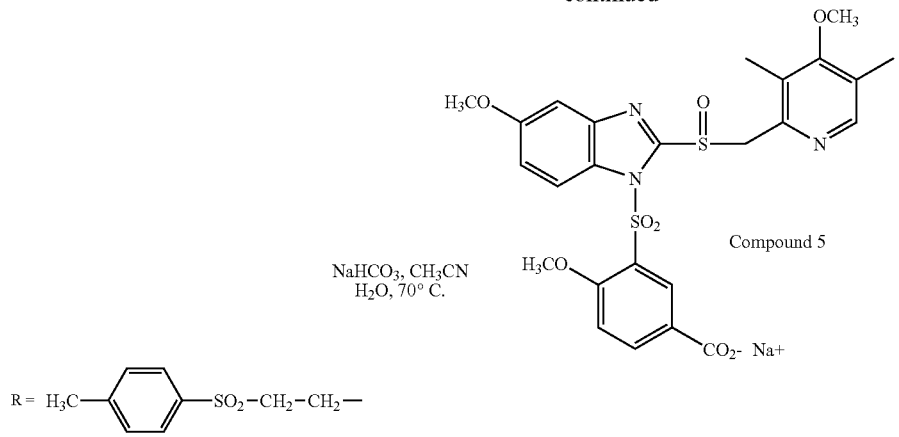

3-(Chlorosulfonyl)-4-methoxybenzoic acid (Intermediate A28)

Solid 4-methoxy benzoic acid (45.6 g, 0.3 mol), in portions, was added to chlorosulfonic acid (139.8 g, 80 mL, 1.2 mol) at room temperature. After most of the bubbling had ceased, the reaction mixture was heated to 80° C. for 1 hr. The reaction mixture was then poured into vigorously stirring crushed-ice (500 g) and water was then added (500 mL). After 30 min, the white solid was collected, washed with water (2 L) and dried to give 50 g (66%) of the title compound.

2-(4-Methylphenylsulfonyl)ethyl 3-(chlorosulfonyl)-4-methoxybenzoate (Intermediate A29)

A mixture of 3-(chlorosulfonyl)-4-methoxybenzoic acid (Intermediate A28, 13.78 g, 0.055 mol) and thionyl chloride (39.27 g, 25 mL, 0.33 mol) was refluxed for 1 hr. Excess thionyl chloride was distilled off at atmospheric pressure and finally at reduced pressure to give 15 g acid chloride as a light brown solid. To a mixture of acid chloride (15 g) and 2-(p-tolylsulfonyl)ethanol (10.46 g, 0.0522 mol) in dichloromethane (100 mL) was added triethylamine (5.56 g, 0.055 mol) at room temperature. TLC (ethyl acetate) showed the reaction mixture was complete after 1 hr. The reaction mixture was washed with water (2×100 mL) and brine (1×100 mL), filtered through 1PS filter paper and concentrated under reduced pressure to give an oil. The oil was triturated with 15% ethyl acetate in hexane (100 mL) and solid was collected and dried to give 19.4 g, (81%) of the, title compound, sulfonyl chloride ester as a white solid.

2-(4-Methylphenylsulfonyl)ethyl 4-methoxy-3-(4-methoxy-2-nitrophenylaminosulfonyl)benzoate (Intermediate A30)

The sulfonyl chloride (Intermediate A29, 18.17 g, 0.042 mol), 3-methoxy-2-nitroaniniline (7.06 g, 0.042 mol), and pyridine (100 mL) were mixed and stirred at room temperature overnight under argon. The reaction mixture was concentrated under reduced pressure. The residue was dissolved in ethyl acetate (250 mL), washed with 3 M hydrochloric acid (3×100 mL) and brine,(1×100 mL), filtered through 1PS filter paper and concentrated under reduced pressure to give an orange-red oil. The oil was purified by flash chromatography (silica gel, 20% ethyl acetate in hexane to 50% ethyl acetate in hexane) to give 13.8 g (57%) of the title compound, nitro sulfonamide as a foam.

2-(4-Methylphenylsulfonyl)ethyl 3-{[(2-amino-4-methoxyphenyl)amino]sulfonyl}-4-methoxybenzoate (Intermediate A31)

A solution of nitro sulfonamide (Intermediate A30, 13.54 g, 0.024 mol) in ethyl acetate (400 mL) was stirred for 15 min with Raney nickel (3 g), filtered through a pad of celite, and hydrogenated over platinum(IV)oxide (1 g) overnight. The reaction mixture was filtered through glass fiber filter paper and concentrated under reduced pressure to give 11.8 g (92%) of the title compound, amine as a foam.

2-[(4-Methylphenyl)sulfonyl]ethyl 4-methoxy-3-[(5-methoxy-2-mercaptobenzimidazolyl)sulfonyl]benzoate (Intermediate A32)

To a solution of the amine (Intermediate A31, 11.75 g, 0.022 mol) in pyridine (150 mL) was added 1,1'-thiocarbonyldiimidazole (5.88 g, 0.033 mol). The reaction mixture was stirred at room temperature for 2 hr and then water added (600 mL). After stirring for 1.5 hr, the solid was collected, washed with water (1 L), and dried to give 10.4 g (82%) of the title compound, thiol.

2-(4-Methylphenylsulfonyl)ethyl 4-methoxy-3-({5-methoxy-2-[(4-methoxy-3,5-dimethyl(2-pyridyl))methylthio]benzimidazolyl}sulfonyl)benzoate (Intermediate A33)

Anhydrous potassium carbonate (5.38 g, 0.039 mol) was ground in a mortar and pestle and added to a solution of the thiol (Intermediate A32, 10.2 g, 0.0177 mol) in N,N-dimethylformamide (100 mL). To this mixture 2-chloromethyl-3,5-dimethyl-4-methoxypyridine hydrochloride (4.13 g, 0.186 mol) was added. After 2 hr 150 mL of 25% isopropyl alcohol in dichloromethane was added to the reaction. The reaction was washed with water (2×75 mL) and brine (1×75 mL), filtered through 1PS filter paper and concentrated under reduced pressure to give a brown oil. The oil was purified by flash chromatography (silica gel, 40% ethyl acetate in hexane to ethyl acetate) to give 11 g (96%) of the title compound, sulfide as a foam.

2-(4-Methylphenylsulfonyl)ethyl 4-methoxy-3-[(5-methoxy-2-{[(4-methoxy-3,5-dimethyl(2-pyridyl))methyl]sulfinyl}benzimidazolyl)sulfonyl]benzoate (Intermediate A34)

The sulfide (Intermediate A33, 10.77 g, 0.0166 mol) was dissolved in tetrahydrofuran (200 mL), and stored in a freezer for 1 hr. Following addition of a cold solution of m-chloroperoxybenzoic acid (5.1 g of 70%, 0.0207 mol) in tetrahydrofuran (100 mL), the reaction mixture was returned to the freezer and stored overnight. The reaction mixture was diluted with ethyl acetate (300 mL) and washed with: 5% sodium metabisulfite (3×100 mL), saturated sodium bicarbonate (2×100 mL) and brine (1×100 mL). The organic phase was filtered through 1PS filter paper, and concentrated under reduced pressure. The concentrate was purified by flash chromatography (silica gel, 50% ethyl acetate in hexane to 4% methanol in ethyl acetate), to give 5.7 g (52%) of the title compound, sulfoxide as a foam.

4-Methoxy-3-[(5-methoxy-2-{[(4-methoxy-3,5-dimethyl(2-pyridyl))methyl]sulfinyl}benzimidazolyl)sulfonyl]benzoic acid sodium salt (Compound 5)

To a solution of the sulfoxide (Intermediate A34, 5.52 g, 0.0083 mol) in a mixture of acetonitrile (45 mL), isopropyl alcohol (15 mL), water (30 mL) was added sodium bicarbonate (0.837 g, 0.00996 mol). The resulting mixture was heated at 78° C. for 45 min. The resulting mixture was concentrated under reduced pressure to give a foam. The foam was triturated with 2% methanol in dichloromethane and gave 4.5 g of a solid. The solid was dissolved in water (150 mL), a mixture of 4% methanol in chloroform (100 mL) was then added and acidified with 3 M hydrochloric acid (3 mL). The aqueous layer was extracted with 4% methanol in chloroform (2×100 mL). The combined organic layers were washed with water (1×100 mL) and concentrated under reduced pressure to a constant weight to give 3.6 g of a foam. The foam was dissolved in glyme (100 mL) and 0.2 N sodium hydroxide (7.45 mL) was added. The resulting mixture was concentrated under reduced pressure and triturated with ether (50 mL) to give 2.45 g of a solid after drying. The solid was dissolved in hot dichloromethane, hot filtered and concentrated under reduced pressure to give 1.8 g (43%) of the title compound $^1$H NMR (300 MHz) δ 9.15 (s, 1H), 8.55 (s, 1H), 8.25 (dd, 1H), 7.45-7.25 (m, 2H), 6.9 (m, 2H), 5.05 (q, 2H), 3.9 (s, 3H), 3.85 (s, 3H), 3.8 (s, 3H), 2.45 (s, 3H), 2.35 (s, 3H).

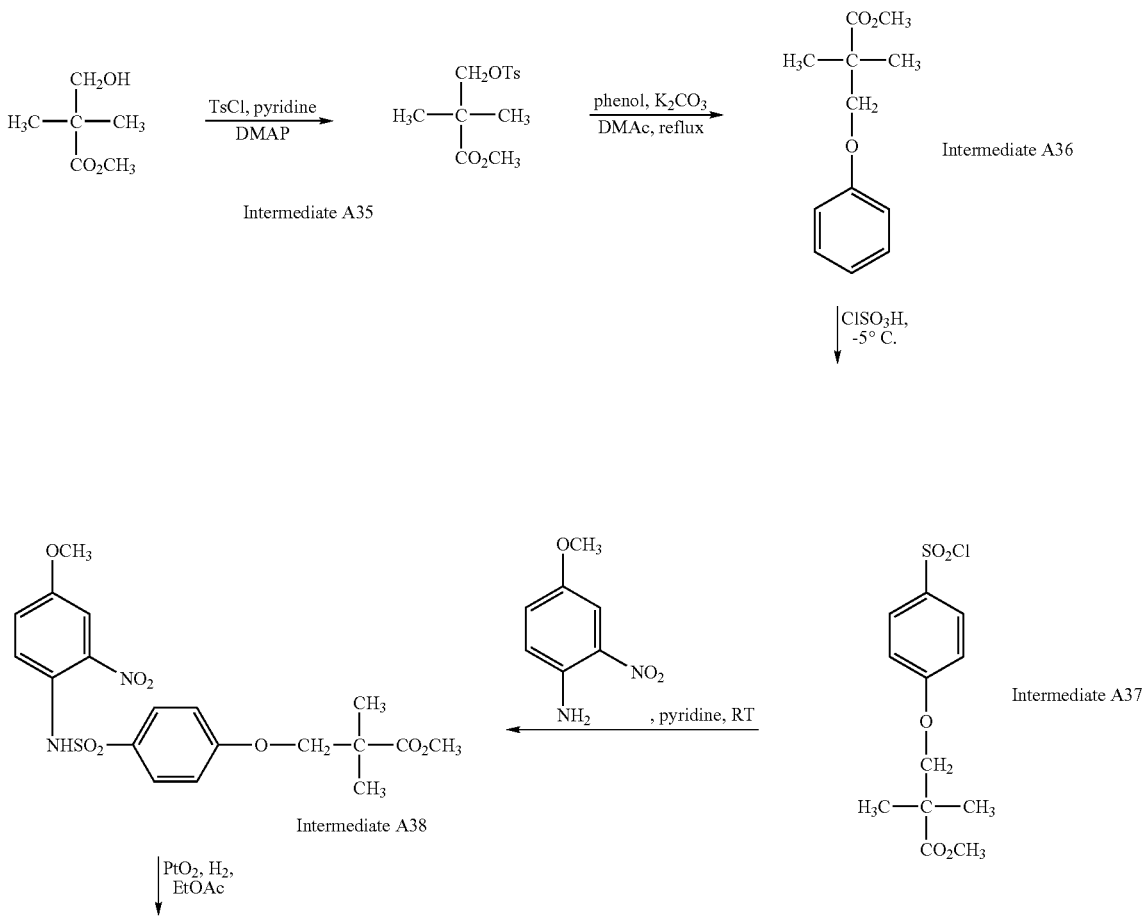

Reaction Scheme 7

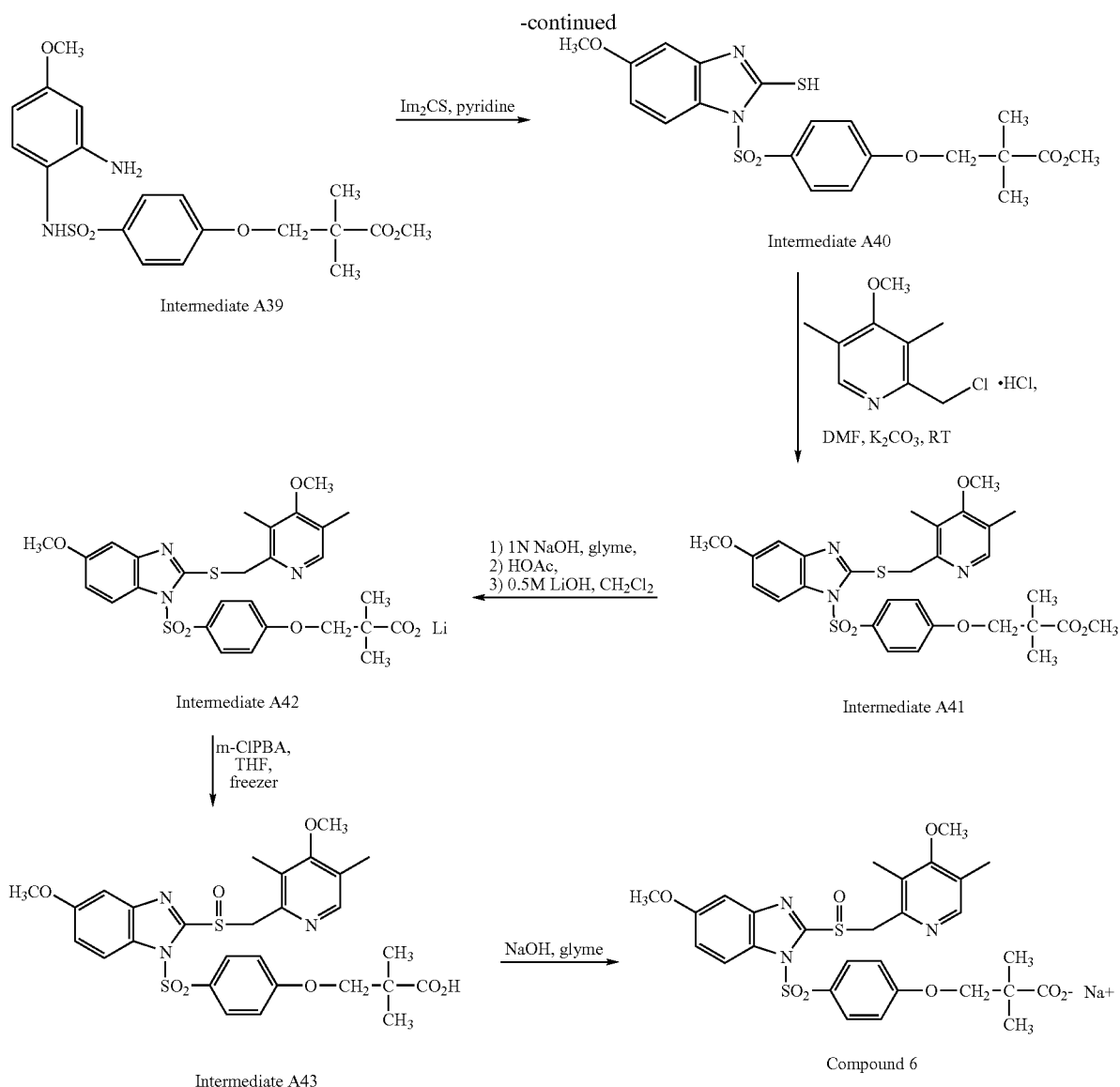

Intermediate A39

Intermediate A40

Intermediate A41

Intermediate A42

Intermediate A43

Compound 6

Methyl 2,2-dimethyl-3-(tolylsulfonyloxy)propionate
(Intermediate A35)

A mixture of methyl 2,2-dimethyl-3-hydroxypropionate (100 g, 0.76 mol), 4-toluenesulfonyl chloride (151 g, 0.80 mol), 4-dimethylaminopyridine (4.6 g, 0.038 mol), and pyridine (200 mL) was stirred for 20 hrs and then was diluted with 200 mL toluene, stirred for 30 min, and filtered. The filtrate was concentrated to 250 mL under reduced pressure, diluted with 100 mL toluene, filtered, and concentrated. The residue was suspended in 200 mL hexanes, and the solvent was removed under reduced pressure to yield the title compound, desired product (235 g, 100%) contaminated by a trace of 4-toluenesulfonyl chloride.

Methyl 2,2-dimethyl-3-phenoxypropionate
(Intermediate A36)

A mixture of methyl 2,2-dimethyl-3-(4-toluenesulfonyloxy)propionate (Intermediate A35, 80 g, 0.28 mol), phenol (28 g, 0.029 mol), potassium carbonate (58 g, 0.42 mol), and 250 mL N,N-dimethylacetamide was stirred and heated at reflux for 4 hr. The reaction mixture was cooled, diluted with ethyl acetate, and poured into water. The organic phase was washed with water and concentrated under reduced pressure. The residue was dissolved in hexanes and washed with water, 1 M sodium hydroxide, and a second portion of water. The concentrated solution was distilled at 15 torr (34-37° C.) to yield 25 g (42%) of the methyl 2,2-dimethyl-3-phenoxypropionate.

Methyl
3-(4-chlorosulfonylphenoxy)-2,2-dimethylpropanoate
(Intermediate A37)

Methyl 2,2-dimethyl-3-phenoxypropionate (Intermediate A36, 36 g, 0.17 mol) was added dropwise over 60 min to rapidly stirred chlorosulfonic acid that was maintained at −5° C. The mixture was warmed to room temperature, stirred for an additional 90 min, and poured into a cooled, rapidly stirring mixture of dichloromethane (250 mL) and methanol (30 mL). The mixture was stirred for 30 min while being cooled and then for 60 min at room temperature. It was then washed with several portions of ice-water. The combined aqueous layers were extracted with a small portion of dichloromethane. The combined organic layers were washed with saturated aqueous sodium chloride and dried over sodium sulfate. The solvent was distilled off under reduced pressure, and the residue was stirred with hexanes and collected by filtration to yield 19 g (36%) of the title compound, sulfonyl chloride.

Methyl 3-(4-(4-methoxy-2-nitrophenylaminosulfonyl)phenoxy)-2,2-dimethylpropanoate (Intermediate A38)

Sulfonyl chloride (Intermediate A37, 18.4 g, 0.06 mol), 3-methoxy-2-nitroaniniline (8.4 g, 0.05 mol), and pyridine (500 mL) were mixed and stirred at room temperature overnight under argon. The reaction mixture was concentrated under reduced pressure, and the residue was partitioned between 1.5 M hydrochloric acid (300 mL) and ethyl acetate (300 mL). The aqueous layer was separated and extracted with ethyl acetate (2×150 mL). The combined organic layers were washed with brine (2×150 mL), dried over anhydrous magnesium sulfate and concentrated under reduced pressure to give an orange oily residue. The oil was purified by flash chromatography (silica gel, hexane to 35% ethyl acetate in hexane) to give 20.8 g (95%) of the title compound, nitro-sulfonamide as a creamy oil.

Methyl 3-(4-{[(2-amino-4-methoxyphenyl)amino]sulfonyl}phenoxy)-2,2-dimethylpropanoate (Intermediate A39)

A solution of nitro sulfonamide (Intermediate A38 20.6 g, 0.047 mol) in ethyl acetate (300 mL) was stirred for 15 min with Raney nickel (1.5 g), filtered through a pad of celite, and hydrogenated over platinum(IV)oxide (0.5 g) overnight. The reaction mixture was filtered through glass fiber filter paper and concentrated under reduced pressure to give 16.3 g (85%) of the title compound, amine as a foam.

Methyl 3-{4-[(5-methoxy-2-mercaptobenzimidazolyl)sulfonyl]phenoxy}-2,2-dimethylpropanoate (Intermediate A40)

To a solution of amine (Intermediate A39, 16.1 g, 0.0395 mol) in pyridine (200 mL) was added 1,1'-thiocarbonyldiimidazole (10.56 g, 0.0592 mol). The reaction mixture was stirred at room temperature overnight and then water was added (2.5 L). After stirring for 1 hr, the solid was collected, washed with water (3 L), and dried to give 16.5 g (93%) of the title compound, thiol as a tan solid.

Methyl 3-(4-{[5-methoxy-2-(4-methoxy-3,5-dimethyl-2-pridylmethylthio)benzimidazolyl]sulfonyl}phenoxy)-2,2-dimethylpropanoate (Intermediate A41)

To a solution of thiol (Intermediate A40, 16.2 g, 0.036 mol) in N,N-dimethylformamide (150 mL) was added potassium carbonate (10.93 g, 0.079 mol). Solid 2-chloromethyl-3,5-dimethyl-4-methoxypyridine hydrochloride (8.39 g, 0.0378 mol) was added to this mixture. After 1 hr a mixture of 800 mL of 25% isopropyl alcohol in dichloromethane was added to the reaction. The reaction was then washed with water (2×400 mL). The combined aqueous layers were back extracted with 100 mL of 25% isopropyl alcohol in dichloromethane. The combined organic layers were washed with brine (1×400 mL), dried over anhydrous magnesium sulfate (20 g) and concentrated under reduced pressure to give an oil. The oil solidified on standing and was triturated with 25% ethyl acetate in hexane (200 mL). The product, title compound (sulfide) was collected and dried to (20.2 g (93%)).

3-[4-({5-Methoxy-2-(4-methoxy-3,5-dimethyl-2-pyridylmethylsulfinyl)benzimidazolyl}sulfonyl)phenoxy]-2,2-dimethylpropanoic acid lithium salt (Intermediate A42)

To a solution of sulfide (Intermediate A41, 9.58 g, 0.016 mol) in glyme (800 mL) was added 1 N sodium hydroxide solution (240 mL) over 30 min. After 3.5 hr, acetic acid (28.8 g) was added to get a pH of about 6.5. Most of the glyme was removed under reduced pressure. Water (250 mL) was added to the residue and the mixture was extracted with dichloromethane (2×125 mL). The combined organic layers were washed with water (1×100 mL) and brine (1×100 mL), filtered through 1PS filter paper and concentrated under reduced pressure. To a solution of residue (10 g) in dichloromethane was added 0.5 M lithium hydroxide solution (100 mL) followed by addition of brine (100 mL). The resulting mixture was stirred for 30 min and solid was collected, washed with water (50 mL) and dried to give 4.1 g (43%) lithium salt of the title compound, sulfide.

3-[4-({5-Methoxy-2-(4-methoxy-3,5-dimethyl-2-pyridylmethylsulfinyl)benzimidazolyl}sulfonyl)phenoxy]-2,2-dimethylpropanoic acid (Intermediate A43)

Lithium salt of sulfide (Intermediate A42, 4.02 g, 0.0068 mol) was dissolved in tetrahydrofuran (250 mL) and cooled in a freezer for 1 hr. 3-Chloroperoxybenzoic acid (5.03 g, 0.0204 mol) was added and the resulting mixture was returned to the freezer and stored overnight. The reaction mixture was diluted with ethyl acetate (600 mL), washed with 5% sodium meta-bisulfite (3×150 mL), water (2×150 mL), brine (2×150 mL), filtered through 1PS filter paper and concentrated under reduced pressure to give a solid residue. The solid was purified by flash chromatography (silica gel, ethyl acetate) to give 1.3 g (29%) of the title compound, sulfoxide as a foam.

3-{4-[(5-Methoxy-2-{[(4-methoxy-3,5-dimethyl(2-pyridyl))methyl]sulfinyl}benzimidazolyl)sulfonyl]phenoxy}-2,2-dimethylpropanoic acid sodium salt (Compound 6)

1 N sodium hydroxide (2 mL) was added to a solution of sulfoxide (Intermediate A43, 1.2 g, 0.002 mol) in glyme (25 mL). The resulting mixture was concentrated under reduced pressure to give a solid residue. The solid residue was triturated-with ethyl acetate (25 mL). The product was collected and dried to give 1.05 g (85%) of the title compound as an off-white solid.

$^1$H NMR (300 MHz) (d$_6$-DMSO) δ 8.1-7.9 (AB, 4H), 7.35 (d, 1H), 7.25 (3d, 3H), 5.1-4.8 (AB, 2H), 3.9 (s, 2H), 3.8 (s, 3H), 3.7 (s, 3H), 2.25 (s, 3H), 2.15 (s, 3H), 1.1 (s, 6H).

Reaction Scheme 8
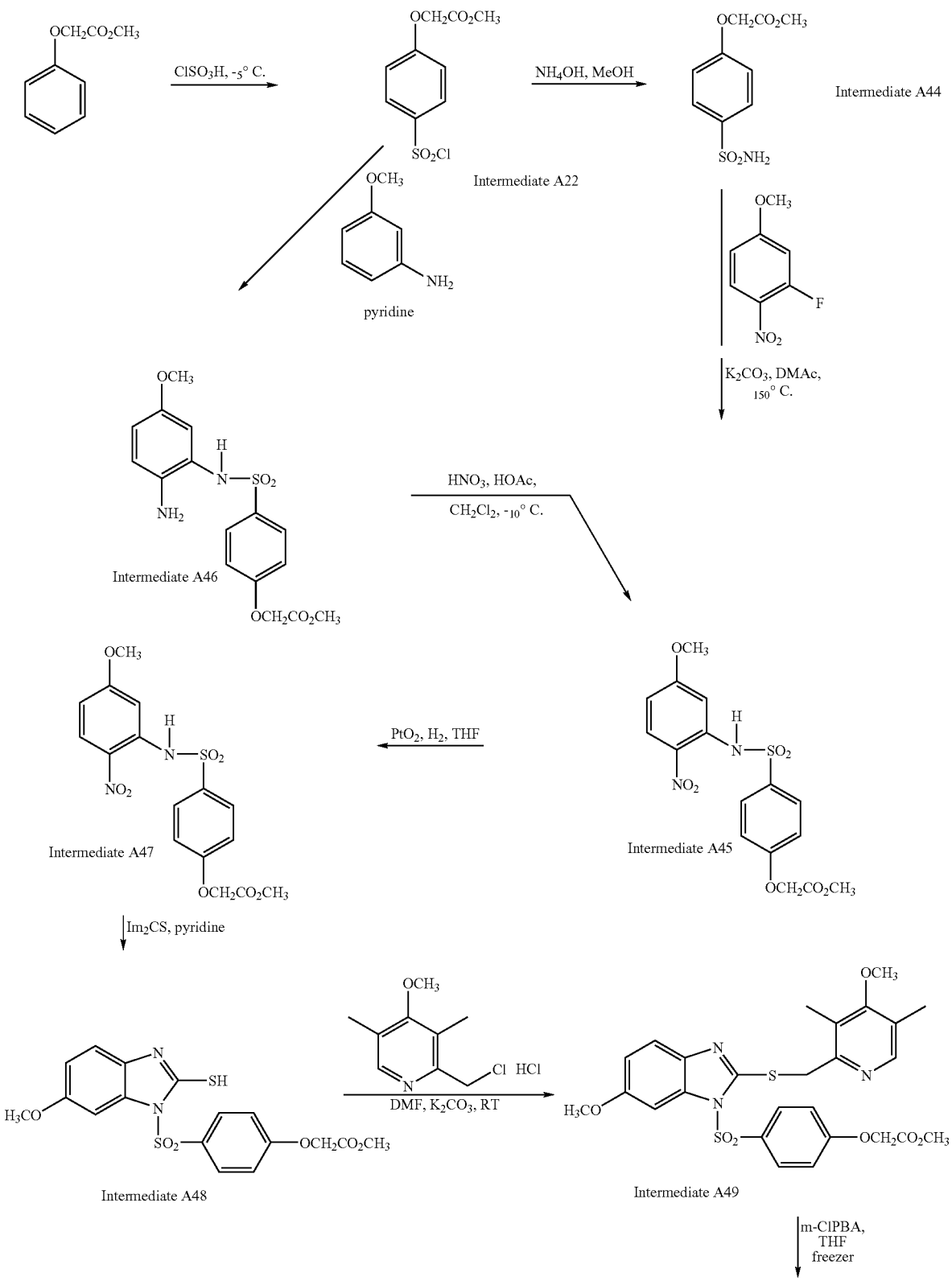

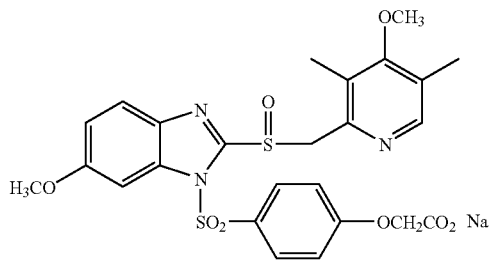

Compound 7

1) 0–1N NaOH, glyme
2) HCl
3) NaHCO₃

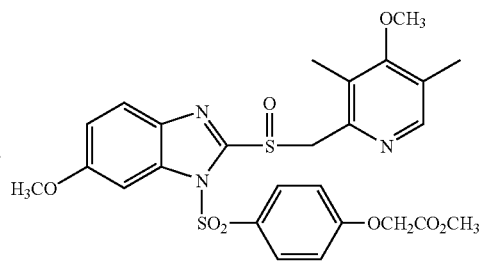

Intermediate A50

Procedure 1 for Making Nitro Sulfonamide Intermediate A45

Methyl 2-(4-sulfamoylphenoxy)acetate (Intermediate A44)

In a 2L 3-necked flask equipped with a mechanical stirrer and a thermometer was placed sulfonyl chloride (Intermediate A22, 68.77 g, 0.26 mol) in methanol (650 mL) and warmed to 30° C. to obtain a solution. To this solution was added methanolic ammonia (159 mL of 4.9 M). The reaction was stirred for 2 hr at room temperature and then stored in a refrigerator for 4 hr. The solid was collected, washed with methanol (100 mL), hexane (300 mL), and dried to give 55 g (86%) of the title compound, sulfonamide as a white solid.

3-Fluoro-4-nitroanisole

A solution of 3-fluoro-4-nitrophenol (75 g, 0.48 mol) in acetone (700 mL) was cooled in an ice-water bath. 1,8-Diazabicyclo[5,4,0]undec-7-ene (145 g, 0.96 mol) was then added over ca. 5 min. Finally, iodomethane (135 g, 0.96 mol) was added over 10 min. The mixture was stirred at room temperature for 16 hr. Additional 1,8-diazabicyclo[5,4,0]undec-7-ene (73 g, 0.48 mol) and iodomethane (68 g, 0.48 mol) were added, and the mixture was warmed to 50° C. for 1 hr. After a solid was removed by filtration, the concentrated filtrate was mixed with ethyl acetate and 1 M hydrochloric acid. The organic layer was washed with additional hydrochloric acid and aqueous sodium bicarbonate, concentrated, and stirred in 1% ethyl acetate in hexanes. The resulting solid was collected and dried to give 72 g (88%) of the title compound.

Methyl 2-(4-{[(5-methoxy-2-nitrophenyl)amino]sulfonyl}phenoxy)acetate (Intermediate A45)

Sulfonamide (Intermediate A44, 44.6 g, 0.18 mol), potassium carbonate (41.4 g, 0.3 mol), 3-fluoro-4-nitroanisole (25.65 g, 0.15 mol) and N,N-dimethylacetamide (250 mL) was heated at reflux for 2.5 hr. The reaction mixture was poured into a mixture of crushed-ice (800 g) and water (400 mL). The resulting mixture was extracted with ethyl acetate (3×500 mL). The combined organic layers were washed with brine (1×200 mL), filtered through 1PS filter paper and concentrated under reduced pressure to give an oil. The oil was purified by flash chromatography (silica gel, hexane to 50% ethyl acetate in hexane) to give 9.4 g (16%) of the title compound, nitro sulfonamide as a yellow solid.

Procedure 2 for Making Nitro Sulfonamide Intermediate A45

Methyl 2-(4-{[(3-methoxyphenyl)amino]sulfonyl}phenoxy)acetate (Intermediate A46)

Solid sulfonyl chloride (Intermediate A22, 29.1 g, 0.11 mol) in several portions was added to a solution of m-anisidine (12.3 g, 0.1 mol) in pyridine (250 mL). The resulting mixture was stirred at room temperature overnight under argon. The reaction mixture was poured into a cold solution of 3 M hydrochloric acid (1 L) and stirred for 30 min. The pink solid was collected, washed with water and dried to give 33 g (94%) of the sulfonamide.

Methyl 2-(4-{[(5-methoxy-2-nitrophenyl)amino]sulfonyl}phenoxy)acetate (Intermediate A45)

A cold mixture of nitric acid (90 mL of 70%) and acetic acid (140 mL) was added to a solution of sulfonamide (Intermediate A46, 31.59 g, 0.09 mol) in dichloromethane (750 mL) at −10° C. over 15 min. After 3.5 hr, water (1 L) was added to the reaction mixture. The organic layer was separated, washed with water (1×300 mL), saturated sodium bicarbonate (1×300 mL), brine (1×300 mL), filtered through 1PS filter paper and concentrated under reduced pressure to give 40 g of a dark brown oil. The oil was purified by flash chromatography (silica gel, 30% ethyl acetate in hexane to ethyl acetate) to give 19.2 g of a residue which after trituration with ethyl acetate afforded 7.5 g (21%) of the title compound, nitro sulfonamide.

Methyl 2-(4-{[(2-amino-5-methoxyphenyl)amino]sulfonyl}phenoxy)acetate (Intermediate A47)

A solution of nitro sulfonamide (Intermediate A45, 17.5 g, 0.0044 mol) in tetrahydrofuran (700 mL) was treated with Raney nickel (2 g) for 15 min, filtered through a pad of celite, and hydrogenated over platinum(IV)oxide (1.5 g) until hydrogen uptake ceased. The reaction mixture was filtered through glass fiber filter paper and concentrated under reduced pressure to give 16.2 g (100%) of the title compound, amine as a tan solid.

Methyl 2-{4-[(6-methoxy-2-mercaptobenzimidazolyl)sulfonyl]phenoxy}acetate (Intermediate A48)

Amine (Intermediate A47, 16 g, 0.0437 mol) was dissolved in pyridine (200 mL). To this solution was added 1,1'-thiocarbonyldiimidazole (11.68 g, 0.0655 mol) and stirred at room temperature overnight under argon. To the reaction mixture was added water (400 mL) and stirred for 1 hr. The resulting solid was collected, washed with water (600 mL) and dried to give 16.9 g (95%) of the title compound, thiol.

Methyl 2-[4-({6-methoxy-2-[(4-methoxy-3,5-dimethyl(2-pyridyl))methylthio]benzimidazolyl}sulfonyl)phenoxy]acetate (Intermediate A49)

Anhydrous potassium carbonate (12.45 g, 0.09 mol) was ground in a mortar and pestle and added to a solution of thiol (Intermediate A48, 16.7 g, 0.041 mol) in N,N-dimethylformamide (275 mL). 2-Chloromethyl-3,5-dimethyl-4-methoxypyridine hydrochloride (9.56 g, 0.043 mole) was added to the reaction mixture. After 1 hr, water (1 L) was added and stirred at room temperature for an additional 15 min. The solid was collected, washed with water (1 L), and dried to give 20.3 g (89%) of the title compound, sulfide.

methyl 2-{4-[(6-methoxy-2-(4-methoxy-3,5-dimethyl-2-Pyridylmethylsulfinyl)benzimidazolyl)sulfonyl]phenoxy}acetate (Intermediate A50)

Sulfide (Intermediate A49, 20.05 g, 0.036 mol) was dissolved in tetrahydrofuran (350 mL), and stored in a freezer for 1 hr. Following addition of a cold solution of m-chloroperoxybenzoic acid (11.6 g of 70%, 0.047 mol) in tetrahydrofuran (150 mL), the reaction mixture was returned to the freezer and stored overnight. The reaction mixture was diluted with ethyl acetate (750 mL), washed with 5% sodium metabisulfite (2×200 mL), washed with saturated sodium bicarbonate (2×200 mL) and brine (2×200 mL), filtered through 1PS filter paper, and concentrated under reduced pressure. The concentrate was purified by flash chromatography (silica gel, hexane to ethyl acetate), to give 14.5 g of a foam. The foam was triturated with 35% ethyl acetate in hexane and gave 13 g (63%) of the title compound, sulfoxide as a white solid.

2-{4-[(6-Methoxy-2-{[(4-methoxy-3,5-dimethyl(2-pyridyl))methyl]sulfinyl}benzimidazolyl)sulfonyl]phenoxy}acetic acid sodium salt (Compound 7)

A solution of 0.1 N sodium hydroxide (20 mL) was added to a solution of sulfoxide (Intermediate A50, 11.46 g, 0.02 mol) in glyme (750 mL). The resulting mixture was extracted with ethyl acetate (2×400 mL). The combined organic layers were back extracted with water-brine, 1:1 (200 mL). The combined aqueous layers were acidified with 3 M hydrochloric acid (20 mL). After adding brine (200 mL), the resulting solution was extracted with ethyl acetate (5×250 mL). The combined organic layers were filtered through 1PS filter paper and concentrated under reduced pressure to give a solid residue. The solid residue was triturated with ethyl acetate (100 mL). The product collected and dried to give 4.5 g (40%) of 2-{4-[(6-methoxy-2-{[(4-methoxy-3,5-dimethyl(2-pyridyl))methyl]sulfinyl}benzimidazolyl)sulfonyl]phenoxy}acetic acid (sulfoxide acid).

To a suspension of the sulfoxide acid (4.47 g, 0.008 mol) in glyme (75 mL) was added a solution of sodium bicarbonate (0.672 g, 0.008 mol) in water (50 mL). The reaction mixture was extracted with ethyl acetate (4×50 mL). The combined organic layers were back extracted with water (2×25 mL). The combined aqueous layers were lyophilized to give 4.1 g (88%) of the title compound.

$^1$H NMR (D$_2$O, 300 MHz) δ 7.65 (t, 3H), 7.25 (d, 1H), 6.95 (d, 1H), 6.7 (m, 3H), 4.7-4.5 (AB, 2H), 4.65 (water of crystallization), 4.15 (s, 2H), 3.5 (s, 3H), 3.35 (s, 3H), 1.5 (s, 3H), 1.75 (s, 3H).

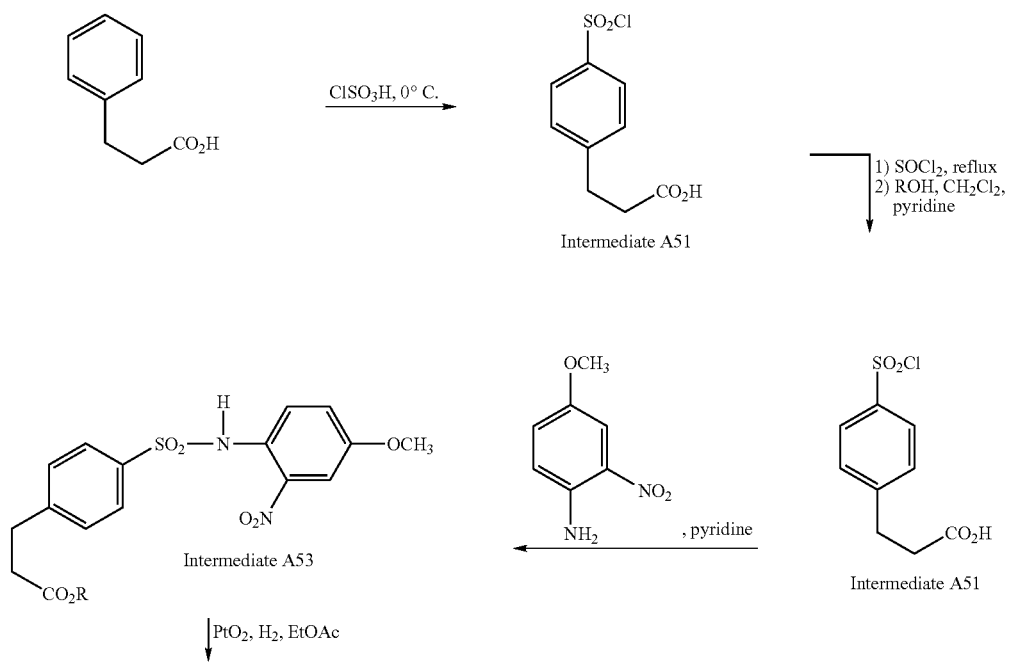

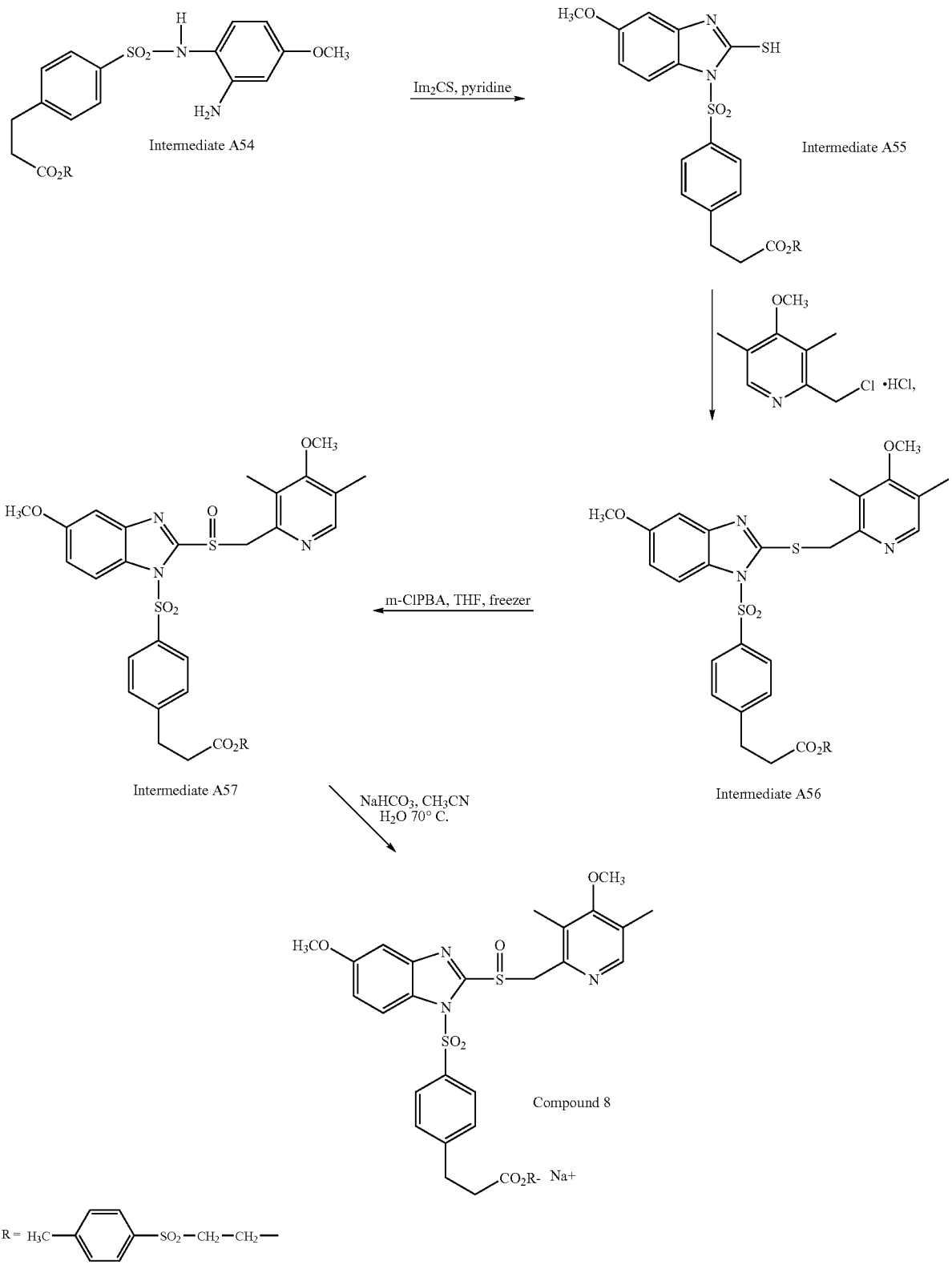

3-[4-(Chlorosulfonyl)phenyl]propionic acid (Intermediate A51)

Solid 3-phenylpropionic acid (45 g, 0.3 mol), in portions, was added to chlorosulfonic acid (174.75 g, 100 mL, 1.5 mol) at −5° C. to 0° C. over 45 min. After 1 hr, the reaction mixture was poured into vigorously stirred crushed-ice (500 g). After 30 min, the white solid was collected, washed with water (1.5 L) and dried to give 12 g of two isomers. The desired isomer was separated by flash chromatography (silica gel, 50% ethyl acetate in hexane to 1% methanol in ethyl acetate) to give 9 g (12%) of the title compound.

2-(4-Methylphenylsulfonyl)ethyl 3-(4-chlorosulfonylphenyl)propanoate (Intermediate A52)

A mixture of 3-[4-(chlorosulfonyl)phenyl]propionic acid (Intermediate A51, 8.2 g, 0.033 mol) and thionyl chloride (23.56 g, 0.198 mol) was refluxed for 1 hr. Excess thionyl chloride was distilled off at atmospheric pressure and finally at reduced pressure to give 9 g acid chloride as an oil. To a mixture of acid chloride (9 g) and 2-(p-tolylsulfonyl)ethanol (6.28 g, 0.0313 mol) in dichloromethane (25 mL) was added triethylamine (3.33 g, 0.033 mol) at room temperature. TLC (ethyl acetate) showed the reaction was complete after 1 hr. The reaction mixture was washed with water (2×50 mL) and brine (1×50 mL), filtered through 1PS filter paper and concentrated under reduced pressure to give an oil. The oil was purified by flash chromatography (silica gel, hexane to 50% ethyl acetate in hexane) to give 7.5 g, (56%) of the title compound, sulfonyl chloride ester as a white solid.

2-(4-Methylphenylsulfonyl)ethyl 3-(4-{[(4-methoxy-2-nitrophenyl)amino]sulfonyl}phenyl)propanoate (Intermediate A53)

Sulfonyl chloride (Intermediate A52, 7.75 g, 0.018 mol), 3-methoxy-2-nitroaniniline (3.02 g, 0.018 mol), and pyridine (60 mL) were mixed and stirred at room temperature overnight under argon. The reaction mixture was concentrated under reduced pressure. The residue was dissolved in ethyl acetate (100 mL), washed with 3 M hydrochloric acid (2×75 mL) and brine (1×100 mL), filtered through 1PS filter paper and concentrated under reduced pressure to give a red oil. The oil was purified by flash chromatography (silica gel, 15% ethyl acetate in hexane to ethyl acetate) to give 7.7 g (76%) of the title compound, nitro sulfonamide as a viscous red oil.

2-(4-Methylphenylsulfonyl)ethyl 3-(4-{[(2-amino-4-methoxyphenyl)amino]sulfonyl}phenyl)propanoate (Intermediate A54)

A solution of the nitro sulfonamide (Intermediate A53, 7.47 g, 0.0133 mol) in ethyl acetate (100 mL) was stirred for 15 min with Raney nickel (3 g), filtered through a pad of celite, and hydrogenated over platinum(IV)oxide (0.25 g) overnight. The reaction mixture was filtered through glass fiber filter paper and concentrated under reduced pressure to give 6.85 g (97%) of the title compound, amine as a light yellow foam.

2-(4-Methylphenylsulfonyl)ethyl 3-{4-[(5-methoxy-2mercaptobenzimidazolyl)sulfonyl]phenyl}propanoate (Intermediate A55)

To a solution of the amine (Intermediate A54, 6.7 g, 0.0126 mol) in pyridine (100 mL) was added 1,1'-thiocarbonyldiimidazole (3.37 g, 0.0189 mol). The reaction mixture was stirred at room temperature for 2 hr. The reaction mixture was diluted with water (150 mL) and extracted with 3:1 dichloromethane/isopropyl alcohol (2×100 mL). The combined organic layers were washed with brine (1×100 mL), filtered through 1PS filter paper and concentrated under reduced pressure to give 8 g of a viscous oil. The oil was purified by flash chromatography (silica gel, 20% ethyl acetate in hexane to 75% ethyl acetate in hexane) to give 5.8 g (80%) of the title compound, thiol as a light yellow foam.

2-(4-Methylphenylsulfonyl)ethyl 3-[4-({5-methoxy-2-[(4-methoxy-3,5-dimethyl(2-pyridyl))methylthio]benzimidazolyl}sulfonyl)phenyl]propanoate (Intermediate A56)

Anhydrous potassium carbonate (3.04 g, 0.022 mol) was ground in a mortar and pestle and added to a solution of the thiol (Intermediate A55, 5.74 g, 0.01 mol) in N,N-dimethylformamide (50 mL). 2-chloromethyl-3,5-dimethyl-4-methoxypyridine hydrochloride (2.33 g, 0.0.105 mol) was added. After 2 hr, 100 ml of 25% isopropyl alcohol in dichloromethane was added to the reaction mixture. The reaction was then washed with water (2×50 mL) and brine (1×50 mL), filtered through 1PS filter paper and concentrated under reduced pressure to give a light brown oil. The oil was purified by flash chromatography (silica gel, 20% ethyl acetate in hexane to 75% ethyl acetate) to give 6.47 g (100%) of the title compound, sulfide as a foam.

2-(4-Methylphenylsulfonyl)ethyl 3-{4-[(5-methoxy-2-(4-methoxy-3,5-dimethyl-2-pyridylmethylsulfinyl)benzimidazolyl)sulfonyl]phenyl}propanoate (Intermediate A57)

The sulfide (Intermediate A56, 6.47 g, 0.01 mol) was dissolved in tetrahydrofuran (100 mL), and stored in a freezer for 1 hr. Following addition of a cold solution of m-chloroperoxybenzoic acid (3.08 g of 70%, 0.0125 mol) in tetrahydrofuran (50 mL), the reaction mixture was returned to the freezer and stored overnight. The reaction mixture was then diluted with ethyl acetate (250 mL) and washed with: 5% sodium metabisulfite (2×100 mL), saturated sodium bicarbonate (2×100 mL) and brine (1×100 mL). The organic layer was filtered through 1PS filter paper, and concentrated under reduced pressure. The concentrate was purified by flash chromatography (silica gel, 25% ethyl acetate in hexane to 1% methanol in ethyl acetate), to give 3.8 g (57%) of the title compound, sulfoxide as a white foam.

3-{4-[(5-Methoxy-2-{[(4-methoxy-3,5-dimethyl(2-pyridyl))methyl]sulfinyl}benzimidazolyl)sulfonyl]phenyl}propanoic acid sodium salt (Compound 8)

To a solution of the sulfoxide (Intermediate A57, 3.71 g, 0.005 mol) in acetonitrile (30 mL), isopropyl alcohol (10 mL), water (20 mL) was added sodium bicarbonate (0.5 g, 0.006 mol). The resulting mixture was heated at 78° C. for 60 min. The resulting mixture was concentrated under reduced pressure to give a glassy solid. The product was dissolved in 2% methanol in dichloromethane (75 mL), filtered to remove insoluble material, and concentrated under reduced pressure to give 34.5 g of a tan foam. This foam was dissolved in water (25 mL) and extracted with ethyl acetate (2×25 mL). The aqueous layer was concentrated under reduced pressure to give 1.35 g (54%) of the title compound as a tan solid.

$^1$H NMR (300 MHz) (D$_2$O) δ 7.75-7.5 (m, 4H), 7.15 (d, 2H), 6.9-6.75 (m, 2H), 4.8-4.6 (dd, 2H), 4.7 (s, water of crystallization), 3.6 (s, 3H), 3.4 (s, 3H), 2.65 (t, 2H), 2.2 (t, 2H), 1.9 (s, 3H), 1.85 (s, 3H).

Reaction Scheme 10
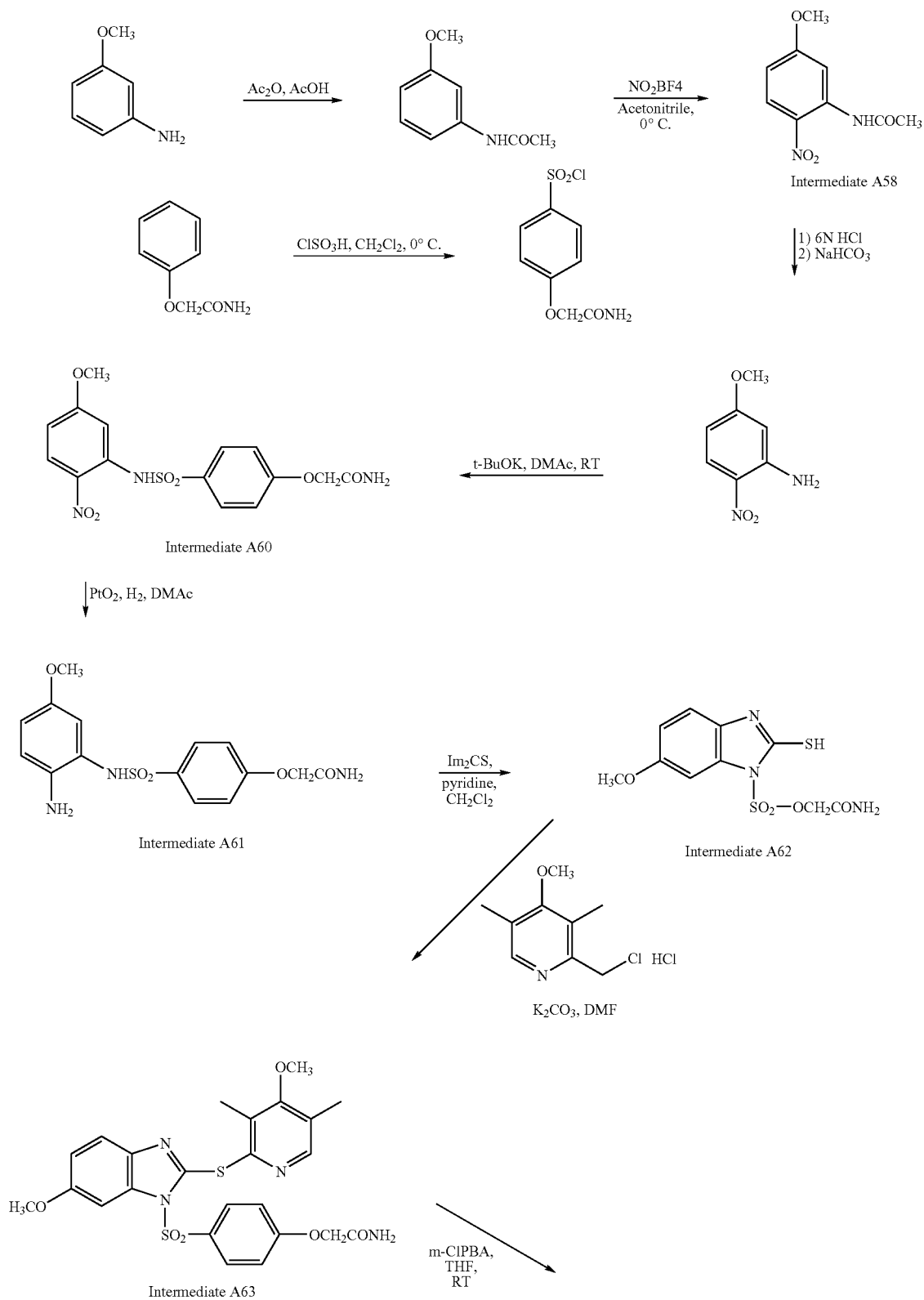

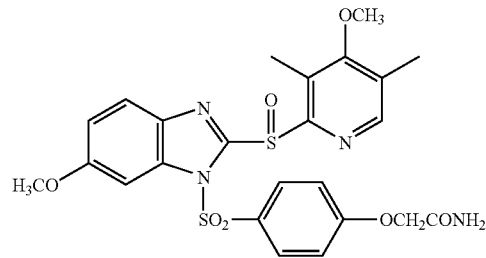

Compound 9

N-(3-Methoxyphenyl)acetamide m-Anisidine (50 g, 0.406 mol) was added to acetic acid (25 mL) and cooled in an ice bath. Acetic anhydride (45.6 g, 0.447 mol) was added dropwise with stirring over 10 min. The resulting mixture was stirred and allowed to come to room temperature. After 1.5 hr the mixture was concentrated under reduced pressure until crystallization commenced. The crystals were collected and allowed to air dry in the hood overnight and finally in a desiccator to afford 66.5 g (99%) of N-(3-methoxyphenyl)acetamide.

N-(3-Methoxy-2-nitrophenyl)acetamide (Intermediate A58)

N-(3-methoxyphenyl)acetamide (14.23 g, 0.086 mol) was dissolved in acetonitrile (200 mL) and cooled to 0° C. Solid nitronium tetrafluoroborate (14.79 g, 0.106 mol) was added in four portions. The temperature rose to about 5° C. during each addition and was allowed to cool down to 0°0 C. between additions. After the last addition of nitronium tetrafluoroborate, water (200 mL) was added to the reaction mixture and the mixture was concentrated under reduced pressure to give approximately 200 mL of a dark oil. The dark oil was dissolved in dichloromethane (200 mL) and washed with water (6×150 mL). The organic layer was concentrated under reduced pressure and dried to obtain 16.1 g of a dark red oil. The red oil was purified by flash chromatography (silica gel, 25% ethyl acetate/hexane) to give 4.53 g (27%) of the crude product. The crude product was triturated with 25% ethyl acetate/hexane to give 3.0 g (17%) of the title compound.

5-Methoxy-2-nitrophenylamine (Intermediate A59)

N-(3-methoxy-2-nitrophenyl)acetamide (Intermediate A58, 3.62 g, 0.0173 mol) was added to 6 N HCl (20 mL) heated to reflux and then cooled. The reaction mixture was filtered and the filtrate was basified with 1 N NaOH and saturated sodium bicarbonate then extracted with ethyl acetate. The solid was partitioned between ethyl acetate and saturated sodium bicarbonate. The two ethyl acetate layers were combined and washed twice with water. The ethyl acetate layer was concentrated under reduced pressure and dried to give 2.92 g (100%) of the title compound.

2-(4-{[(5-Methoxy-2-nitrophenyl)amino]sulfonyl}phenoxy)acetamide (Intermediate A60)

5-methoxy-2-nitrophenylamine (Intermediate A59, 5.1 g, 0.030 mol) was dissolved in N,N-dimethylacetamide (150 mL). Potassium t-butoxide (4.0 g, 0.034 mol) was added to the mixture and stirred for 1 hr. Sulfonyl chloride (10.0 g, 0.035 mol) was then added and the reaction mixture stirred for 1.5 hr. The product was crystallized by slow addition of water to the reaction mixture. The solid was collected and dried in vacuo to give 6.6 g of a brown solid. The solid was recrystallized from acetone to give 3.5 g (31%) of the title compound.

2-(4-{[(2-Amino-5-methoxyphenyl)amino]sulfonyl}phenoxy)acetamide (Intermediate A61)

2-(4-{[(5-methoxy-2-nitrophenyl)amino]sulfonyl}phenoxy)acetamide (Intermediate A60, 2.0 g, 0.0052 mol) was hydrogenated in N,N-dimethylacetamide with platinum(IV)oxide catalyst (0.2 g) until hydrogen uptake ceased. The catalyst was removed by filtration and the resulting mixture was concentrated under reduced pressure. The resulting solid was triturated with ethyl acetate to give 1.7 g (93%) of the title compound, "amine sulfonamide".

2-{4-[(6-Methoxy-2-mercaptobenzimidazolyl)sulfonyl]phenoxy}acetamide (Intermediate A 62)

Amine sulfonamide (Intermediate A61, 11.1 g, 0.032 mol) and pyridine (220 mL) were dissolved in 220 mL of dichloromethane. Thiocarbonyl diimidazole was then added and the reaction mixture was stirred at room temperature. After 2 hrs a precipitate began to form and the reaction was allowed to stir overnight. After which time the reaction was filtered and the solid washed with dichloromethane (2×50 mL) and air dried to give 10.55 g of the title compound, thiobenzimidazole (85%).

2-[4-({6-Methoxy-2-[(4-methoxy-3,5-dimethyl(2-pyridyl))methylthio]benzimidazolyl}sulfonyl)phenoxy]acetamide (Intermediate A 63)

The thiobenzimidazole (Intermediate A62, 12.2 g, 0.031 mol), 2-(chloromethyl)-4-methoxy-3,5,-dimethylpyridinium hydrochloride (6.9 g, 0.031 mol) and potassium carbonate (9.4 g, 0.068 mol) were combined in 160 mL of dimethylformamide. To this solution was added 120 mL of water and within 5 min product began precipitating out of solution. After 8 hours the reaction was filtered and the solid washed with water (2×300 mL) and acetone (1×200 mL) to give 12 g of the title compound, thioether (71%).

1-(4-Methoxycarboxamidebenzenesulfonyl)-6-methoxy-2-[(4-methoxy-3,5-dimethyl-2-pyridinyl)methyl]sulfinyl-1H-benzimidazole (Compound 9)

m-Chloroperbenzoic acid dissolved in 20 mL of THF was added to a solution of thioether (Intermediate A63, 6.0 g, 0.011 mol) in 960 mL of THF at room temperature. After 105 min the solution was diluted with 200 mL of 5% sodium metabisulfite and 800 mL of water. The layers were separated, the aqueous phase was saturated with sodium chloride and the layers separated again. The aqueous phase was finally extracted with 200 mL of ethyl acetate and the organic layer set aside. The THF layers were combined and concentrated in vacuo to give an aqueous slurry which was extracted with the ethyl acetate solution from above. The organic layer was then added directly to a flash silica gel column. The column was eluted with a gradient of ethyl acetate to 5% methanol in ethyl acetate to give 4.05 g (66%) of the title compound.
$^1$H NMR (d$^6$-DMSO, 300 MHz) δ 2.2 (s, 3H), 2.3 (s, 3H), 3.7 (s, 3H), 3.9 (s, 3H), 4.6 (s, 2H), 4.8-5.2 (AB, 4H), 7.0-8.3 (m, 10H)
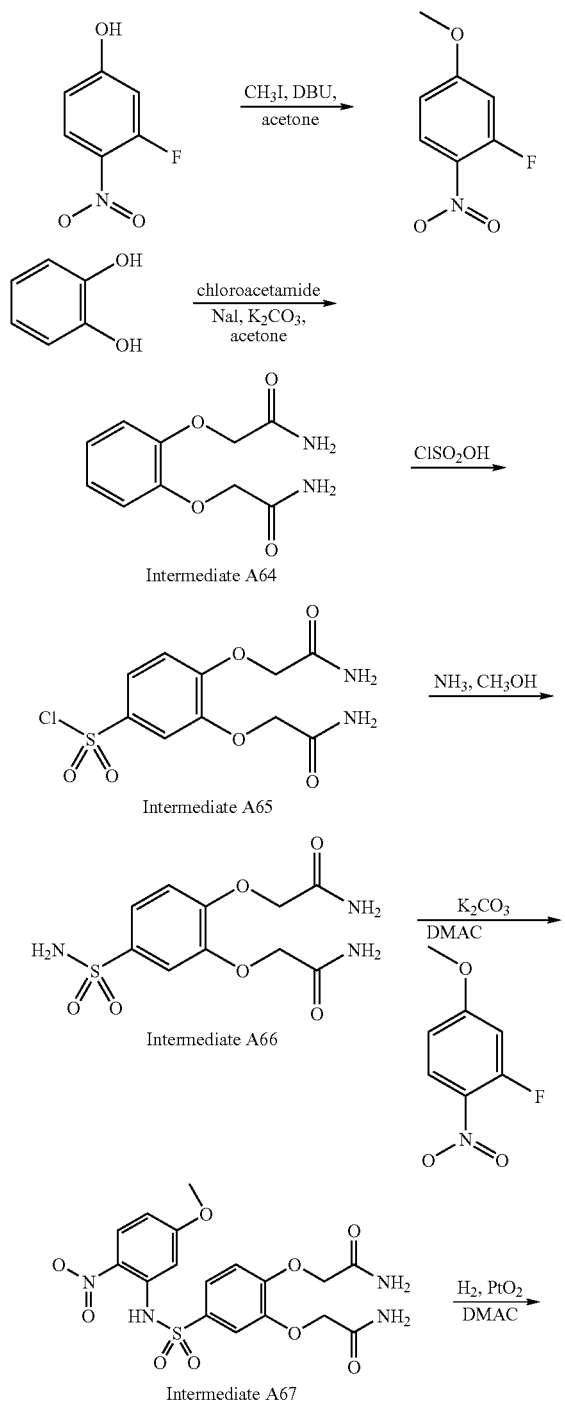
Reaction Scheme 11
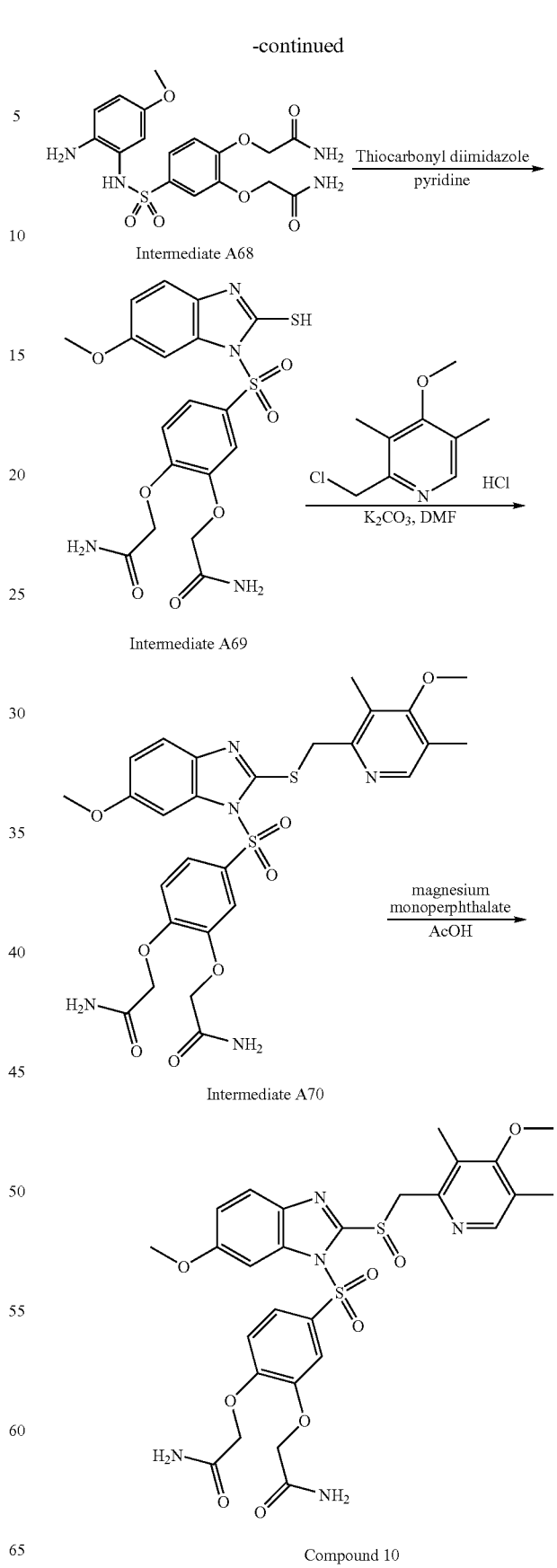

2-Carbamoylmethoxyphenoxyacetamide (Intermediate A 64)

A solution of catechol (100 g, 0.91 mol) and 2-chloroacetamide (178.6 g, 1.91 mol) in acetone (1.5 L) was mixed with potassium carbonate (263.6 g, 1.91 mol) and sodium iodide (28.6 g, 0.191 mol) and heated at reflux overnight. The mixture was diluted with 1.5 L of water, and the resulting solid was collected, washed with water, and triturated with acetone to yield after drying 146.8 g (72%) of the title compound.

2-Carbamoylmethoxy-4-chlorosulfonylphenoxyacetamide (Intermediate A 65)

2-Carbamoylmethoxyphenoxyacetamide (Intermediate A64, 112 g, 0.50 mol) was added portion wise over 15 min to rapidly stirred chlorosulfonic acid (582.5 g, 5.0 mol) and cooled to 0° C. Then dichloromethane (120 mL) was added, and the mixture was heated in a 60°-70° C. bath for 3 hr. The mixture was slowly poured into 1.5 Kg of crushed ice, and water (500 mL) was added. The resulting solid was collected, washed with water and acetone, resuspended in acetone, filtered, washed with acetone, and air dried to yield 125 g (77%) of the title compound.

2-Carbamoylmethoxy-4-aminosulfonylphenoxyacetamide (Intermediate A66)

2-Carbamoylmethoxy-4-chlorosulfonylphenoxyacetamide (Intermediate A65, 12.9 g, 0.040 mol) was dissolved in methanolic ammonia and stirred for 16 hr. The solvent was removed at aspirator pressure, and the residue was crystallized in water. The resulting solid was washed with hot water and several additional portions of water. The product, title compound weighed 8.6 g (71%).

3-Fluoro-4-nitroanisole

A solution of 3-fluoro-4-nitrophenol (75 g, 0.48 mol) in acetone (700 mL) was cooled in an ice-water bath. 1,8-Diazabicyclo[5,4,0]undec-7-ene (145 g, 0.96 mol) was then added over ca. 5 min. Finally, iodomethane (135 g, 0.96 mol) was added over 10 min. The mixture was stirred at room temperature for 16 hr. Additional 1,8-Diazabicyclo[5,4,0]undec-7-ene (73 g, 0.48 mol) and iodomethane (68 g, 0.48 mol) were added, and the mixture was warmed to 50° C. for 1 hr. After a solid was removed by filtration, the concentrated filtrate was mixed with ethyl acetate and 1 M hydrochloric acid. The organic layer was washed with additional hydrochloric acid and aqueous sodium bicarbonate, concentrated, and stirred in 1% ethyl acetate in hexanes. The resulting solid 3-fluoro-4-nitroanisole (72 g, 88%) was collected and air-dried.

2-Carbamoylmethoxy-4-{(5-methoxy-2-nitrophenyl)aminosulfonyl}phenoxyacetamide (Intermediate A67)

A mixture of 4-aminosulfonyl-2-carbamoylmethoxyphenoxyacetamide (Intermediate A66, 12.1 g, 0.040 mol), potassium carbonate (11.0 g, 0.80 mol), and dimethylacetamide (160 mL) was heated at reflux as 3-fluoro-4-nitroanisole (6.84 g, 0.040 mol) in 40 mL dimethylacetamide was added dropwise over 40 min. After an additional 30 min at reflux, the mixture was allowed to cool overnight. It was then diluted with 200 mL of water and filtered with the aid of additional water. The filtrate was brought to pH 5, and the resulting solid was collected and washed with water. After air-drying, the product, title compound weighed 15 g (80%).

2-Carbamoylmethoxy-4-{(5-methoxy-2-aminophenyl)aminosulfonyl}phenoxyacetamide (Intermediate A68)

2-Carbamoylmethoxy-4-{(5-methoxy-2-nitrophenyl)aminosulfonyl}phenoxyacetamide (Intermediate A67, 14 g, 0.031 mol) in 100 mL of dimethylacetamide was hydrogenated with platinum oxide (0.50 g, 0.0022 mol) as catalyst. After the catalyst was filtered off, the mixture was concentrated under high vacuum. The residue was triturated successively with 1:1 hexanes:ethyl acetate and 2:1 dichloromethane:hexanes. The collected solid, title compound, weighed 12.8 g (97%) after air-drying.

2-Carbamoylmethoxy-4-[{6-methoxy-2-mercaptobenzimidazolyl}sulfonyl]phenoxyacetamide (Intermediate A69)

2-Carbamoylmethoxy-4-{(2-amino-5-methoxyphenyl)aminosulfonyl}phenoxyacetamide (Intermediate A68, 12.7 g, 0.030 mol) in 100 mL pyridine was mixed with thiocarbonyldiimidazole (8.0 g, 0.045 mol) in 50 mL pyridine. After ca. 18 hr, the mixture was concentrated at high vacuum. The residue was mixed with 400 mL of water containing 10 mL of pyridine and stirred overnight. The resulting solid was collected, washed with water, and triturated with acetone. After drying, the product, title compound, weighed 11.3 g (81%)

1-(3,4-Dimethoxycarboxamidobenzenesulfonyl)-6-methoxy-2-[(4-methoxy-3,5-dimethyl-2-pyridinyl)methyl]thio-1H-benzimidazole (Intermediate A70)

2-Carbamoylmethoxy-4-[{6-methoxy-2-mercaptobenzimidazolyl}sulfonyl]phenoxyacetamide (Intermediate A69, 11.2 g, 0.024 mol) was mixed with potassium carbonate (7.3 g, 0.053 mol) and dimethylformamide (200 mL). Then 2-chloromethyl-3,5-dimethyl-4-methoxypyridine hydrochloride (5.3 g, 0.024 mol) in 200 mL of dimethylformamide was added. After 15 min, the mixture was diluted with 400 mL of water. After 3.5 hr, the resulting solid, title compound, was collected, washed with water, and air-dried to yield 13.7 g (93%).

2-Carbamoylmethoxy-4-{[6-methoxy-2({4-methoxy-3,5-dimethyl[2-pyridyl}methylsulfinyl)benzimidazolyl]sulfonyl}phenoxyacetamide (Compound 10)

1-(3,4-Dimethoxycarboxamidobenzenesulfonyl)-6-methoxy-2-[(4-methoxy-3,5-dimethyl-2-pyridinyl)methyl]thio-1H-benzimidazole (Intermediate A70, 6.15 g, 0.0100 mol) was dissolved in warm acetic acid (50 mL). This solution was immersed in an ice-water bath, and a cold solution of magnesium monoperoxyphthalate hydrate (5.88 g of 84%, 0.0100 mol) in 50 mL acetic acid was added. After 34 min, the mixture was diluted with 600 mL of ice water containing 110 mL of concentrated ammonium hydroxide. The mixture was stirred 30 min while immersed in the ice-bath and for an additional 30 min at room temperature. The resulting solid was collected, washed with saturated aqueous sodium bicarbonate and water, suspended in methanol, again collected and washed with methanol. The 3.8 g thus obtained were combined with 2.3 g of similarly derived material, washed with hot methanol, and recrystallized from dimethylacetamide/methanol to yield 5.0 g (44% combined) of the title compound.
NMR (300 MHz) (d⁶-DMSO) δ 7.9-7.0 (complex, 11H); 5.1-4.8 (AB, 2H); 4.6 (s, 2H); 4.5 (s, 2H); 3.9 (s, 3H); 3.7 (s, 3H); 2.3 (s, 3H); 2.2 (s, 3H).
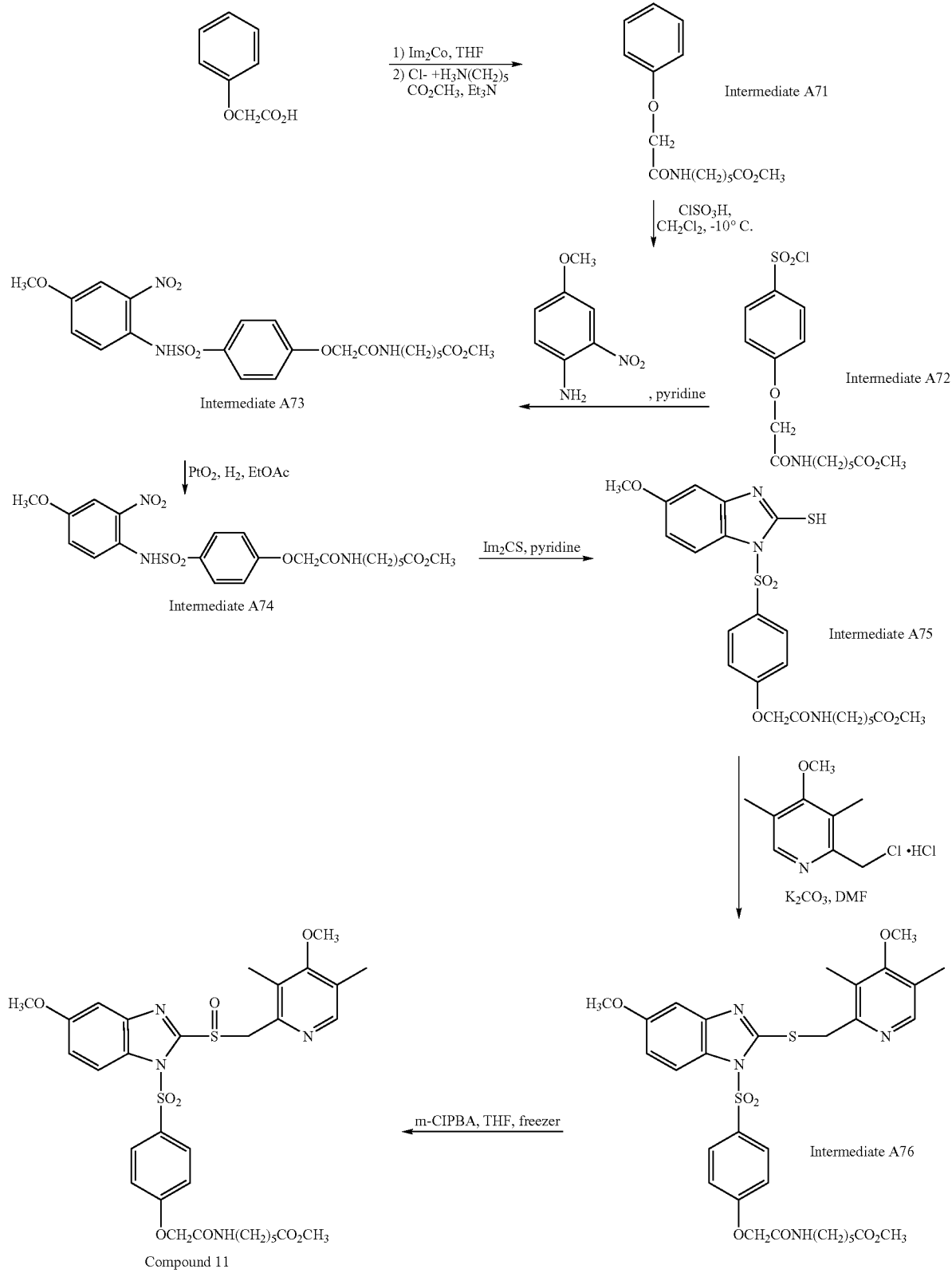

Methyl 6-(2-phenoxyacetylamino)hexanoate (Intermediate A71)

To phenoxyacetic acid (50.0 g, 0.33 mol) dissolved in tetrahydrofuran (210 mL) was slowly added 1,1'-carbonyldiimidazole (56.0 g, 0.35 mol) with additional tetrahydrofuran (30 mL). After stirring for 1.5 hr at room temperature, triethylamine (92 mL, 0.66 mol) was added all at once and methyl 6-aminohexanoate hydrochloride (66.0 g, 0.36 mol) was added in portions over 20 min. The reaction mixture was stirred at room temperature overnight, heated at 50° C. for 20 min, and then stirred at room temperature for 20 hr. The reaction mixture was concentrated under reduced pressure, added to 1 N hydrochloric acid (750 mL) and extracted with ethyl acetate (2×250 mL). The combined organic layers were washed with 1 N hydrochloric acid (1×100 mL), water (1×100 mL), dried over anhydrous sodium sulfate, and concentrated under reduced pressure to give a yellow oil. NMR analysis indicated presence of phenoxyacetic acid. The concentrate was dissolved in toluene (450 mL) and stirred 15 min with 25% sodium bicarbonate (200 mL). The organic layer was filtered through 1 PS paper, concentrated under reduced pressure, diluted with hexanes, and concentrated again, to give 76.89 g (84%) of the title compound, amide, as a yellow oil.

Methyl 6-{2-[4-chlorosulfonylphenoxy]acetylamino}hexanoate (Intermediate A72)

A reaction flask was charged with chlorosulfonic acid (20.9 g, 12 mL, 0.179 mol) and cooled to −10° C. by an ice-methanol bath. Amide (Intermediate A71, 10.0 g, 0.036 mol) was added as a solid in portions over 30 min to the stirring reaction mixture. The reaction mixture was diluted with dichloromethane (30 mL) and heated to 40° C. for 30 min. The reaction mixture was poured into rapidly stirring ice. The aqueous layer was extracted with dichloromethane (2×25 mL) and the combined organic layers were washed with water (1×15 mL), dried through 1PS paper, and concentrated under reduced pressure to give 11.58 g (85%) of the title compound, sulfonyl chloride as a yellow oil.

Methyl 6-[2-(4-(4-methoxy-2-nitrophenylaminosulfonyl)phenoxy)acetylamino]hexanoate (Intermediate A73)

To a solution of 4-methoxy-2-nitroaniline (8.9 g, 0.053 mol) in pyridine (120 mL) was added a solution of the sulfonyl chloride (Intermediate A72, 20.0 g, 0.055 mol) in pyridine (80 mL). After stirring overnight at room temperature, the reaction mixture was concentrated under reduced pressure and partitioned between ethyl acetate (125 mL) and 1.2 N hydrochloric acid (150 mL). The layers were separated, and the aqueous layer was extracted with ethyl acetate (2×75 mL). The combined organic layers were washed with brine (40 mL), filtered through 1PS paper, concentrated under reduced pressure, taken up in dichloromethane with a small amount of ethyl acetate and concentrated again leaving 24.4 g of a red oil. The oil was purified by flash chromatography (silica gel, hexanes:ethyl acetate (9:1) to ethyl acetate) to give 20.7 g of the crude product as an orange oil. This oil was triturated with 20% ethyl acetate in hexane to give 17.1 g (63%) of the title compound nitro sulfonamide as a yellow solid.

Methyl 6-[2-(4-{[(2-amino-4-methoxyphenyl)amino]sulfonyl}phenoxy)acetylamino]hexanoate (Intermediate A74)

A solution of the nitro sulfonamide (Intermediate A73, 7.0 g, 0.014 mol) in ethyl acetate (160 mL) was stirred for 30 min with Raney nickel (0.75 g), filtered through a pad of celite, and hydrogenated over platinum (IV) oxide (0.15 g) overnight. The reaction mixture was filtered through glass fiber filter paper and concentrated under reduced pressure to give 6.58 g (98%) of the title compound, amine as an orange foam.

Methyl 6-(2-{4-[(5-methoxy-2-mercaptobenzimidazolyl)sulfonyl]phenoxy}acetylamino)hexanoate (Intermediate A75)

To a solution of the amine (Intermediate A74, 6.5 g, 0.014 mol) in pyridine (100 mL) was added 1,1'-thiocarbonyldiimidazole (3.6 g, 0.020 mol). The reaction mixture was stirred at room temperature overnight. The reaction was then poured into rapidly stirring water (1 L), and stirred for 3 hr. The solid was collected, washed with water (3×100 mL), pressed well with rubber dam, and air dried to afford 5.83 g (80%) of title compound, thiol as a tan solid.

Methyl 6-{2-[4-({5-methoxy-2-[(4-methoxy-3,5-dimethyl(2-Pyridyl))methylthio]benzimidazolyl}sulfonyl)phenoxy]acetylamino}hexanoate (Intermediate A76)

To a solution of the thiol (Intermediate A75, 5.5 g, 0.011 mol) in N,N-dimethylformamide (50 mL) was added potassium carbonate (3.3 g, 0.024 mol). The reaction mixture was stirred vigorously for 10 min and 2-chloromethyl-3,5-dimethyl-4-methoxypyridine hydrochloride (2.5 g, 0.0093 mol) was added. After 1 hr, the reaction mixture was added to 3:1 dichloromethane/isopropanol (280 mL) and washed with water (2×150 mL). The combined aqueous layers were extracted with 3:1 dichloromethane/isopropanol (40 mL). The combined organic layers were washed with brine (150 mL), dried over anhydrous sodium sulfate, filtered, and concentrated under reduced pressure to give 6.5 g of a solid. The solid was triturated with 3:1 hexanes/ethyl acetate for 20 min and then collected to give 6.30 g (85%) of the title compound, sulfide methyl ester as a tan solid.

Methyl 6-(2-{4-[(5-methoxy-2-{[(4-methoxy-3,5-dimethyl(2-pyridyl))methyl]sulfinyl}benzimidazolyl)sulfonyl]phenoxy}acetylamino)hexanoate (Compound 11)

The sulfide methyl ester (Intermediate A76, 1.0 g, 0.0015 mol) was dissolved in tetrahydrofuran (30 mL), and placed in the freezer for 1.5 hr. Following addition of m-chloroperoxybenzoic acid (0.46 g, 0.0019 mol), the reaction mixture was returned to the freezer and left overnight. The reaction mixture was diluted with ethyl acetate (75 mL), washed with 5% sodium metabisulfite (2×50 mL), 5% sodium bicarbonate (2×50 mL), and brine (50 mL). The organic phase was filtered through 1PS filter paper, and concentrated under reduced pressure. The concentrate was purified by flash chromatography (silica gel, hexanes:ethyl acetate (1:4) to methanol:ethyl acetate=5:95), giving 0.64 g (64%) of the title compound as a yellow foam.

$^1$H NMR (CDCl$_3$, 60 MHz) δ 8.2 (s, 1H), 8.1-7.8 (m, 3H), 7.0-7.3 (m, 4H), 6.5 (br t, 1H), 5.1 (unresolved q, 2H), 4.5 (s, 2H), 3.8 (s, 6H), 3.65 (s, 3H), 3.3 (q, 2H), 2.3 (m, 8H), 1.6 (m, 4H), 1.35 (m, 2H).

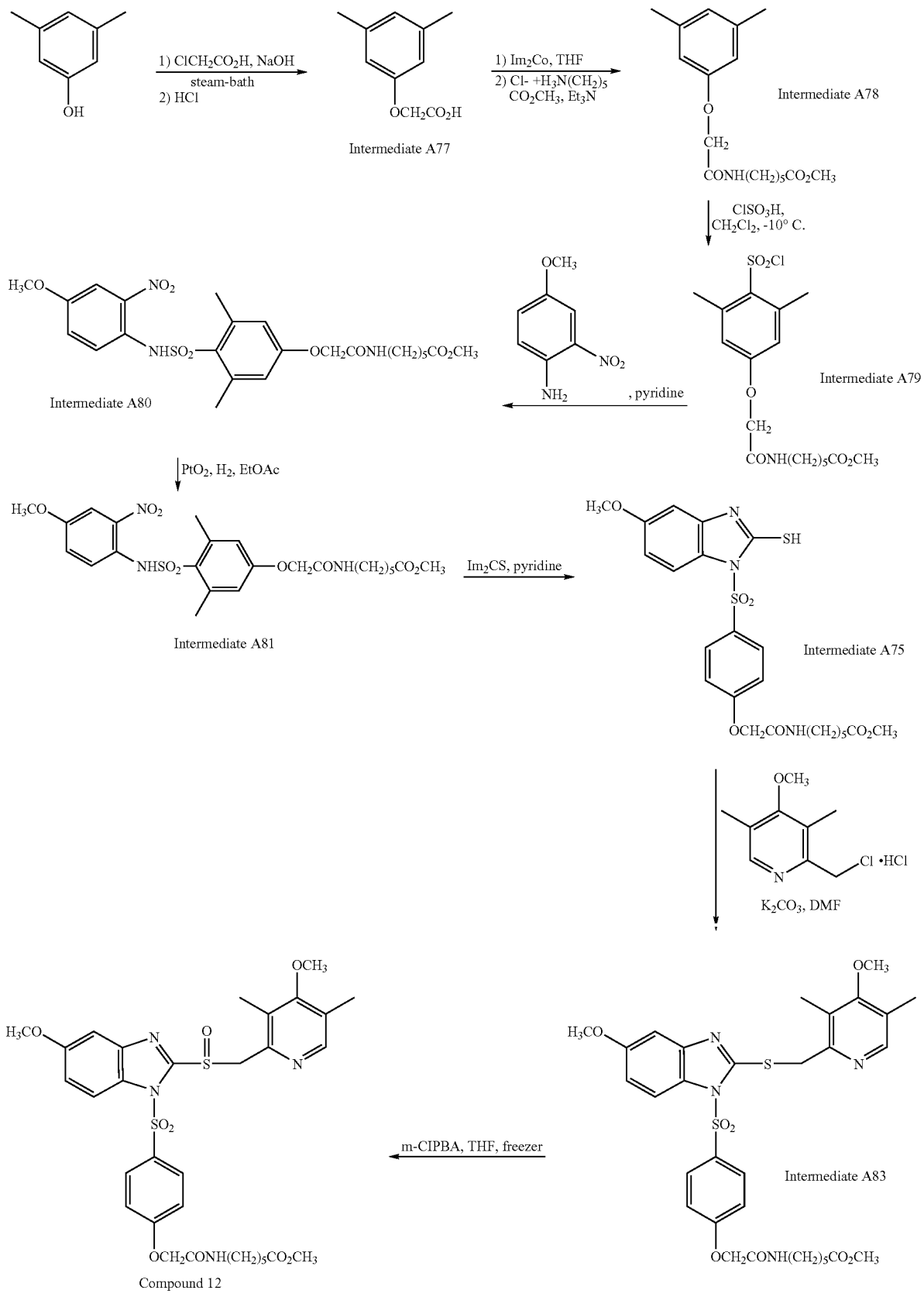
Reaction Scheme 13

3,5-Dimethylphenoxyacetic acid (Intermediate A77)

In a 2L 3-necked flask equipped with a mechanical stirrer and a condenser was placed a solution of sodium hydroxide (168 g, 4.2 mol) in water (1 L). 3,5-Dimethyl phenol (146.4 g, 1.2 mol) was added and the resulting mixture was stirred to get a solution. Chloroacetic acid (226.8 g, 2.4 mol) was added and the resulting mixture was heated on a steam bath for 4 hr. The reaction mixture was cooled in an ice-water bath and acidified with a mixture of concentrated hydrochloric acid (150 mL) and crushed-ice (100 g). After stirring for 30 min the solid was collected, washed with water (500 mL) and suspended in hexane (1 L). The suspension was stirred for 1 hr, solid collected and air dried to give 162 g (75%) of the 3,5-dimethylphenoxyacetic acid.

Methyl 6-[2-(3,5-dimethylphenoxy)acetylamino]hexanoate (Intermediate A78)

In a 5L 3-necked flask equipped with a mechanical stirrer and a dropping funnel was placed 1,1'-carbonyldiimidazole (94.4 g, 0.583 mol) in dichloromethane (1 L). A solution of 3,5-dimethylphenoxyacetic acid (Intermediate A77, 95.4 g, 0.53 mol) in dichloromethane (1250 mL) was added over a period of 60 min under argon. Triethylamine (107.1 g, 1.06 mol) was added followed by addition of a suspension of methyl 6-aminohexanoate hydrochloride (101.1 g, 0.555 mol) in dichloromethane (250 mL) in five portions. After 1 hr the reaction mixture was washed with 3 M HCl (1×1L), 2 M ammonium hydroxide (1×1L), and water (1×1L). The organic phase was then filtered through 1PS filter paper and concentrated under reduced pressure to give an oil. Distillation of the oil gave 101.5 g (62%) of the title compound, amide boiling at 197-202° C. (1 mm). The oil solidified on standing.

Methyl 6-{2-[4-(chlorosulfonyl)-3,5-dimethylphenoxy]acetylamino}hexanoate (Intermediate A79)

To a solution of amide (Intermediate A78, 30.7 g, 0.1 mol) in dichloromethane (100 mL) at −10° C. was added chlorosulfonic acid at such a rate to maintain internal temperature at −10° C. After 1 hr, the reaction mixture was poured into crushed-ice (250 g) and the resulting mixture was extracted with dichloromethane (3×100 mL). The combined organic layers were washed with water (1×100 mL), dried over anhydrous sodium sulfate (20 g) and concentrated under reduced pressure to give 17 g (42%) of the title compound, amide sulfonylchloride as an oil.

Methyl 6-[2-(4-(4-methoxy-2-nitrophenylaminosulfonyl)-3,5-dimethylphenoxy)acetylamino]hexanoate (Intermediate A80)

A solution of amide sulfonylchloride (Intermediate A79, 16.6 g, 0.041 mol) in pyridine (50 mL) was added to a solution of 4-methoxy-2-nitroaniline (6.2 g, 0.037 mol) in pyridine (100 mL) and the resulting mixture was stirred at room temperature overnight under argon. The resulting mixture was concentrated under reduced pressure. To the residue was added 1 M hydrochloric acid (500 mL) and extracted with ethyl acetate (3×200 mL). The combined organic layers were washed with brine (2×100 mL), dried over anhydrous magnesium sulfate (7 g), and concentrated under reduced pressure to give a red oil. The oil was purified by flash chromatography (silica gel, hexane to 75% ethyl acetate in hexane) to give 13.3 g (67%) of the title compound, nitro sulfonamide as an orange-yellow oil.

Methyl 6-[2-(4-{[(2-amino-4-methoxyphenyl)amino]sulfonyl}-3,5-dimethylphenoxy)acetylamino]hexanoate (Intermediate A81)

A solution of nitro sulfonamide (Intermediate A80, 12.89 g, 0.024 mol) in ethyl acetate (150 mL) was treated with Raney nickel (1.5 g) for 10 min, filtered through a pad of celite, and hydrogenated over platinum(IV)oxide (1 g) overnight. The reaction mixture was filtered through glass fiber filter paper and concentrated under reduced pressure to give 11 g (90%) of the title compound, amine as a brown foam.

Methyl 6-(2-{4-[(5-methoxy-2-mercaptobenzimidazolyl)sulfonyl]-3,5-dimethylphenoxy}acetylamino) hexanoate (Intermediate A82)

To a solution of amine (Intermediate A81, 10.9 g, 0.0215 mol) in pyridine (150 mL) was added 1,1'-thiocarbonyldiimidazole (5.75 g, 0.032 mol). The resulting mixture was stirred at room temperature overnight, and then poured into water (2 L). The resulting mixture was extracted with dichloromethane. The combined organic layers were filtered through 1PS filter paper and concentrated under reduced pressure to give a brown viscous oil. The oil was purified by flash chromatography (silica gel, 40% ethyl acetate in hexane to ethyl acetate) to give 8.8 g (75%) of the title compound, thiol as a foam.

Methyl 6-{2-[4-({5-methoxy-2-[(4-methoxy-3,5-dimethyl(2-pyridyl))methylthio] benzimidazolyl}sulfonyl)-3,5-dimethylphenoxy]acetylamino}hexanoate (Intermediate A83)

In a 1L 3-necked flask equipped with a mechanical stirrer was placed the thiol (Intermediate A82, 8.7 g, 0.0158 mol) in N,N-dimethylformamide (75 mL) under argon. Potassium carbonate (4.8 g, 0.0348 mol) and 2-(chloromethyl)-4-methoxy-3,5-dimethylpyridinium hydrochloride (3.69 g, 0.0166 mol) were added and the resulting mixture stirred at room temperature for 6 hr. The reaction mixture was diluted with 25% isopropyl alcohol in dichloromethane (200 mL) and washed with water (2×100 mL). The combined aqueous layers were back extracted with 25% isopropyl alcohol in dichloromethane (1×100 mL). The combined organic layers were concentrated under reduced pressure to give an oil. The oil was triturated with methanol (150 mL) and stored in a freezer for 2 hr. The solid was collected and dried to give 7.7 g (70%) of the title compound, sulfide as a white solid.

Methyl 6-(2-{4-[(5-methoxy-2-{[(4-methoxy-3,5-dimethyl(2-pyridyl))methyl] sulfinyl}benzimidazolyl)sulfonyl]-3,5-dimethylphenoxy}acetylamino)hexanoate (Compound 12)

Sulfide (Intermediate A83, 1.0 g, 0.00143 mol) was dissolved in tetrahydrofuran (30 mL), and stored in a freezer for 1 hr. Following addition of m-chloroperoxybenzoic acid (0.46 g, 0.0019 mol), the reaction mixture was returned to the freezer and left overnight. The reaction mixture was diluted with ethyl acetate (75 mL), washed with 5% sodium metabisulfite (2×50 mL), 5% sodium bicarbonate (2×50 mL), brine (1×50 mL), filtered through 1PS filter paper, and concentrated under reduced pressure. The concentrate was purified by flash chromatography (silica gel, 50% ethyl acetate in hexane to 2% methanol in ethyl acetate), giving 0.55 g (51%) of the title compound as a white foam.
$^1$H NMR (CDCl$_3$ 60 MHz) δ 8.2 (s, 1H), 7.5-7.0 (m, 3H), 6.7 (s, 2H), 6.5 (br t, 1H), 4.8 (unresolved t, 2H), 4.5 (s, 2H), 3.8 (s, 3H), 3.7 (s, 3H), 3.65 (s, 3H), 3.3 (q, 2H), 2.55 (s, 6H), 2.3 (m, 8H), 1.6 (m, 4H), 1.35 (m, 2H).
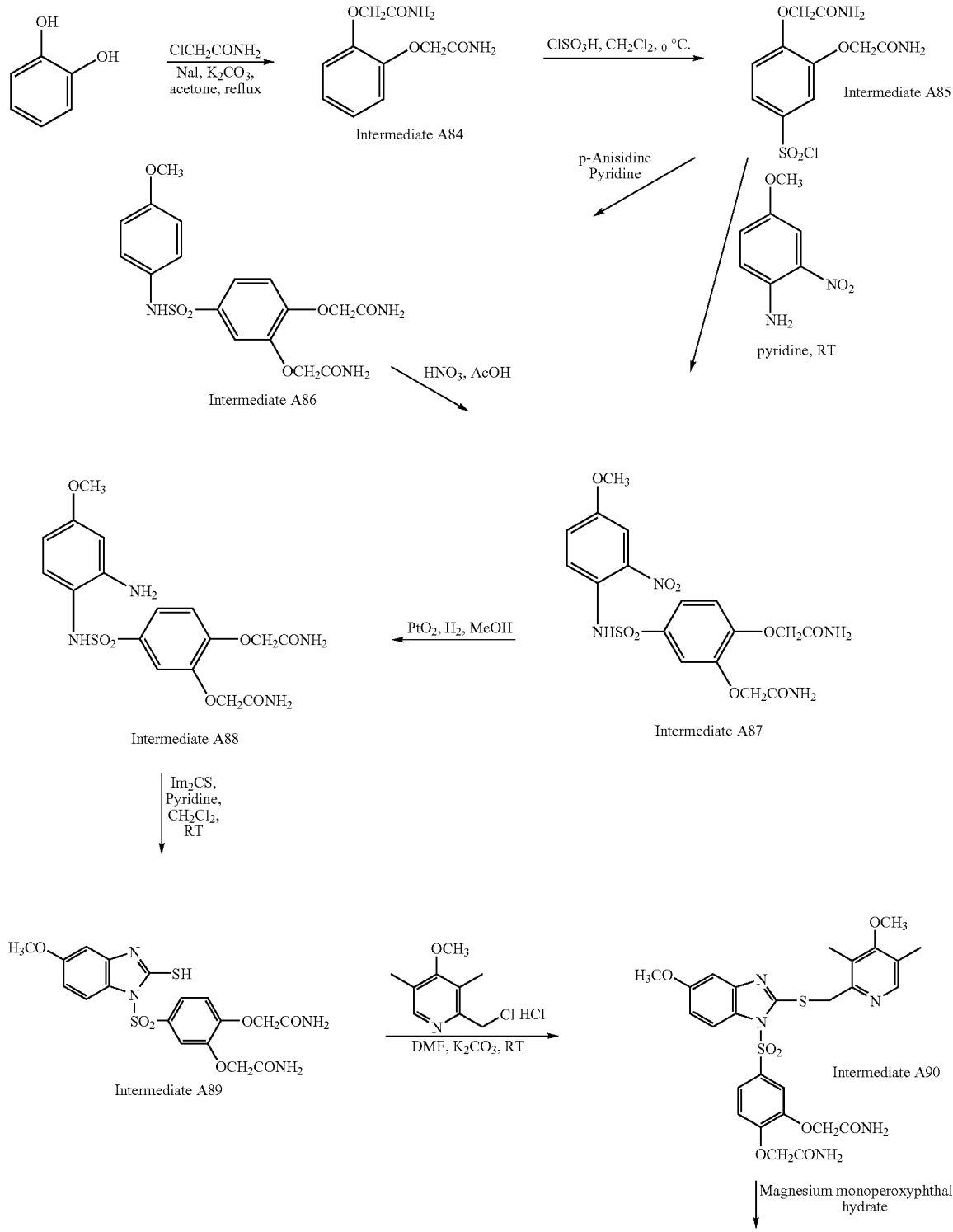
Reaction Scheme 14

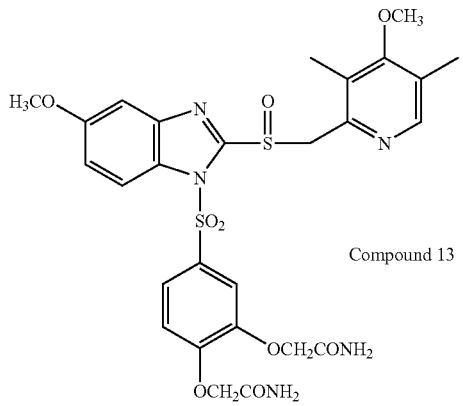

Compound 13

2-[2-(Carbamoylmethoxy)phenoxy]acetamide (Intermediate A84)

A solution of catechol (180.4 g, 1.64 mol) and 2-chloroacetamide (338.5 g, 3.62 mol) in acetone (2 L) was mixed with potassium carbonate (500 g, 3.62 mol) and sodium iodide (54.3 g, 0.362 mol) and heated at reflux overnight. The reaction was cooled to room temperature and the product was precipitated by addition of 2 L of water. The resulting solid was collected, and washed with acetone (3×300 mL) to give after drying 300 g (82%) of the title compound.

2-[2-(Carbamoylmethoxy)-5-(chlorosulfonyl)phenoxy]acetamide (Intermediate A85)

2-Carbamoylmethoxyphenoxyacetamide (Intermediate A84, 112 g, 0.50 mol) was added portion-wise over 15 min to rapidly stirred chlorosulfonic acid (582.5 g, 5.0 mol) cooled to 0° C. Dichloromethane (120 mL) was then added, and the mixture was heated in a 60°-70° C. bath for 3 hr. The mixture was slowly poured into 1.5 Kg of crushed ice, and then water (500 mL) was added. The resulting solid was collected, washed with water (3×500 mL) and acetone (3×500 mL), resuspended in acetone (1 L), again collected, washed with acetone (500 mL), and air dried to yield 125 g (77%) of the title compound.

$^1$H NMR (d$^6$-DMSO, 60 MHz) δ 4.5 (s, 4H), 7.5 (m, 7H).

Procedure 1 for Making 2-(2-(carbamoylmethoxy)-4-(4-methoxy-2-nitrophenylaminosulfonyl)phenoxy)acetamide (Intermediate A87) "nitro sulfonamide"

2-(2-(Carbamoylmethoxy)-4-{[(4-methoxyphenyl)amino]sulfonyl}phenoxy)acetamide (Intermediate A86)

Solid 2-[2-(carbamoylmethoxy)-5-(chlorosulfonyl)phenoxy acetamide (Intermediate A85, 161.25 g, 0.5 mol) was added to a solution of p-anisidine (49.2 g, 0.4 mol) in pyridine (3.5 L) and stirred at room temperature overnight under argon. The reaction mixture was concentrated under reduce pressure. The residue was treated with 0.75 M hydrochloric acid (3 L) and the resulting solid was collected. The solid was washed with water (3×1 L), methanol (750 mL) and dried to give 99 g (60%) of the title compound, sulfonamide.

$^1$H NMR (d$^6$-DMSO, 60 MHz) δ 3.6 (s, 3H), 4.4 (s, 2H), 4.5 (s, 2H), 6.6-7.2 (complex, 7H), 9.8 (s, 1H).

2-(2-(Carbamoylmethoxy)-4-(4-methoxy-2-nitrophenylaminosulfonyl)phenoxy)acetamide (Intermediate A87)

Sulfonamide (Intermediate A86, 98.16 g, 0.24 mol) was dissolved in hot acetic acid (1 L) and was then cooled to 10° C. Nitric acid (17 mL of 70%) was added over a 30 min period. The resulting mixture was stirred, under argon, at 10° C. for an additional 30 min and at room temperature for 30 min longer. During this time, solid formed in the reaction mixture. Water (4 L) was added and the mixture stirred for 1 hr. The solid was collected, washed with water (3×1 L) and dried to give 102.5 g (94%) of the title compound, nitro sulfonamide.

$^1$H NMR (d$^6$-DMSO, 60 MHz) δ 3.8 (s, 3H), 4.6 (s, 2H), 4.8 (s, 2H), 7.6 (complex, 10H), 10.0 (s, 1H)

Procedure 2 for Making 2-(2-(carbamoylmethoxy)-4-(4-methoxy-2-nitrophenylaminosulfonyl)phenoxy) acetamide (Intermediate A87) "nitro sulfonamide"

2-[2-(carbamoylmethoxy)-5-(chlorosulfonyl)phenoxy acetamide (Intermediate A85, 19.35 g, 0.061 mol) was added to a solution of 4-methoxy-2-nitroaniline (67.2 g, 0.4 mol) in pyridine (2 L) at room temperature under argon for 2 hr. The reaction mixture was concentrated under reduce pressure. The residue was purified by flash chromatography (silica gel, ethyl acetate to 15% methanol in ethyl acetate) to give 6.4 g (23%) of the title compound, nitro sulfonamide as a yellow solid.

$^1$H NMR (d$^6$-DMSO, 60 MHz) δ 3.8 (s, 3H), 4.6 (s, 2H), 4.8 (s, 2H), 7.6 (complex, 10H), 10.0 (s, 1H)

2-(4-{[(2-Amino-4-methoxyphenyl)amino]sulfonyl}-2-(carbamoylmethoxy)phenoxy)acetamide (Intermediate A88)

A solution of nitro sulfonamide (Intermediate A87, 100 g, 0.22 mol) in N,N-dimethylacetamide (300 mL) was hydrogenated over platinum(IV)oxide (2 g) until hydrogen uptake ceased (4.5 hr). The reaction mixture was filtered through glass fiber filter paper. Hot water (1500 mL) was added to the filtrate and the resulting mixture was cooled, with stirring, in an ice-methanol bath for 1 hr. The solid was collected, washed with water (2 L), and dried to give 77 g (82%) of the amine as a tan solid.

$^1$H NMR (1:1 d$^6$-DMSO:CDCl$_3$, 60 MHz) δ 3.7 (s, 3H), 4.5 (s, 2H), 4.6 (s, 2H), 4.8 (s (br), 2H), 6.0-7.4 (complex (br), 9H), 8.9 (s br, 1H)

2-{2-(Carbamoylmethoxy)-4-[(5-methoxy-2-mer-captobenzimidazolyl)sulfonyl]phenoxy}acetamide (Intermediate A89)

Amine (Intermediate A88, 57.1 g, ca. 0.134 mol) was dissolved in hot N,N-dimethylacetamide (270 mL) and pyridine (350 mL). To this warm solution was added a solution of 1,1'-thiocarbonyldiimidazole (30 g, 0.168 mol) in N,N-dimethylacetamide (30 mL). The reaction was stirred at room temperature under argon. After 1 hr, the reaction mixture was concentrated under reduced pressure. Cold water (2 L) was added to the residue and. the mixture stirred for 1 hr. The resulting solid was collected, washed with water (2 L) and dried to give 53 g (85%) of the title compound, thiol.

$^1$H NMR (d$^6$-DMSO, 60 MHz) δ 3.8 (s, 3H), 4.6 (s, 2H), 4.7 (s, 2H), 6.8-7.7 (complex (br), 10H)

2-[2-(Carbamoylmethoxy)-4-({5-methoxy-2-[(4-methoxy-3,5-dimethyl(2-pyridyl))methylthio]benzimidazolyl}sulfonyl)phenoxy]acetamide (Intermediate A90)

Anhydrous potassium carbonate (37.3 g, 0.27 mol) was ground in a mortar and pestle and added to a solution of thiol (Intermediate A89, 52 g, 0.11 mol) in N,N-dimethylformamide (1 L). A solution of 2-chloromethyl-3,5-dimethyl-4-methoxypyridine hydrochloride (26 g, 0.117 mol) in N,N-dimethylformamide (1 L) was added followed by addition of water (2 L). The resulting mixture was stirred at room temperature under argon overnight. The solid was collected, washed with water (2 L), and dried to give 54.2 g (80%) of the title compound, sulfide as a white solid.

$^1$H NMR(d$^6$-DMSO, 60 MHz) δ 2.3 (s, 3H), 2.4 (s, 3H), 3.8 (s, 3H), 3.9 (s, 3H), 4.6 (s, 2H), 4.7 (s, 2H), 4.8 (s, 2H), 7.7 (complex, 11H)

1-(3,4-dimethoxycarboxamidebenzenesulfonyl)-5-methoxy-2-[(4-methoxy-3,5-dimethyl-2-pyridinyl)methyl]sulfinyl-1H-benzimidazole (Compound 13)

In a 3L 3-necked flask equipped with a mechanical stirrer sulfide (Intermediate A90, 12.3 g, 0.02 mol) was suspended in acetic acid (100 mL), warmed on a steam bath to obtain a solution and then cooled in an ice-water bath. Magnesium monoperoxyphthalate hydrate (12.96 g of 84%, 0.022 mol) was suspended in acetic acid (100 mL) and stirred to get a milky mixture and then stored in a freezer for 30 min before adding to above cold mixture. The resulting mixture was stirred in an ice-water bath for 1 hr and was then added to a mixture of concentrated ammonia (220 mL) in crushed-ice (500 g). The reaction mixture was extracted with ethyl acetate (2×400 mL). The combined organic layers were washed with saturated sodium bicarbonate (2×150 mL) and brine (1×150 mL), filtered through 1PS filter paper and concentrated under reduced pressure to give 6 g of a yellow residue. The residue was triturated with methanol (25 mL) to give 3.4 g (27%) of the title compound as a white solid.

$^1$H NMR(d$^6$-DMSO, 60 MHz) δ 2.2 (s, 3H), 2.3 (s, 3H), 3.7 (s, 3H), 3.8 (s, 3H), 4.6 (s, 2H), 4.7 (s, 2H), 5.1 (s (br), 2H), 7.7 (complex, 11H)

Reaction Scheme 15

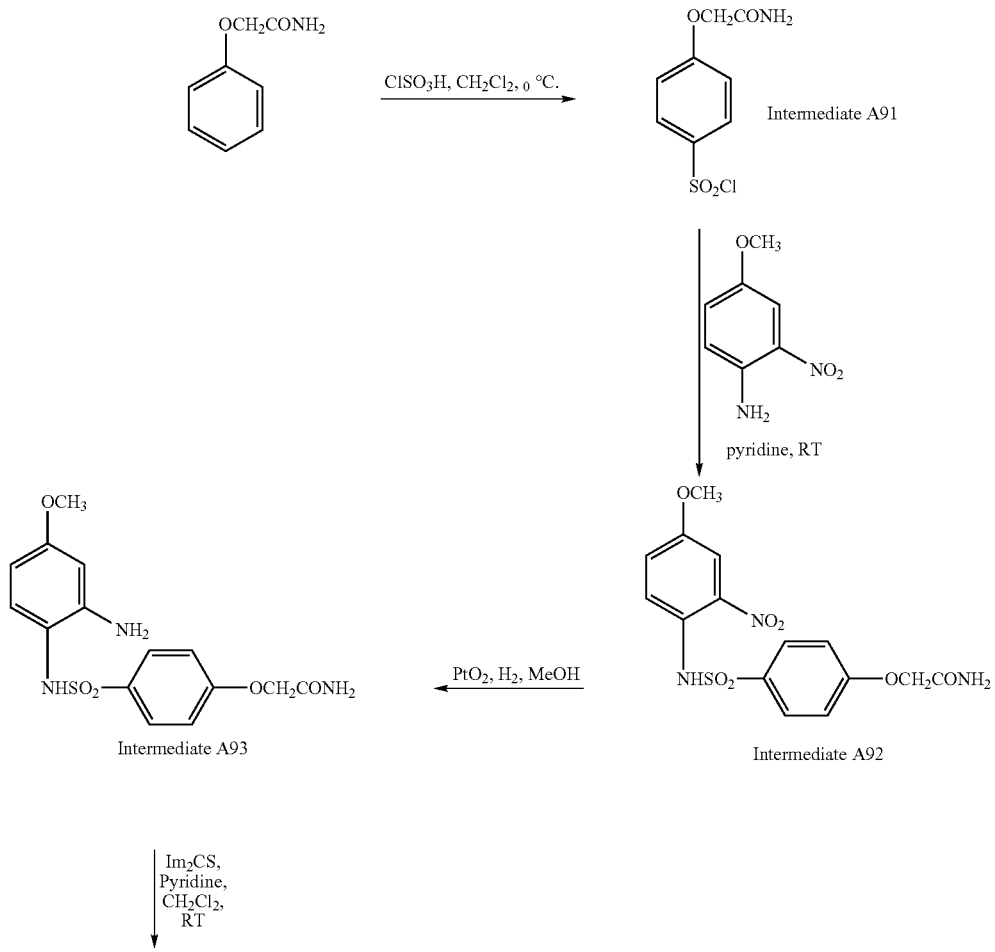

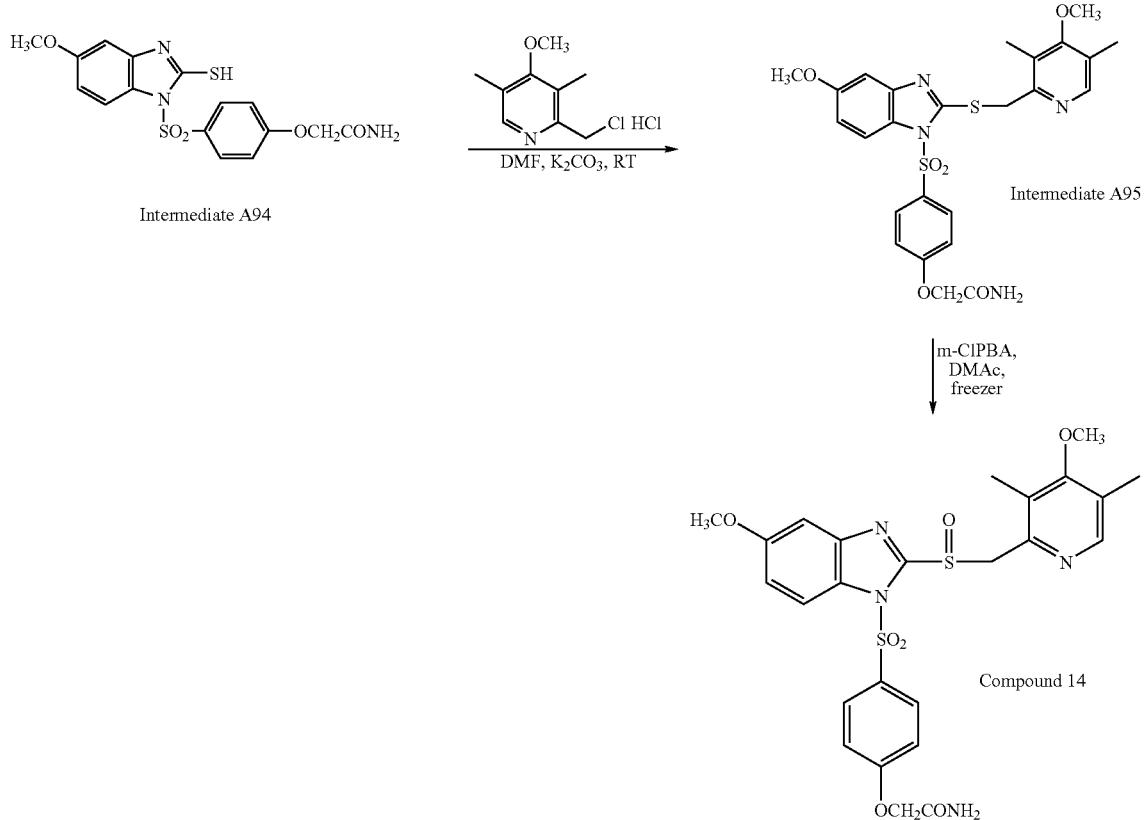

2-{4-(Chlorosulfonyl)phenoxy]acetamide (Intermediate A91)

To a solution of phenoxyacetamide (50 g, 0.333 mol) in dichloromethane (500 mL) was added dropwise chlorosulfonic acid (174.7 g, 1.5 mol) at 0° C. at such a rate to maintain internal temperature between 0 to +5° C. (about 45 min). Some solid formed during this addition. The cooling bath was removed and the reaction mixture was stirred at room temperature overnight. The lower layer in the reaction mixture was added into a vigorously stirring mixture of water (500 mL) and crushed-ice (1500 g). The solid was collected, washed with water (750 mL), and pressed well with a rubber dam. The solid was suspended in acetone (100 mL), stirred for 30 min and collected. After drying, the title compound was isolated as a white solid, weighed 67.3 g (81%).

$^1$H NMR (d$^6$-DMSO, 60 MHz) δ 4.5 (s, 3H), 7.1-7.8 (AB, 4H).

2-(4-(4-methoxy-2-nitrophenylaminosulfonyl)phenoxy)acetamide (Intermediate A92)

Solid 2-[4-(chlorosulfonyl)phenoxy]acetamide (Intermediate A91, 65.87 g, 0.264 mol) was added to a solution of 4-methoxy-2-nitroaniline (27.72 g, 0.165 mol) in pyridine (500 mL) at room temperature under argon. The resulting mixture was stirred at room temperature overnight. The reaction mixture was concentrated under reduced pressure. To the residue was added 0.5 M hydrochloric acid (1000 mL) and stirred for 30 min. The orange solid was collected and recrystallized from acetone to give 42.8 g (68%) of the title compound, nitro sulfonamide as yellow crystals.

$^1$H NMR (d$^6$-DMSO, 60 MHz) δ 3.8 (s, 3H), 4.6 (s, 2H), 7.5 (complex, 9H), 10.2 (s, 1H).

2-(4-{[(2-Amino-4-methoxyphenyl)amino]sulfonyl}phenoxy)acetamide (Intermediate A93)

A solution of nitro sulfonamide (Intermediate A92, 44.8 g, 0.117 mol) in methanol (1 L) was hydrogenated over platinum(IV)oxide (1.5 g) until hydrogen uptake ceased. Upon completion, the reaction mixture contained some solid product. The reaction mixture was warmed to dissolve the product, and then hot filtered. The filtrate was concentrated under reduced pressure to give 38.2 g (80%) of the title compound, amine as a tan solid.

2-{4-[(5-Methoxy-2-mercaptobenzimidazolyl)sulfonyl]phenoxy}acetamide (Intermediate A94)

To a solution of crude amine (Intermediate A93, 36.85 g, ca. 0.105 mol) in pyridine (750 mL) was added a solution of 1,1'-thiocarbonyldiimidazole (28 g, 0.157 mol) in dichloromethane (750 mL). Stirring was continued at room temperature overnight under argon. The resulting solid was collected, washed with dichloromethane (1500 mL) and air dried to give 48 g (theoretical yield=41.2 g) of title compound, thiol which contained pyridine.

$^1$H NMR (d$^6$-DMSO, 60 MHz) δ 3.4 (s, 3H), 4.2 (s, 2H), 7.0 (complex, 8H), 8.2 (m, 1H).

2-[4-({5-Methoxy-2-[(4-methoxy-3,5-dimethyl(2-pyridyl))methylthio]benzimidazolyl}sulfonyl)phenoxy]acetamide (Intermediate A95)

Anhydrous potassium carbonate (34.9 g, 0.253 mol) was ground in a mortar and pestle and added to a solution of thiol (Intermediate A94, 45.2 g, 0.115 mol) in N,N-dimethylformamide (850 mL). A solution of 2-chloromethyl-3,5-dimethyl-4-methoxypyridine hydrochloride (25.53 g, 0.115 mole) in N,N-dimethylformamide (850 mL) was then added to the mixture. Vigorous stirring with a magnetic stir-bar at room temperature continued overnight, under argon. To the reaction mixture was added water (1700 mL) and the product started to precipitate out. After 1 hr, water (1000 mL) was added and, after an additional 30 min stirring, the solid was collected. The solid was washed with water (100 mL) and acetone (150 mL) and then air dried to give 47 g (75%) of the title compound, sulfide as a white solid.

$^1$H NMR (d$^6$-DMSO, 60 MHz) δ 2.2 (s, 3H), 2.3 (s, 3H), 3.7 (s, 3H), 3.8 (s, 3H), 4.5 (s, 2H), 4.7 (s, 2H), 7.6 (complex, 10H).

1-(4-Methoxycarboxamidebenzenesulfonyl)-5-methoxy-2-[(4-methoxy-3,5-dimethyl-2-pyridinyl)methyl]-sulfinyl-1H-benzimidazole (Compound 14)

A solution of 3-chloroperoxybenzoic acid (2.96 g of 70%, 0.012 mol) in N,N-dimethylacetamide (10 mL) was added to a cold solution of sulfide (Intermediate A95, 5.42 g, 0.01 mol) in N,N-dimethylacetamide (80 mL). The resulting mixture was stored in a freezer overnight (18 hr). The reaction mixture was then diluted with ethyl acetate to a volume of 800 mL. Flash chromatography (silica gel, ethyl acetate to 3% methanol, 3% triethylamine in ethyl acetate) using diluted reaction mixture separated the product. The product, weighed 1.75 g, (31%).

$^1$H NMR (d$^6$-DMSO, 300 MHz) δ 2.1 (s, 3H), 2.3 (s, 3H), 3.6 (s, 3H), 3.8 (s, 3H), 4.5 (s, 2H), 4.8-5.2 (AB, 4H), 7.6 (complex, 10H).

What is claimed is:

1. A process for synthesizing compounds of Formula 1, Formula 2, Formula 3 and Formula 4

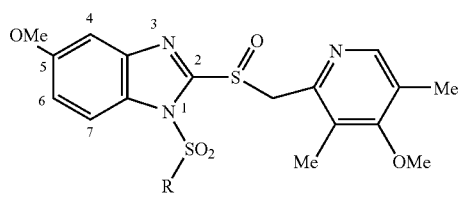

Formula 1

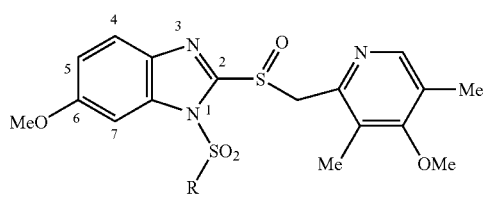

Formula 2

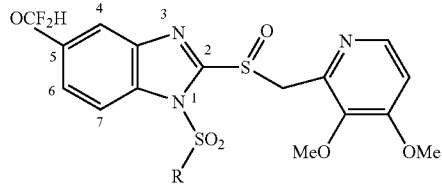

Formula 3

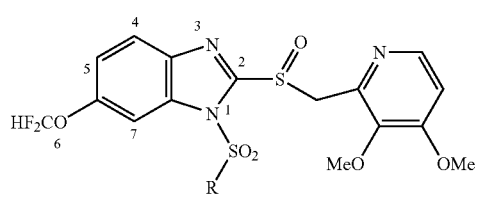

Formula 4 or a pharmaceutically acceptable salt of said compounds
where the R group, represents an alkylsulfonyl, arylsulfonyl, substituted arylsulfonyl, heteroarylsulfonyl or substituted heteroarylsulfonyl group, the process comprising the steps of:

(1) ring closing a compound of Formula 5

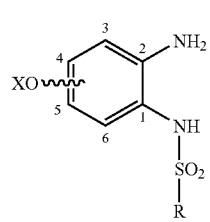

Formula 5 to form a compound of Formula 6

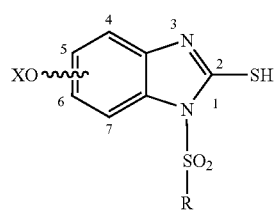

Formula 6

(2) reacting the compound of Formula 6 with a reagent of Formula 7

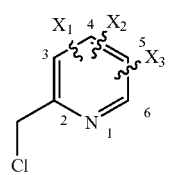

Formula 7 to form a compound of Formula 8

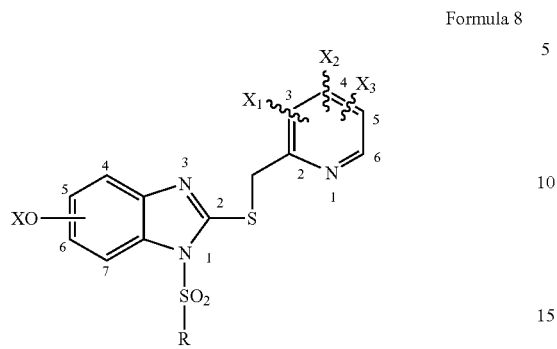

Formula 8

(3) and oxidizing the compound of Formula 8 to form the compound selected from Formulas 1 through 4, wherein XO represents $CH_3O$ or $HF_2CO$ attached to the 4 or 5 position of the compound of Formula 5 and to the 5 or to the 6 position of the benzimidazole moiety of Formulas 1 through 4, $X_1$, $X_2$ and $X_3$ represent either (a) methyl, methoxy and methyl groups attached respectively to the 3, 4 and 5 positions of the pyridine ring, or (b) $X_1$ is methoxy attached to the 3 position of the pyridine moiety, $X_2$ is methoxy attached to the 4 position of the pyridine moiety, and $X_3$ is hydrogen.

2. A process in accordance with claim 1 where the XO group is attached to the 5 position of the benzimidazole moiety.

3. A process in accordance with claim 2 where thiocarbonyldiimidazole ($Im_2C{=}S$), phenyl-isocyanate ($C_6H_5NCS$), or thiophosgen ($CSCl_2$) is used as the reagent in the step of ring closing the compound of Formula 5.

4. A process in accordance with claim 1 where the XO group is attached to the 6 position of the benzimidazole moiety.

5. A process in accordance with claim 4 where thiocarbonyldiimidazole ($Im_2C{=}S$), phenyl-isocyanate ($C_6H_5NCS$), or thiophosgen ($CSCl_2$) is used as the reagent in the step of ring closing the compound of Formula 5.

6. A process in accordance with claim 2 where 3-chloroperoxybenzoic acid (meta-chloroperbenzoic acid, m-ClPBA) or a monoperphthalate is used as the reagent in the step of oxidizing the compound of Formula 8.

7. A process in accordance with claim 4 where 3-chloroperoxybenzoic acid (meta-chloroperbenzoic acid, m-ClPBA) or a monoperphthalate is used as the reagent in the step of oxidizing the compound of Formula 8.

8. A process in accordance with claim 1 where R represents a phenylsulfonyl or substituted phenylsulfonyl group.

9. A process in accordance with claim 1 where R represents a phenylsulfonyl group to which at least one carboxylic acid group or a pharmaceutically acceptable salt of said group is attached.

10. A process in accordance with claim 1
where the R group is defined as a group selected from Formulas (i) through (viii);
where the dashed line represents the bond connecting the R group with the $SO_2$ group,

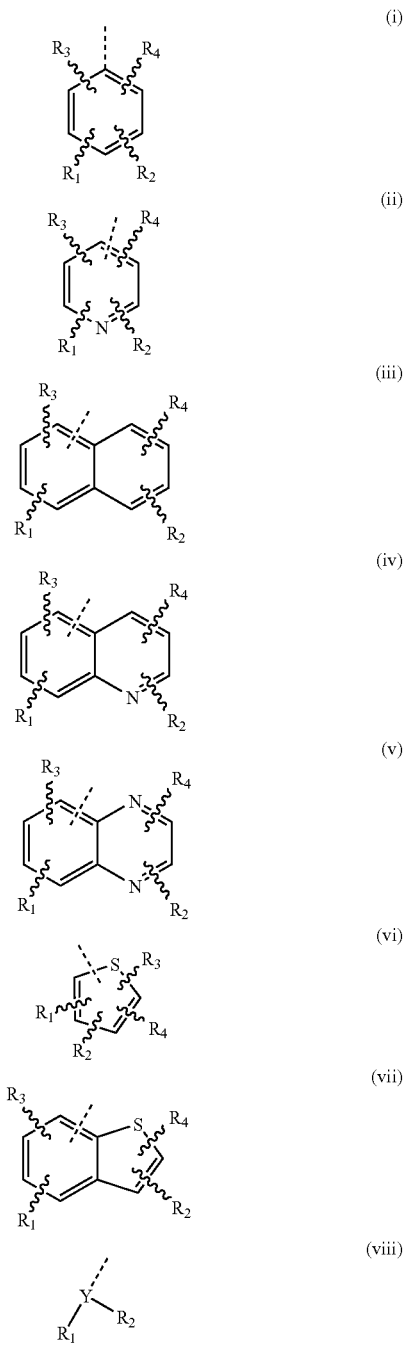

Y is a straight chained or branch-chained disubstituted alkyl group of 1 to 8 carbons, or Y is N;

$R_1$ and $R_2$ independently are H, a straight chained or branch-chained di- or trisubstituted alkyl group of 1 to 12 carbons including 1 or two $R_5$ groups, or a straight chained or branch-chained saturated hydrocarbon skeleton having no more than 12 carbons including 1 or two $R_5$ groups and optionally further including one to three X groups where X is independently selected from the group consisting of —O—, —S—, —$NR_6$—, —NHCO—, —CONH—, —CONHCO—, —COO—, —OCO— and a disubstituted phenyl group which can optionally be substituted with one or two halogen atoms or with one or two R₃ groups; or the R₅ group is directly attached without an intervening R₁ or R₂ group to the aromatic or heteroaromatic ring or to the Y group of formulas (i) through (viii);

R₃ and R₄ independently are H, alkyl of 1 to 3 carbons, fluoroalkyl of 1 to 3 carbons, O-alkyl of 1 to 3 carbons, O-fluoroalkyl of 1 to 3 carbons, S-alkyl of 1 to 3 carbons, S-fluoroalkyl of 1 to 3 carbons;

R₅ is independently H, COCH or a tetrazole moiety or a pharmaceutically acceptable salt of said COCH or tetrazole moiety;

R₆ is H or alkyl of 1 to 3 carbons;

with the provisos that at least one the R₁ and R₂ groups is not H, and at least one R₅ is not H and no more than two R₅ groups are COCH or tetrazole whereby the compound includes at least one but no more than two COCH or tetrazole groups or a pharmaceutically acceptable salt of said COCH or tetrazole moiety;

when Y is —N then neither of the R₁ and R₂ groups is H.

11. A process in accordance with claim 1 where thiocarbonyldiimidazole (Im₂C=S) is used as the reagent in the step of ring closing the compound of Formula 5.

12. A process for synthesizing compounds of Formula 1a and of Formula 2a

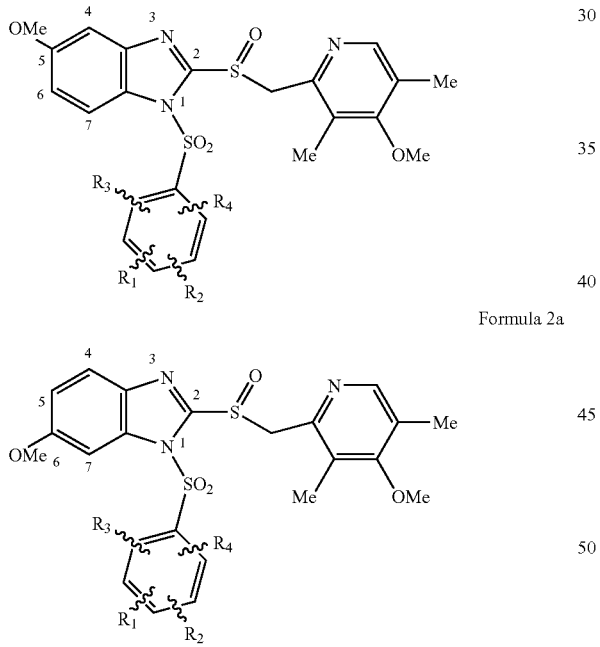

or a pharmaceutically acceptable salt of said compounds where R₁ and R₂ independently are H, a straight chained or branch-chained di- or trivalent alkyl group of 1 to 12 carbons including 1 or two R₅ groups, or a straight chained or branch-chained saturated hydrocarbon skeleton having no more than 12 carbons including 1 or two R₅ groups and optionally further including one to three X groups where X is independently selected from the group consisting of —O—, —S—, —NR₆—, —NHCO—, —CONH—, —CONHCO—, —COO—, —OCO— and a disubstituted phenyl group which can optionally be substituted with one or two halogen atoms or with one or two R₃ groups; or the R₅ group is directly attached without an intervening R₁ or R₂ group to the phenyl ring in Formulas 1a or 2a;

R₃ and R₄ independently are H, alkyl of 1 to 3 carbons, fluoroalkyl of 1 to 3 carbons, O-alkyl of 1 to 3 carbons, O-fluoroalkyl of 1 to 3 carbons, S-alkyl of 1 to 3 carbons, S-fluoroalkyl of 1 to 3 carbons;

R₅ is independently H or COOH;

R₆ is H or alkyl of 1 to 3 carbons;

with the provisos that at least one the R₁ and R₂ groups is not H, and at least one R₅ is not H and no more than two R₅ groups are COOH whereby the compound includes at least one but no more than two COOH groups, the process comprising the steps of:

(1) ring closing a compound of Formula 5a wherein the CH₃O group is attached to the 4 or 5 position of the phenyl ring

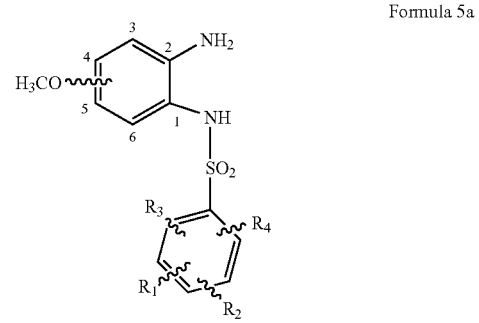

to form a compound of Formula 6a

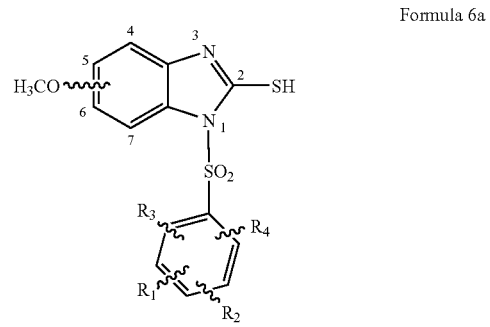

(2) reacting the compound of Formula 6a with a reagent of Formula 7a

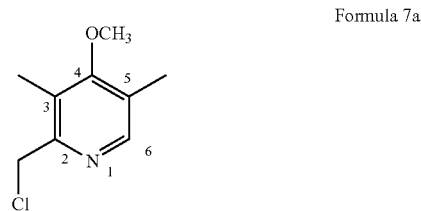

to form a compound of Formula 8a

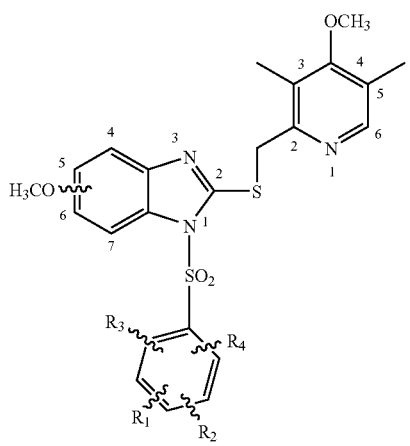

Formula 8a and oxidizing the compound of Formula 8a to form the compound selected from Formulas 1a and 2a.

13. A process in accordance with claim 12 for synthesizing a compound of Formula 1a or a pharmaceutically acceptable salt of said compound.

14. A process in accordance with claim 12 where thiocarbonyldiimidazole ($Im_2C=S$) is used as the reagent in the step of ring closing the compound of Formula 5a.

15. A process in accordance with claim 13 where thiocarbonyldiimidazole ($Im_2C=S$) is used as the reagent in the step of ring closing the compound of Formula 5a.

16. A process in accordance with claim 12 for synthesizing a compound of the formula

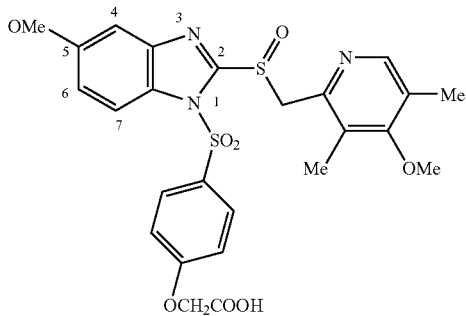

or its pharmaceutically acceptable salt.

17. A process in accordance with claim 12 for synthesizing a compound of the formula

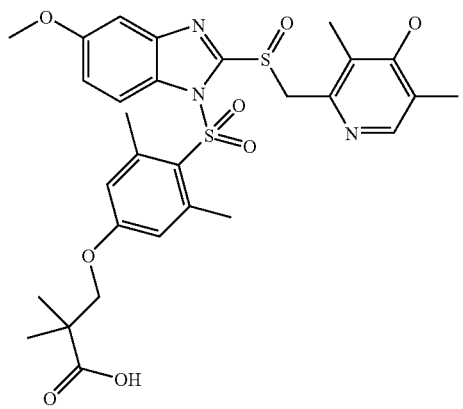

or its pharmaceutically acceptable salt.

18. A process in accordance with claim 12 for synthesizing a compound of the formula

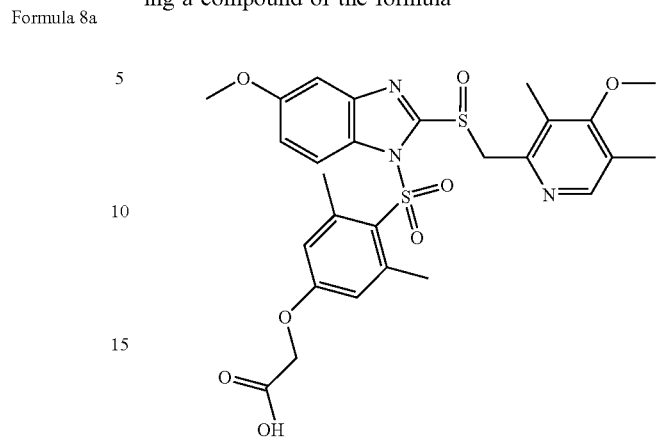

or its pharmaceutically acceptable salt.

19. A process in accordance with claim 12 for synthesizing a compound of the formula

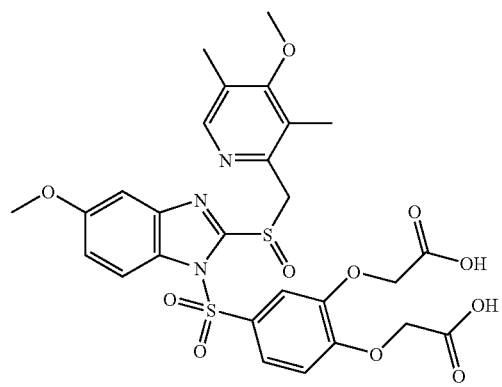

or its pharmaceutically acceptable salt.

20. A process in accordance with claim 12 for synthesizing a compound of the formula

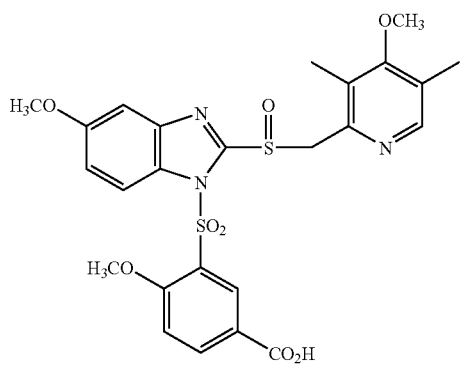

or its pharmaceutically acceptable salt.

21. A process in accordance with claim 12 for synthesizing a compound of the formula

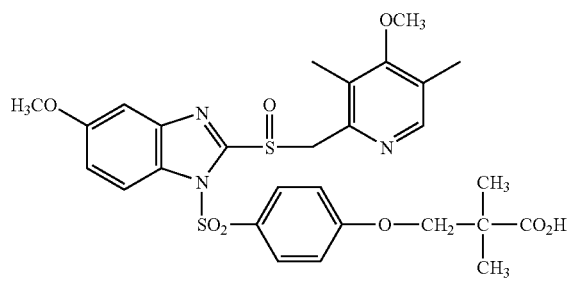

or its pharmaceutically acceptable salt.

22. A process in accordance with claim 12 for synthesizing a compound of the formula

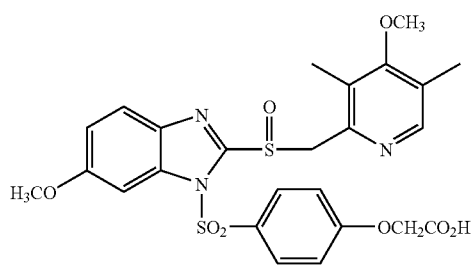

or its pharmaceutically acceptable salt.

23. A process in accordance with claim 12 for synthesizing a compound of the formula

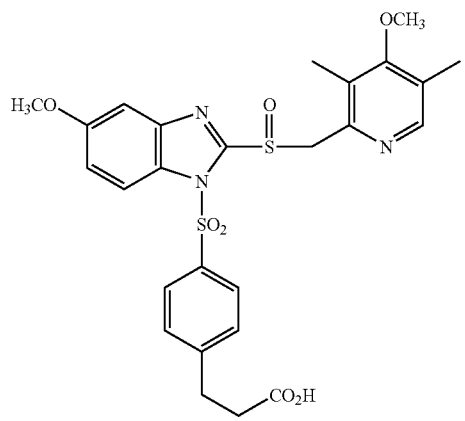

or its pharmaceutically acceptable salt.

24. A process in accordance with claim 12 for synthesizing a compound of the formula

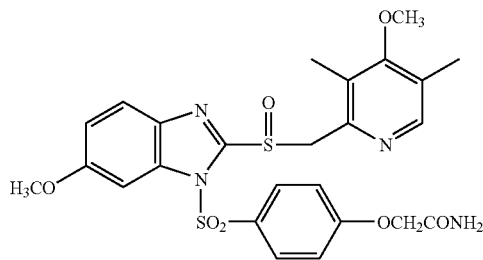

or its pharmaceutically acceptable salt.

25. A process in accordance with claim 12 for synthesizing a compound of the formula

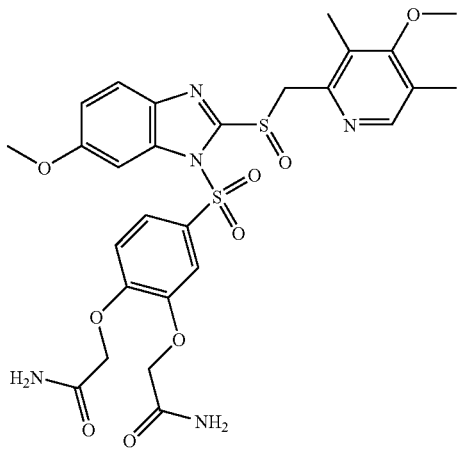

or its pharmaceutically acceptable salt.

26. A process in accordance with claim 12 for synthesizing a compound of the formula

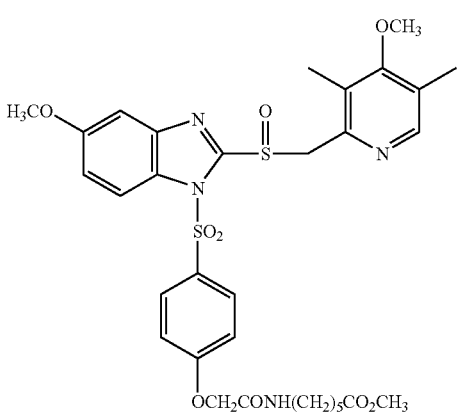

or its pharmaceutically acceptable salt.

27. A process in accordance with claim 12 for synthesizing a compound of the formula

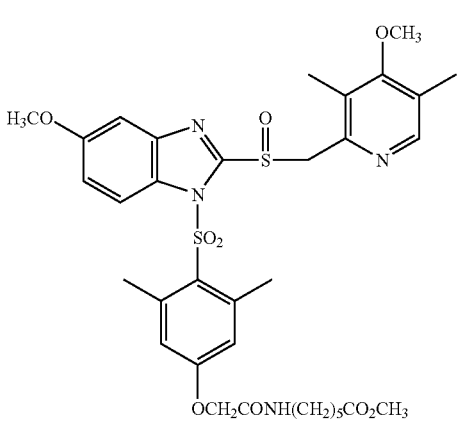

or its pharmaceutically acceptable salt.

28. A process in accordance with claim 12 for synthesizing a compound of the formula
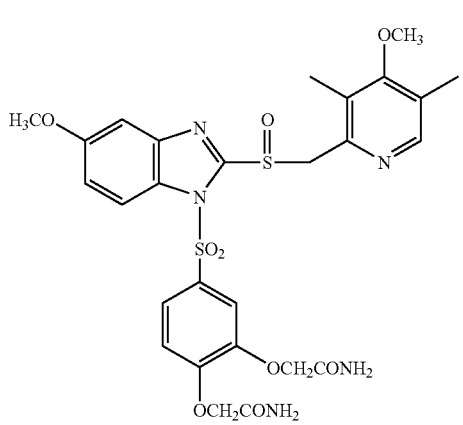
or its pharmaceutically acceptable salt.
29. A process in accordance with claim 12 for synthesizing a compound of the formula
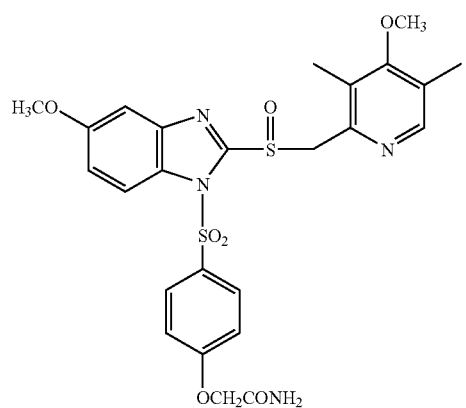
or its pharmaceutically acceptable salt.
* * * * *